(12) United States Patent
French et al.

(10) Patent No.: US 7,998,673 B2
(45) Date of Patent: *Aug. 16, 2011

(54) HYBRIDISATION BEACON AND METHOD OF RAPID SEQUENCE DETECTION AND DISCRIMINATION

(75) Inventors: David John French, Watford (GB); David Gordon McDowell, Middlesex (GB); Tom Brown, Southampton (GB)

(73) Assignee: LGC Limited, Middlesex (GB)

( * ) Notice: Subject to any disclaimer, the term of this patent is extended or adjusted under 35 U.S.C. 154(b) by 93 days.

This patent is subject to a terminal disclaimer.

(21) Appl. No.: 12/010,392

(22) Filed: Jan. 24, 2008

(65) Prior Publication Data

US 2008/0311579 A1 Dec. 18, 2008

Related U.S. Application Data

(63) Continuation-in-part of application No. 10/239,913, filed as application No. PCT/GB01/01430 on Mar. 28, 2001, now Pat. No. 7,348,141.

(30) Foreign Application Priority Data

Mar. 29, 2000 (GB) .................................. 0007622.4
Nov. 2, 2000 (GB) .................................. 0026749.2

(51) Int. Cl.
*C12Q 1/68* (2006.01)
*C07H 21/00* (2006.01)
*C07H 21/02* (2006.01)
*C07H 21/04* (2006.01)
*C12P 19/34* (2006.01)

(52) U.S. Cl. ......... 435/6; 536/22.1; 536/23.1; 536/24.3; 435/91.2

(58) Field of Classification Search ............. 435/6, 91.2; 536/22.1, 23.1, 24.3

See application file for complete search history.

(56) References Cited

U.S. PATENT DOCUMENTS

| | | | |
|---|---|---|---|
| 4,889,818 A | 12/1989 | Gelfand et al. | |
| 5,258,507 A * | 11/1993 | Cruickshank et al. | 536/24.3 |
| 5,480,774 A * | 1/1996 | Hew et al. | 435/6 |
| 5,512,439 A | 4/1996 | Hornes et al. | |
| 5,656,493 A | 8/1997 | Mullis et al. | |
| 5,723,591 A | 3/1998 | Livak et al. | |
| 5,817,461 A | 10/1998 | Austin et al. | |
| 5,849,544 A | 12/1998 | Harris et al. | |
| 5,952,202 A | 9/1999 | Aoyagi et al. | |
| 6,326,486 B1 * | 12/2001 | Hogan et al. | 536/24.32 |
| 6,355,421 B1 | 3/2002 | Coull et al. | |
| 6,451,530 B1 * | 9/2002 | Hawkins | 435/6 |
| 6,465,175 B2 | 10/2002 | Horn et al. | |
| 6,635,427 B2 | 10/2003 | Wittwer et al. | |
| 6,635,452 B1 | 10/2003 | Monforte et al. | |
| 6,716,971 B1 * | 4/2004 | Hawkins et al. | 536/23.1 |
| 7,348,141 B2 * | 3/2008 | French et al. | 435/6 |
| 2003/0022177 A1 | 1/2003 | Wittwer et al. | |
| 2008/0171315 A1 * | 7/2008 | Gelfand et al. | 435/6 |

FOREIGN PATENT DOCUMENTS

| | | |
|---|---|---|
| EP | 0 710 668 | 5/1996 |
| WO | 97/45539 | 12/1997 |
| WO | 98/26093 | 6/1998 |
| WO | 00/79009 | 12/2000 |
| WO | 02/14555 | 2/2002 |

OTHER PUBLICATIONS

Ansorge et al. Automated DNA Sequencing: Ultrasensitive Detection of Fluorescent Bands During Electrophoresis. Nucleic Acids Res. 15:4593-4602 (1987).*
Bellis et al. Primer Design in Fluorescent DNA Sequencing. Nucleic Acids Res. 18:4951-4952 (1990).*
Chehab, F., & Kan, Y. Detection of Specific DNA Sequences by Fluorescence Amplification: A Color Complementation Assay. PNAS 86:9178-9182 (1989).*
Chehab, G., & Kan, Y. Blood 72 : 57A. (1988).*
Landgraf et al. Quantitative Analysis of Polymerase Chain Reaction (PCR) Products Using Primers Labeled with Biotin and a Fluorescent dye. Anal. Biochem. 193:231-235 (1991).*
Murakami et al. Fluorescent-Labeled Oligonucleotide Probes: Detection of Hybrid Formation in Solution by Fluorescence Polarization Spectroscopy Nucleic Acids Res. 19:4097-4102 (1991).*
Schubert et al. One-Step Labeling of Oligonucleotides with Fluorescein During Automated Synthesis. Nucleic Acids Res. 18:3427 (1990).*
Smith et al. Nucleic Acids Res. 13:2399-2412 (1985).*
Voss et al. Automated Fluorescent Sequencing of Cosmid DNA. Nucleic Acids Res. 18 : 1066 (1990).*
Voss et al. Automated Fluorescent Sequencing of Lambda DNA. Nucleic Acids Res. 18 : 5314 (1990).*
Zimmermann et al. A Simplified Protocol for Fast Plasmid DNA Sequencing. Nucleic Acids Res. 18 : 1067 (1990).*

(Continued)

*Primary Examiner* — E C Whisenant
(74) *Attorney, Agent, or Firm* — Wenderoth, Lind & Ponack, L.L.P.

(57) ABSTRACT

A method for detecting specific DNA sequences and discriminating single nucleotide polymorphisms (SNPs) using fluorescently labelled oligonucleotide probes is disclosed. Oligonucleotide probes are labelled with reporter molecules preferentially attached to an internal nucleotide residue. The fluorescence emission of oligonucleotide probes varies significantly when in single-stranded and double-stranded states despite the absence of quencher moieties, allowing reliable detection of complementary DNA targets. The melting temperature of probe/target duplexes permits discrimination of targets that differ by as little as a single nucleotide residue, such that polymorphic targets may be discriminated by fluorescence quantitation and Tm. The hybridisation probes of this invention have been demonstrated to accurately identify homozygous and heterozygous samples using a single fluorescent oligonucleotide and direct investigation of saliva with hybridisation probes permits ultra-rapid genotypic analysis within 35-40 minutes. Target detection and SNP discrimination assays have been achieved in homogeneous, heterogeneous, 'real-time' and solid-phase formats.

29 Claims, 52 Drawing Sheets

OTHER PUBLICATIONS

Figure 2A:
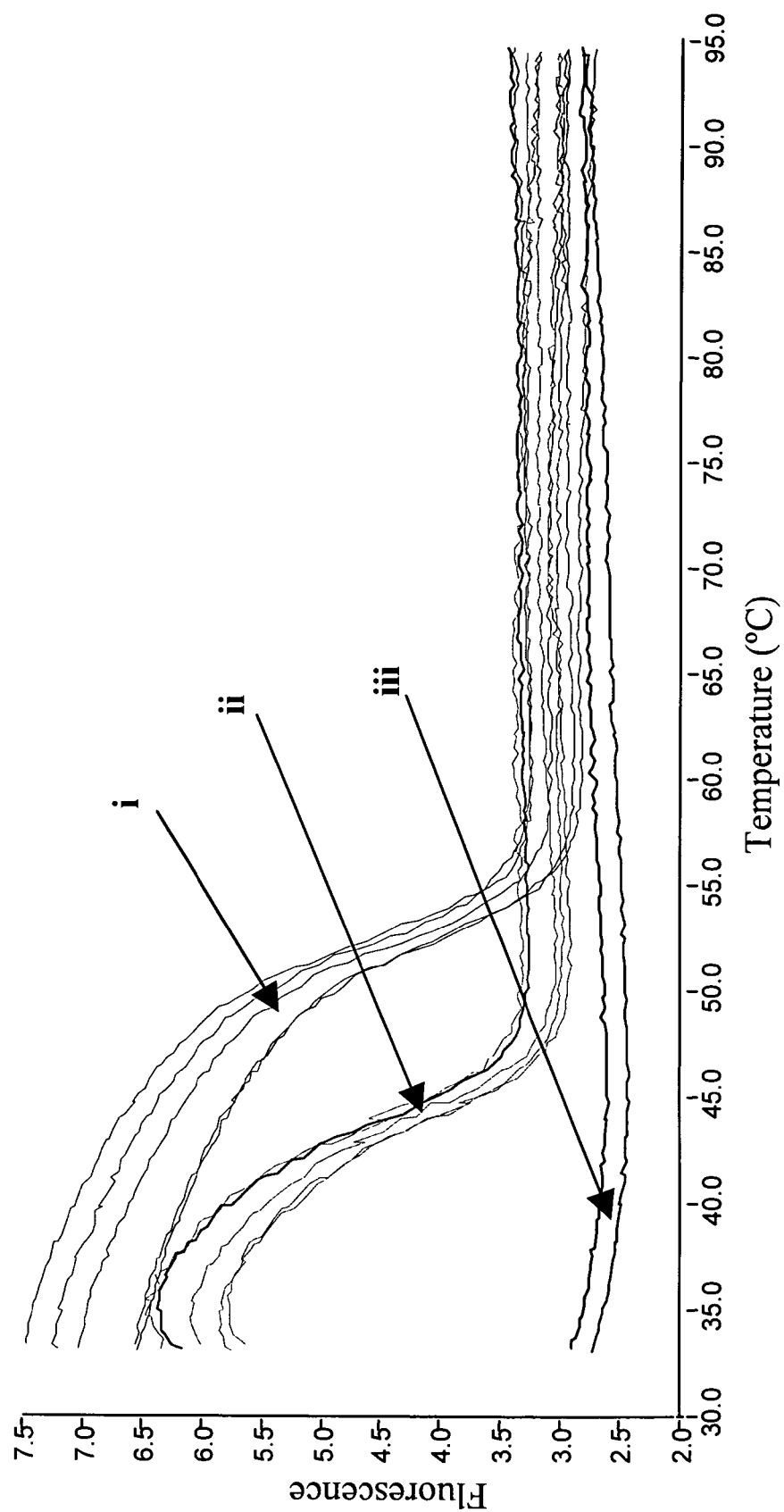

Zimran et al. Detection of the 1226 (Jewish) Mutation for Gaucher's Disease by Color PCR. Am. J. Clin. Pathology 93:788-791 (1990).*

Zimran et al. Analysis of Color PCR by Automated DNA Sequencer. Nucleic Acids Res. 17 : 7538 (1989).*

Cotton, RGH, Current methods of mutation detection. Mutation Research 285 : 125-144 (1993).* de Silva et al., Review : Monitoring hybridization during polymerase chain reaction. J. of Chromatography B, 741 : 3-13 (2000).*

Schubert et al., One-Step labelling of oligonucleotides with fluoresceine during automated synthesis. Nucleic Acids Research 18(11) :3427 (1990).*

French et al., HyBeacon probes: a new tool for DNA sequence detection and allele discrimination. Molecular and Cellular Probes 15 : 363-374 (2001).*

French et al., Ultra-rapid DNA analysis using HyBeacon probes and direct PCR amplification from saliva. Molecular and Cellular Probes 16 : 319-326 (2002).*

A. Murakami et al., "Fluorescent-labelled oligonucleotide probes detection of hybrid formation in solution by fluorescence polarization spectroscopy", Nucleic Acids Research, vol. 19, No. 15, 1991, pp. 4097-4102.

Bernard et al., "Integrated amplification and detection of the C677T point mutation in the methylene-tetrahydrofolate reductase gene by fluorescence resonance energy transfer and probe melting curves", Analytical Biochemistry, vol. 255, Jan. 1998, pp. 101-107.

M. Nauck et al., "Rapid, Homogenous Genotyping of the 4G/5G Polymorphism in the Promoter Region of the PAI 1 Gene by Fluorescence Resonance Energy Transfer and Probe Melting Curve", Clinical Chemistry, vol. 45, No. 8, Aug. 1, 1999, pp. 1141-1147.

Giessendorf et al., "Molecular Beacons: a new approach for semiautomated mutation analysis," Clinical Chemistry, vol. 44, No. 3, pp. 482-486 (1998).

French et al., HyBeacon TM probes: A new tool for DNA sequence detection and allele discrimination, vol. 15, No. 6, pp. 363-374 (Dec. 2001).

Ishiguro et al., "Fluroescence detection of specific sequence of nucleic acids by oxazole yellow-linked oligonucleotides. Homogeneous quantitative monitoring of in vitro transcription," Nucleic Acids Research, vol. 24, No. 24, pp. 4992-4997 (1996).

International Preliminary Examining Report, Oct. 21, 2002, in International Application No. PCT/GB01/01430.

* cited by examiner

Figure 1
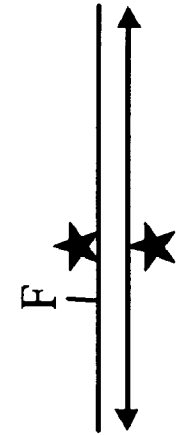
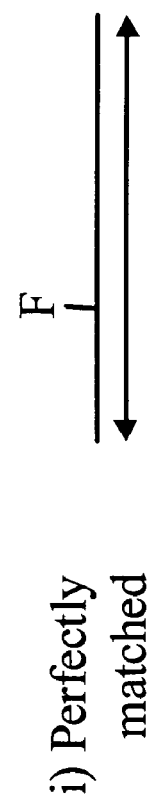 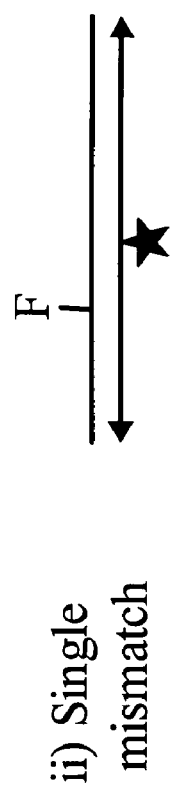 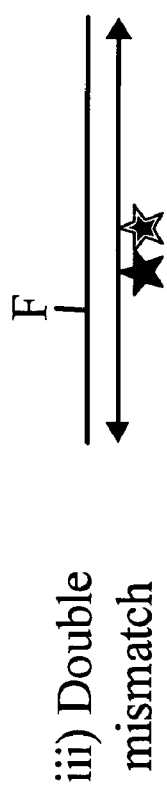

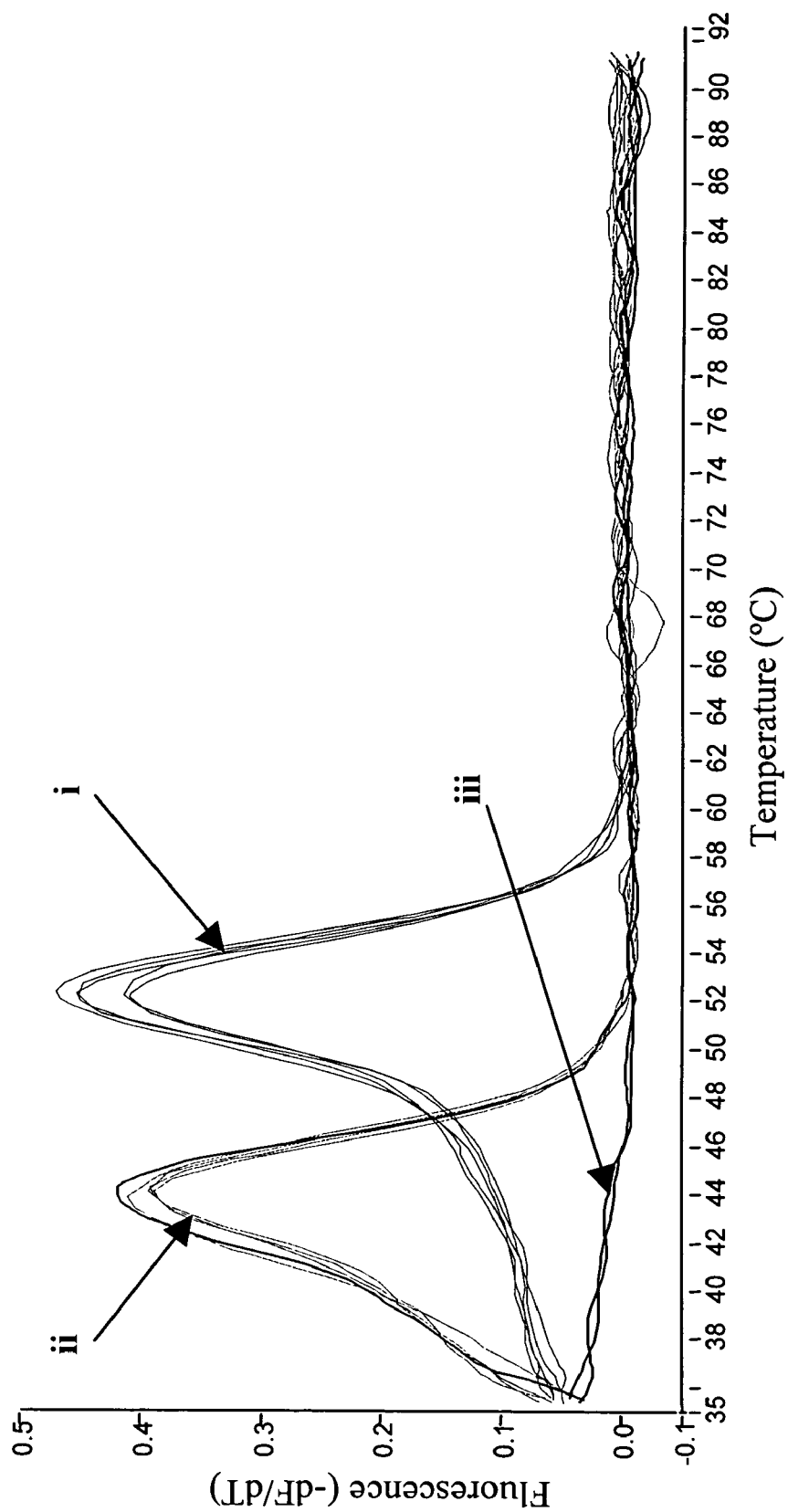

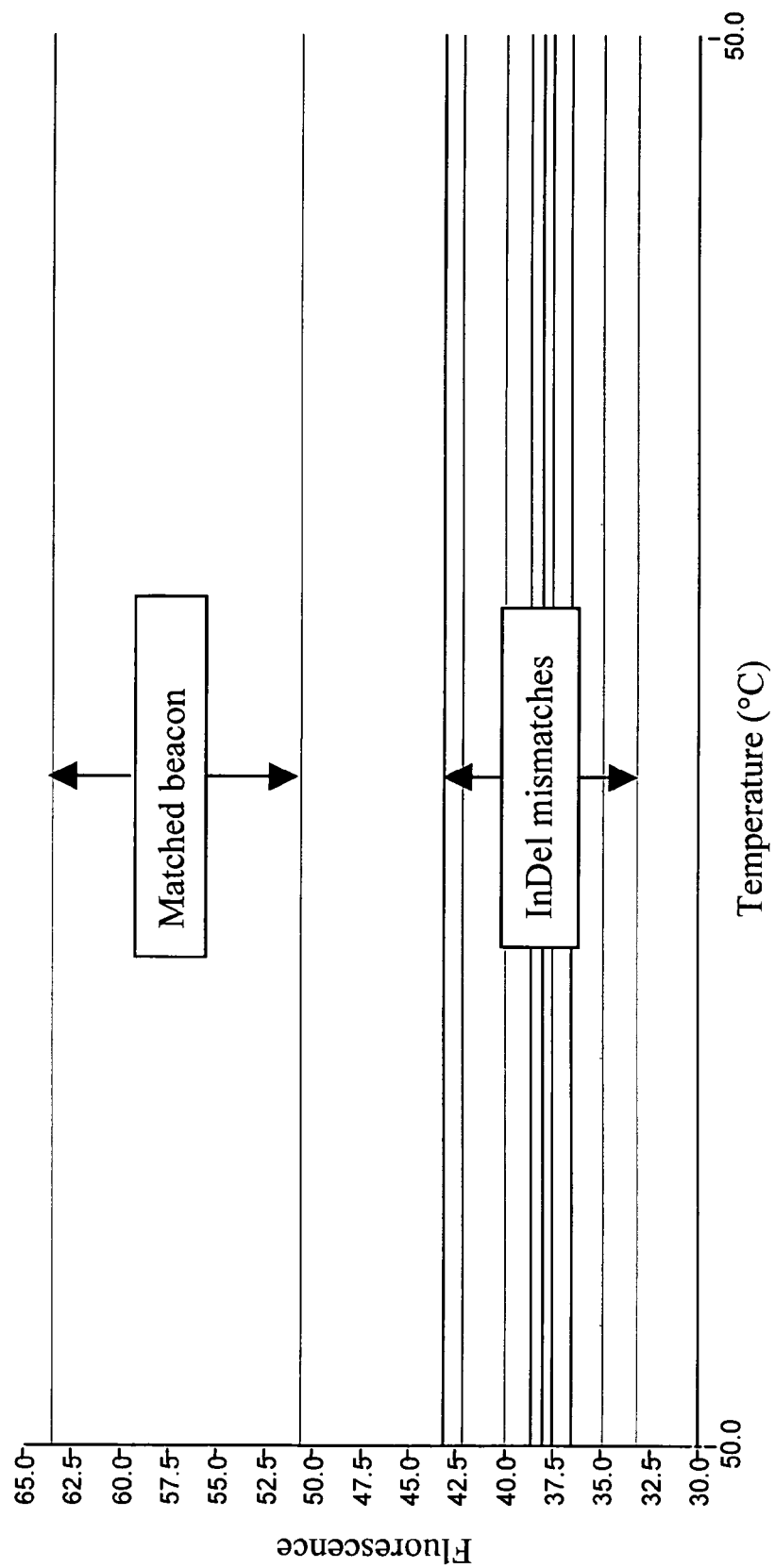

1)

2)

4)

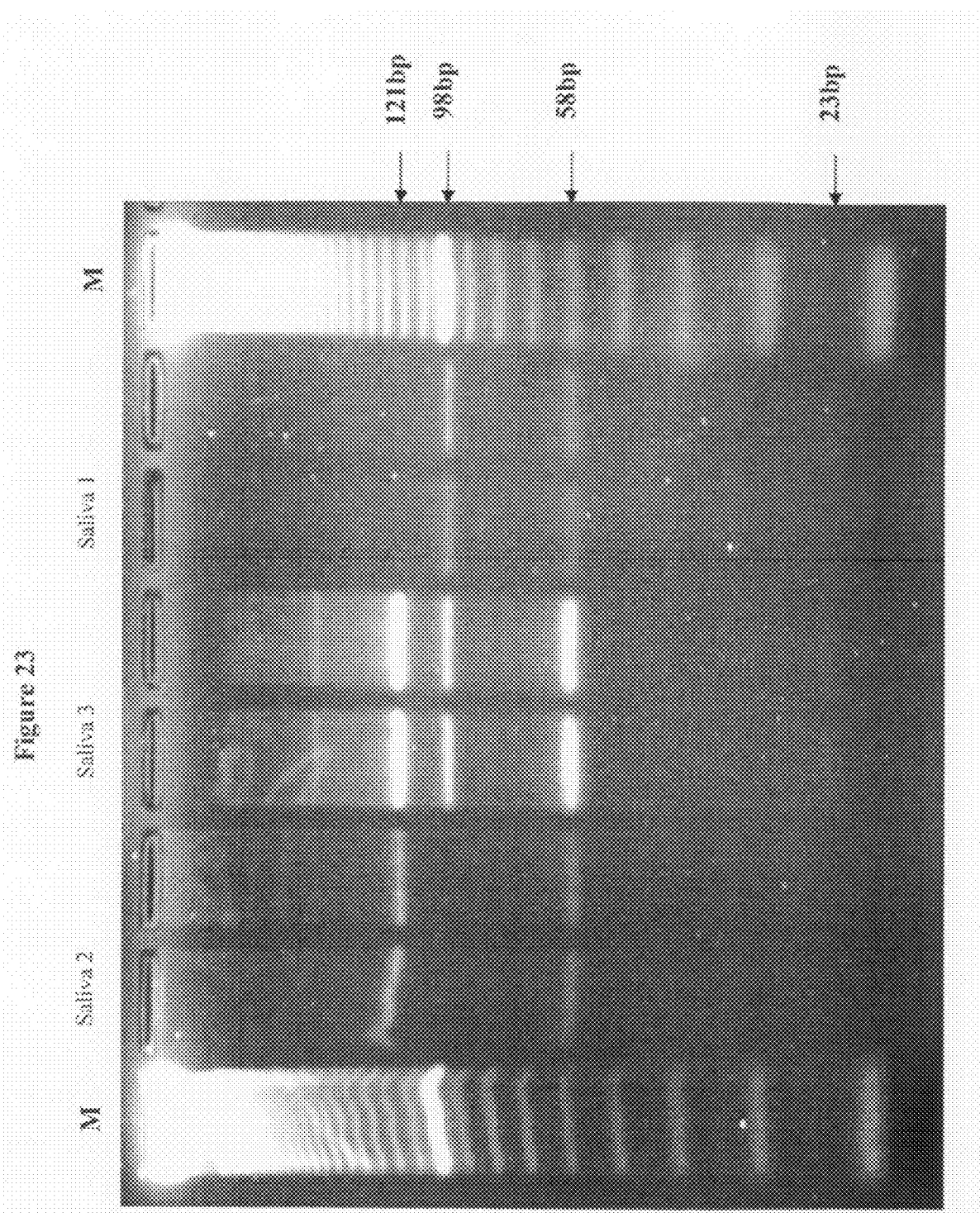

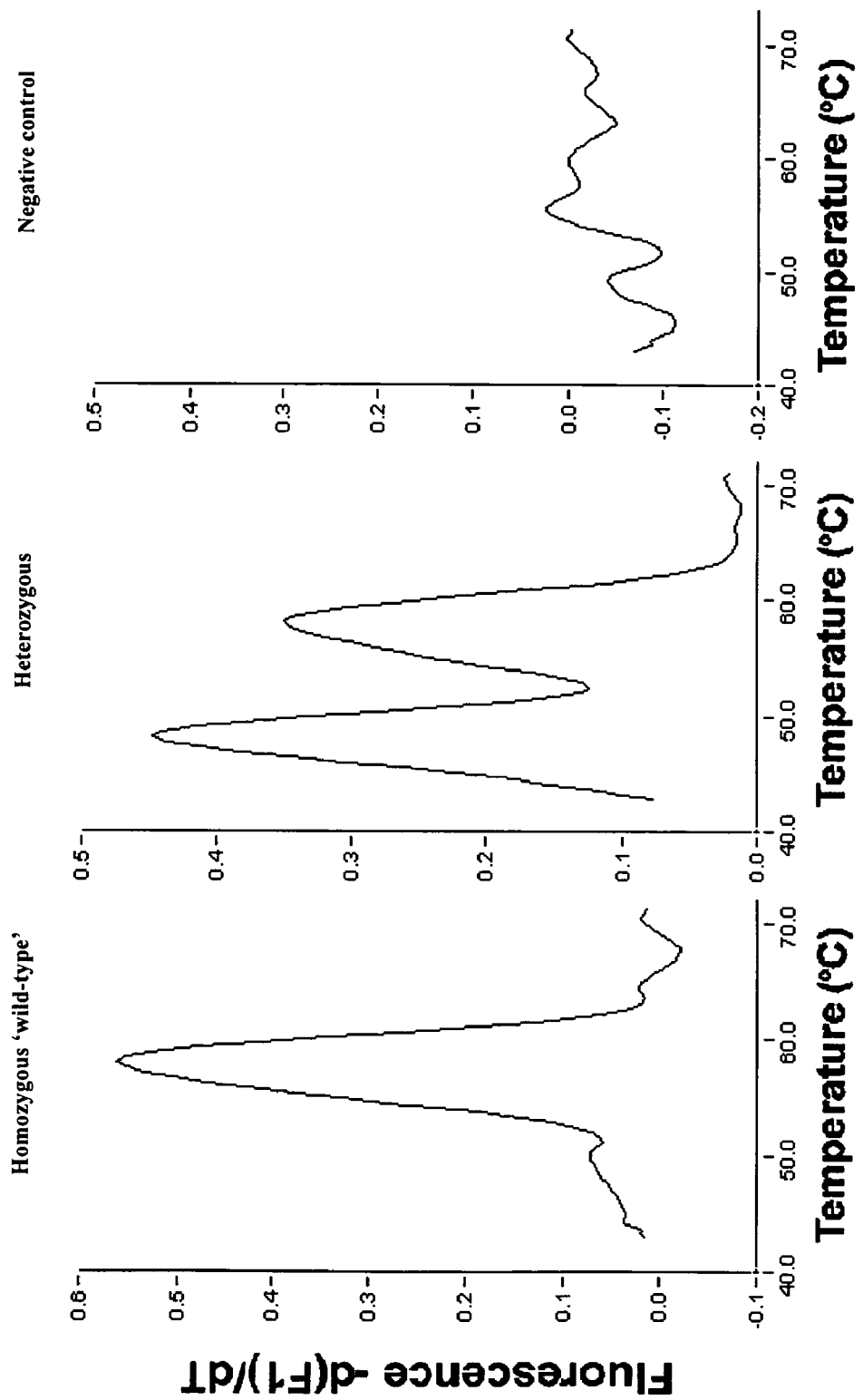

HYBRIDISATION BEACON AND METHOD OF RAPID SEQUENCE DETECTION AND DISCRIMINATION

This application is a continuation-in-part of application Ser. No. 10/239,913, filed Jan. 3, 2003, now U.S. Pat. No. 7,348,141, which is a U.S. national stage of PCT/GB01/01430, filed Mar. 28, 2001.

INTRODUCTION

A multitude of techniques for detecting specific DNA sequences and scoring known single nucleotide polymorphisms have been described. Several of these detection methods utilise hybridisation of fluorescently labelled probes and rely on the transfer of energy between donor and acceptor moieties. This invention embodies a new and simple fluorescent hybridisation probe detection system that does not rely on probe secondary structure or enzyme action. Interaction between these hybridisation probes and their target sequences generates significant alterations in fluorescence emission. Variations in hybridisation potential allow discrimination of polymorphic targets by the amount of fluorescence emission and the melting temperature of the probe/target duplexes. Single Nucleotide Polymorphisms (SNPs) are the most abundant form of sequence variation in the human genome, occurring on average every thousand nucleotides. A SNP is a site within the DNA sequence that varies by a single base (substitution, insertion or deletion) from person to person. These SNPs may affect phenotypic characteristics directly, such as certain diseases, and are commonly employed as genetic markers to identify complex traits, such as response to medication (Pharmacogenetics). SNPs are extremely useful as genetic markers because they evolve slowly and are scored readily by a number of methods. Large-scale efforts are in progress to discover novel SNPs, for use in association studies that may allow identification of genes that contribute to common genetic disorders. Furthermore, many techniques have been developed to efficiently screen for known SNPs with a relatively high throughput. Current methods for SNP genotyping include restriction fragment length polymorphism (RFLP) analysis of polymerase chain reaction products (using gel electrophoresis for restriction fragment detection), allele-specific oligonucleotide (ASO) hybridisation, amplification refractory mutation system (ARMS), oligonucleotide ligation assay (OLA), single-strand conformation polymorphism (SSCP) analysis, chemical cleavage, heteroduplex analysis, mini-sequencing and a variety of probe based systems. Examples of probe based technologies include, molecular beacons, the 5'-exonuclease assay, hybridisation probes and Scorpion primers. Several of these probe systems rely on the transfer of energy between donor (e.g. fluorophore) and acceptor (e.g. quencher) moieties. Fluorescent probes are typically single-stranded oligonucleotides that exhibit lower amounts of fluorescence emission in isolation than when hybridised to target sequences. The structures of these probes convey high specificity, permitting the identification of targets that differ by as little as a single nucleotide.

The energy absorbed by a fluorophore may be transferred to a quencher and released as heat. Quenching of fluorescent signal may occur by Fluorescence Resonance Energy Transfer (FRET) or non-FRET mechanisms. FRET quenching requires a spectral overlap between the donor and acceptor, where the efficiency of quenching is related to the distance between the two moieties. Non-FRET quenching occurs through short-range 'contacts' between fluorophore and quencher, requiring no spectral overlap between moieties.

The 5'-exonuclease (TaqMan™) assay uses FRET quenching to analyse Polymerase Chain Reaction (PCR) amplified target DNA. TaqMan probes are oligonucleotides that contain fluorophore and quencher moieties preferably located on 5' and 3' termini. Very little fluorescence is emitted from intact probe due to efficient intra-molecular quenching. However, during PCR amplification, the probe specifically hybridises to its target sequence and the 5'-3'-exonuclease activity of Taq polymerase cleaves the probe between fluorophore and quencher moieties. Enzymatic cleavage of TaqMan™ probes spatially separates fluorophore and quencher components, causing significant increases in fluorescence emission correlated with target amplification. Careful design of TaqMan™ probes allows discrimination of polymorphic targets, where only perfectly matched probes are degraded to generate increases in fluorescence signal. Since TaqMan™ probes are digested during real-time PCR amplification, probes are not available for post-amplification melting curve analysis.

Molecular beacons are single-stranded oligonucleotide probes that are non-fluorescent in isolation, but become fluorescent upon hybridisation to target sequences. Non-hybridised molecular beacons form stem-loop structures, possessing a fluorophore covalently linked to one end of the molecule and a quencher linked to the other, such that the hairpin of the beacon places the fluorophore moiety in close proximity with the quencher. When molecular beacons hybridise to target sequences, fluorophore and quencher moieties become spatially separated, such that the fluorophore is no longer quenched and the molecular beacon fluoresces. Molecular beacons may be employed in end-point and 'real-time' assays for sequence detection and SNP discrimination. The secondary structure of the molecular beacon conveys high specificity to the hybridisation probe, allowing the identification of targets that differ by a single nucleotide. However, the molecular beacon's intra-molecular interaction potentially produces a source of competition for inter-molecular target hybridisation and, because the molecular beacon is an internal probe, it must compete with the amplicon's opposite strand for binding to the target sequence. The combination of both forms of competition may reduce molecular beacon hybridisation efficiency to some target molecules.

Hybridisation probes are oligonucleotides that are singly labelled with a fluorophore moiety. Two such oligonucleotides are required for each hybridisation probe assay, one labelled with a donor fluorophore and the other with an acceptor fluorophore. Fluorescein is commonly employed as the donor and Cy5, LC-RED 640 and LC-RED 705 are commonly used as acceptors. Excitation of the donor fluorophore produces an emission spectrum that overlaps with the absorption spectrum of the acceptor fluorophore. Hybridisation probe pairs are designed to recognise adjacent nucleotide sequences within target molecules. In isolation, the acceptor oligonucleotide is not excited and does not generate a fluorescent signal. However, during hybridisation to polynucleotide target sequences, the donor and acceptor probes are brought into close proximity, allowing fluorescence resonance energy transfer from the donor to the acceptor. Fluorescent signal from the acceptor fluorophore is only emitted when both probes are hybridised to the target molecule. When incorporated into PCR reactions, fluorescence from the acceptor probe is monitored once per cycle of amplification, to facilitate real-time measurement of product accumulation, where the amount of fluorescence emitted by the acceptor is proportional to the quantity of target synthesised. Careful design of probes and assay conditions permits discrimination of closely related targets by real-time PCR. Furthermore, pairs of hybridisation probes may be employed to discriminate alleles by melt peak analysis and Tm determination. Homozygous samples may be identified by the generation of specific melt peaks during melting curve analysis and heterozygous samples may be identified by the presence of two peaks within a single melting trace.

5'-exonuclease, molecular beacon and hybridisation probe assays are bimolecular systems that have the probe and target sequences located on separate DNA strands. Scorpion probes operate through unimolecular binding events, where the probe and amplified target sequence are located on the same DNA strand. Unimolecular binding events are kinetically favoured over bimolecular hybridisation. Scorpion probes comprise a primer with an attached probe tail sequence, where the probe sequence is contained within a stem-loop secondary structure similar to that of a molecular beacon. In the unextended form, Scorpion primers are non-fluorescent due to fluorophore and quencher moieties being in close proximity. During PCR, the primer component of the Scorpion is extended at its 3' end producing the homologous target sequence required for probe hybridisation. When the Scorpion probe sequence hybridises to amplified target the fluorophore and quencher moieties become spatially separated generating significant increases in fluorescent signal concurrent with target amplification. Careful design of probes and assay conditions permits discrimination of polymorphic targets, where only perfectly matched targets produce increases in fluorescence signal during real-time PCR analysis.

TaqMan probes, molecular beacons, hybridisation probes and Scorpion primers utilise FRET to detect and discriminate polynucleotide sequences. However, the alternative light-up probe system does not require FRET transfer between donor and acceptor moieties to detect and discriminate DNA sequences. These light-up probes comprise a sequence recognising oligonucleotide and a single fluorescent reporter group, where the reporter is typically a derivative of the asymmetric cyanine dye thiazole orange. The fluorescent dye component of light-up probes is attached to the terminus of the oligonucleotide molecule. When single-stranded, probes emit significantly lower quantities of fluorescence than when hybridised to complementary nucleic acid sequences. By measuring the quantity of fluorescence emission, light-up probes may be employed to detect nucleic acid sequences and differentiate between targets differing by a single position.

Homogeneous assays, that perform target DNA amplification and sequence detection/discrimination in a single tube, have been described for molecular beacons, TaqMan probes (5' exonuclease assay), FRET probes and Scorpion primers. Homogeneous methods of analysis eliminate the requirement for downstream analysis (e.g. PCR product purification, enzyme digestion, gel analysis etc) to generate results and reduce the potential for cross-contamination between reactions.

THE INVENTION

In one aspect the invention provides a hybridisation beacon (HyBeacon) which is an oligonucleotide possessing substantially no secondary structure and formed of nucleotide residues of which one is labelled with a reporter and another is optionally labelled with a quencher, with preferably between 1-15 nucleotide residues between the reporter-labelled nucleotide residue and the quencher-labelled nucleotide residue. Hybridisation beacons possessing both fluorophore and quencher moieties are termed F-Q HyBeacons, whereas, probes that possess a reporter component, such as a fluorophore, but lack a quencher moiety are termed F HyBeacons.

The hybridisation beacon of the invention is a linear single-stranded oligonucleotide possessing substantially no secondary structure. Secondary structure arises when one region of an oligonucleotide hybridises with another e.g. forming a loop (as in conventional molecular beacons) which decreases the efficiency of the oligonucleotide hybridising with its complementary target. In the HyBeacons of this invention there is substantially no tendency for one region of the oligonucleotide to hybridise with another.

The length of the HyBeacon is such that it is suitable for hybridising with a complementary polynucleotide target, to provide a stable hybrid whose melting temperature depends on the exact sequence of the target. Oligonucleotides containing less than 15 nucleotide residues in certain cases do not form sufficiently stable hybrids, particularly where the two hybridising sequences are not precisely complementary. Oligonucleotides which are longer than about 30 nucleotide residues in certain cases form hybrids whose melting temperature is relatively insensitive to the possible presence of a single nucleotide mismatch. Nucleotide residues are usually derived from the naturally occurring nucleosides A, C, G and T. However nucleotide analogues may be used at one or more locations of the hybridisation beacon, such nucleotide analogues being modified e.g. in the base portion and/or the sugar portion and/or the triphosphate link. Base modifications, such as propynyl dU (dT-analogue) and 2-amino dA (dA analogue), generally alter the hybridisation properties and may make the use of oligonucleotides having less than 15 or more than 30 nucleotide residues attractive. Alternatively, oligonucleotides composed of or comprising peptide nucleic acid (PNA), locked nucleic acid (LNA), 2'-O-methyl RNA, phosphoramidate DNA, phosphorothioate DNA, methyl phosphonate DNA, phosphotriester DNA or DNA base analogues may be employed to form more stable interactions with target sequences.

Both F and F-Q HyBeacons have been demonstrated to emit significantly greater amounts of fluorescence when hybridised to complementary nucleic acid sequences than when in the single-stranded conformation. An unexpected finding was that F HyBeacons emit significantly more fluorescent signal when double-stranded than when in the single-stranded state despite the absence of a quencher component.

This is a significant finding in that it allows probe assays to be designed that do not require associated acceptor probes or energy transfer between probes as is required with known hybridisation probes. For the purposes of this specification, such assays are termed "single probe assays".

Fluorophore-quencher systems are well described in the literature and will not be further described here. The preparation of oligonucleotides containing fluorophore-labelled nucleotide residues and quencher-labelled nucleotide residues is also well described in the literature.

The signal ratio is the ratio of the signal intensity of a double-stranded hybrid comprising a hybridisation beacon to the signal intensity of the single-stranded probe and is preferably as large as possible, e.g. 3 or more. This signal ratio is dependent upon multiple factors. For F-Q HyBeacons, the rate of energy transfer from an exited donor molecule (fluorophore) to a nearby acceptor molecule (quencher) depends, not only on the distance between the two moieties, but also on their relative angular disposition. HyBeacons with fluorophore and quencher moieties separated by as little as 1 or 3 nucleotide residues possess fluorescence signal ratios that are significantly and usefully greater than 1. HyBeacons possessing more than 3 nucleotides separating fluorophore and quencher exhibit larger signal ratios. For F-Q HyBeacons, fluorophore and quencher components are preferably positioned such that 5 or more nucleotide residues separate the two moieties. Donor and acceptor molecules separated by less than 5 nucleotides may make 'contact', permitting possible non-FRET interactions.

F HyBeacons have been demonstrated to exhibit comparable signal ratios to F-Q HyBeacons that possess more than 5 nucleotides separating the donor and acceptor components. Signal ratios in F HyBeacons are significantly and usefully greater than 1 despite the absence of quencher moieties. The absence of acceptor molecules causes F HyBeacons not to be influenced by angular disposition affects, such that the relative distance between fluorophore and quencher molecules cannot determine the amount of fluorescent signal emitted in double-stranded and single-stranded states. It is believed that fluorophore moieties emit significantly more fluorescent signal when HyBeacon probes are hybridised to target molecules than when the probes are in the single-stranded form possibly due to some form of interaction with duplex DNA.

In certain case, it may be appropriate to include more than one reporter in the oligonucleotide.

In a hybridisation beacon according to the invention, the oligonucleotide preferably has a sequence fully complementary to one allele of a known polynucleotide target having a known polymorphism, e.g. a point mutation or a single base insertion or deletion (SNP). In F-Q HyBeacons, this SNP of the target is preferably, though not essentially, complementary to a nucleotide residue of the hybridisation beacon intermediate between the fluorophore-labelled nucleotide residue and the quencher-labelled nucleotide residue. For F HyBeacons, the site of polymorphism is preferably, though not essentially, located centrally within the oligonucleotide probe.

Alternatively, the hybridisation beacon may be complementary to a known non-polymorphic polynucleotide target and may simply be used to detect that target. Also, the hybridisation beacons may be used to study potentially polymorphic targets with unknown and uncharacterised polymorphisms. The possibility is envisaged of mapping the position and/or nature of unknown polymorphisms by differential beacon hybridisation and differences in melt peak Tm.

The fluorophore-labelled nucleotide residue and/or quencher-labelled nucleotide residues are preferably positioned internally within the oligonucleotide sequence, rather than at the 5'-end or the 3'-end. When the hybridisation beacon is caused to hybridise with a polynucleotide target, all these features contribute to the formation of a stable hybrid with a optimal melting temperature and a substantial difference in melting temperatures between strands which are perfectly matched and strands which have a single or multiple positions of mismatch ($\Delta$Tm).

It may be convenient to provide two or more hybridisation beacons, one fully complementary to each allele of the SNP under investigation. Where each hybridisation beacon carries a different fluorophore, it may be convenient to mix the probes in solution for analysis of homozygous and heterozygous targets. In the same way, a mixture of hybridisation beacons complementary to the various alleles of several different SNPs may be used together in solution for multiplex analysis, provided that each is labelled with a spectrally distinct fluorophore.

Alternatively, a hybridisation beacon of this invention may be provided immobilised on or within a support. Techniques and linkers for immobilising oligonucleotides using supports in forms that leave them free to hybridise with complementary targets in solution are well described in the literature.

Also included within the scope of the invention is an array of oligonucleotide probes immobilised at spaced locations using a support, wherein different oligonucleotide probes are different hybridisation beacons according to this invention. Furthermore, HyBeacon probes may be employed to analyse DNA targets immobilised on or within a support, where distinct targets may be positioned at spaced locations on array type formats.

In another aspect, this invention provides a method of investigating a polynucleotide target which optionally has a known or suspected polymorphism, which method comprises providing an oligonucleotide probe comprising a fluorophore-labelled nucleotide residue and, optionally, a quencher-labelled nucleotide residue. The polynucleotide target is incubated with the oligonucleotide probe to form a hybrid, the oligonucleotide probe exhibiting a higher level of fluorescence when in the form of the hybrid than when in single-stranded form. The level of fluorescence emitted by the oligonucleotide probe is observed at a predetermined temperature, or monitored over a range of temperatures. Preferably the oligonucleotide probe is a hybridisation beacon as herein defined. In a preferred embodiment of the invention, the method utilises a single type of hybridisation beacon according to the invention without an associated quencher, and without a further probe carrying an acceptor moiety.

The polynucleotide target may be DNA, RNA or cDNA, and is used in single-stranded form, or a DNA duplex may be probed to form a triplex. The polynucleotide target has a known polymorphism, preferably a SNP. The target is incubated under hybridising conditions with an oligonucleotide probe, which may be a hybridisation beacon as herein described. It is necessary that the hybrid generate a stronger fluorescence signal than the single-stranded oligonucleotide probe. The melting temperature of the hybrid will depend, amongst other things, on whether the polynucleotide target and oligonucleotide probe are fully complementary or whether there is a single or even a double mismatch arising at or close to the location of the SNP. The method involves observing the level of fluorescence signal, emitted by the oligonucleotide probe, at a predetermined temperature near the melting temperature of the hybrid, or over a range of temperatures. Two alternatives are described, although others are possible:— a) The temperature of a solution containing the hybrid is slowly raised, while continuously observing a fluorescence signal, in order to construct a graph of negative derivative of fluorescence signal intensity with respect to temperature (−dF/dT) against temperature. The melting temperature (Tm) of the hybrid appears as a peak, and provides information about the sequence of the polynucleotide target. The Tms generated through HyBeacon melting analysis may be used to distinguish polymorphic targets. The range of temperature chosen generally encompasses the melting temperature of the hybrid.

b) A solution of the hybrid is held at a predetermined temperature and the level of fluorescence observed. Generally, the predetermined temperature is chosen to be intermediate between the melting temperature of a perfectly matched hybrid and the melting temperature of a hybrid with one or two mismatches. The level of fluorescence signal observed provides an indication of whether or not the hybrid has melted, and so provides information about the sequence of the polynucleotide target. Polymorphic targets may be distinguished in end-point and real-time or kinetic formats.

Typically, the hybridisation beacon has a sequence complementary, typically fully complementary, to one allele of the target polynucleotide. Use of fully complementary beacons allows differentiation between matched and mismatched hybridisation. Suitably, each of two or more different hybridisation beacons has a sequence complementary, ideally fully complementary, to a different allele of the target polynucleotide.

Conveniently, the polynucleotide target may be a PCR amplimer, formed by using suitable primers to amplify a desired portion of genomic DNA. It may be convenient to perform the amplification and target investigation in a homogenous mode, e.g. in a single reaction vessel by adding the oligonucleotide probe before, during or after the amplification cycling procedure. It may also be convenient to perform target amplification and sequence investigation directly from samples, such as saliva, without prior extraction of DNA, RNA or cDNA. Preferably the oligonucleotide probe is modified at its 3'-end so as to prevent chain extension during PCR amplification.

The melting temperatures of hybridisation beacons may be used to identify polymorphic target polynucleotides. The hybridisation beacons of the invention may also be employed to identify homozygous and heterozygous DNA using a single probe.

The following examples illustrate the invention and are not intended to be limiting in any way.

FIG. 1: Differential HyBeacon Hybridisation. Illustrates the difference between matched, mismatched and double mismatched interactions, where stars represent single nucleotide polymorphisms (SNPs). Type A interactions involve a HyBeacon molecule designed to be perfectly matched to a wild type target or one allele of an SNP. Type B interactions involve a HyBeacon molecule designed to be perfectly matched to a mutant target or the alternate allele of the SNP. When considering two independent SNPs, beacon hybridised to target molecule may be either (i) perfectly matched, (ii) possess a single base mismatch or (iii) possess multiple base mismatches.

Figure 2B:
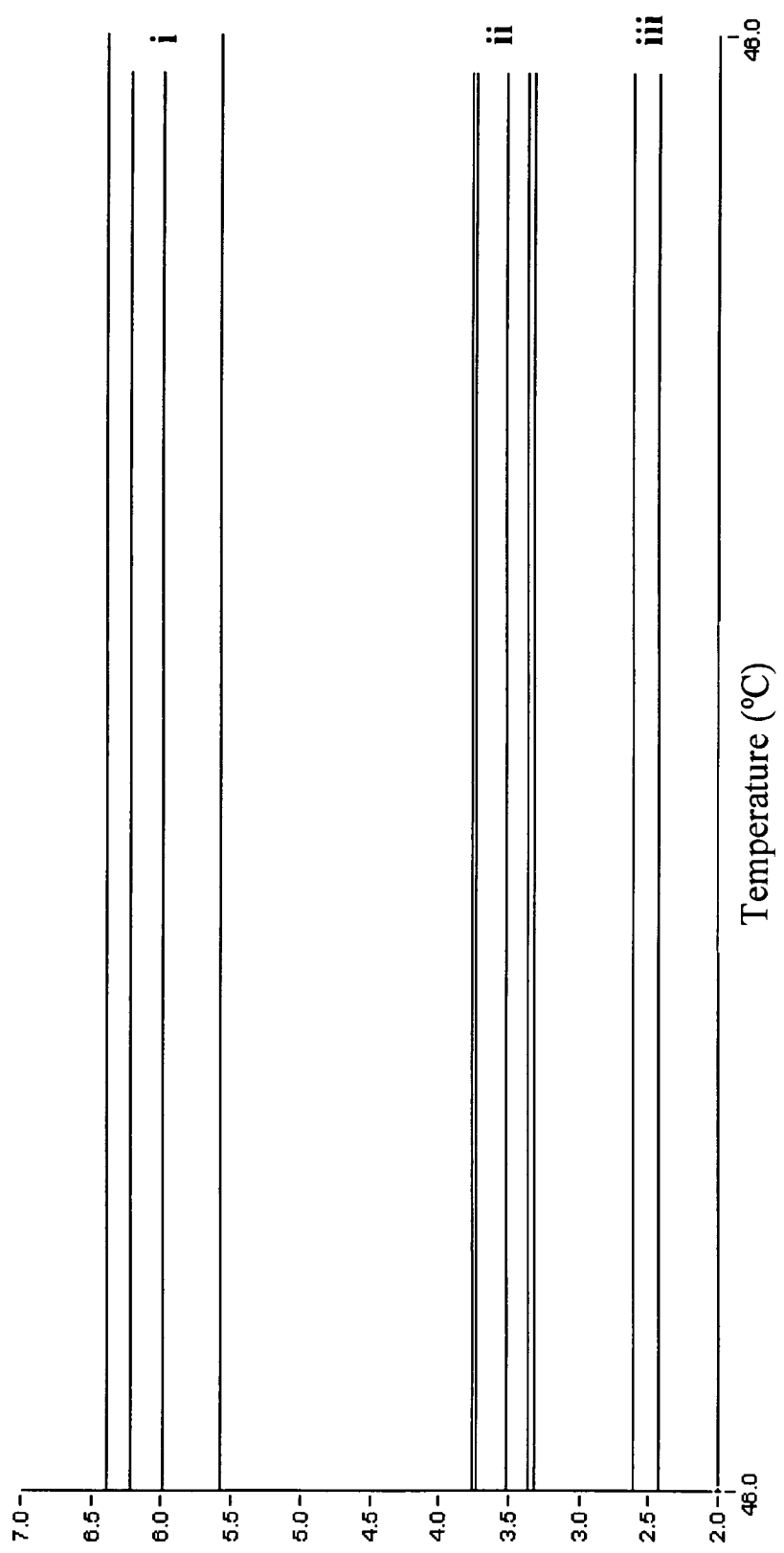

FIG. 2: SNP discrimination using the amount of fluorescence. The B9414 HyBeacon was hybridised to perfectly matched (i) and single base mismatched oligonucleotides (ii) and was also studied in the absence of target (iii). a) Melting profiles derived from the B94141 HyBeacon. At temperatures below 42° C. and above 52° C., the amount of fluorescence emitted by probe hybridised to matched and mismatched targets is very similar. However, between these temperatures the quantity of fluorescence emitted by fully complementary probe is significantly greater than the fluorescence emission of the mismatched HyBeacon. b) Reactions were denatured and rapidly cooled to 46° C. for fluorescence acquisition. Significant clustering within treatments and statistical differences between treatments are observed, such that probe hybridised to a matched target emits significantly more fluorescence than HyBeacon hybridised to a mismatched target, which in turn emits more fluorescence than hybridisation beacon in the absence of target. c) HyBeacon in the absence of target does not generate melting peaks. B9414 produces melting curves possessing Tms of approximately 52° C. and 44° C. in the presence of matched and mismatched targets respectively, allowing reliable discrimination of SNPs.

Figure 3:
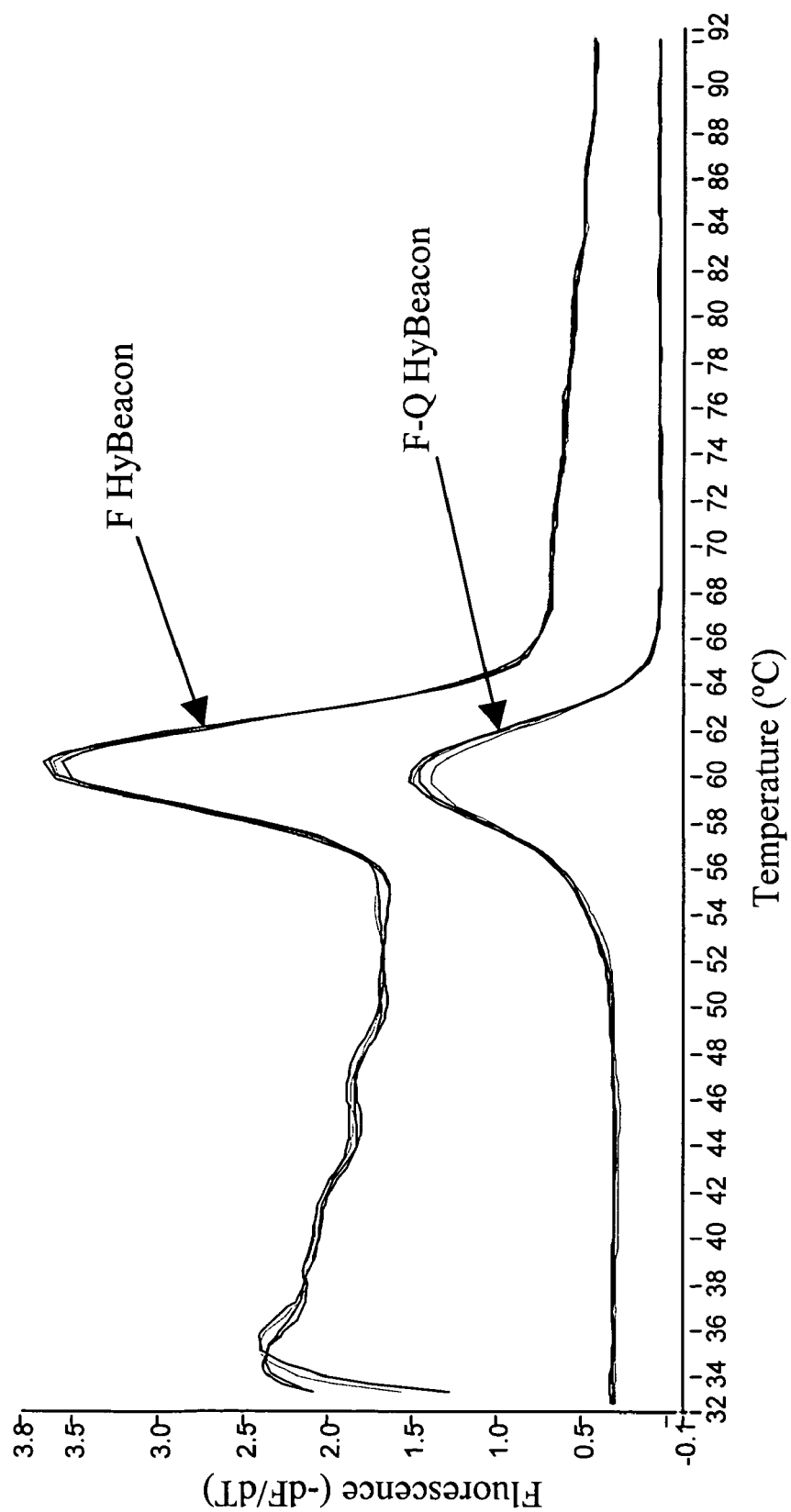

FIG. 3: Comparison of F and F-Q HyBeacon probes. The NAT2 hybridisation beacons F17834 (F-Q) and 0203002 (F) were hybridised to a perfectly matched oligonucleotide. F and F-Q HyBeacons possess identical nucleotide sequence and generate high quality peaks with Tms of approximately 60° C. in melting analyses. Due to the lack of a quencher moiety, F HyBeacons emit larger amounts of background fluorescence compared with F-Q probes.

Figure 4A:
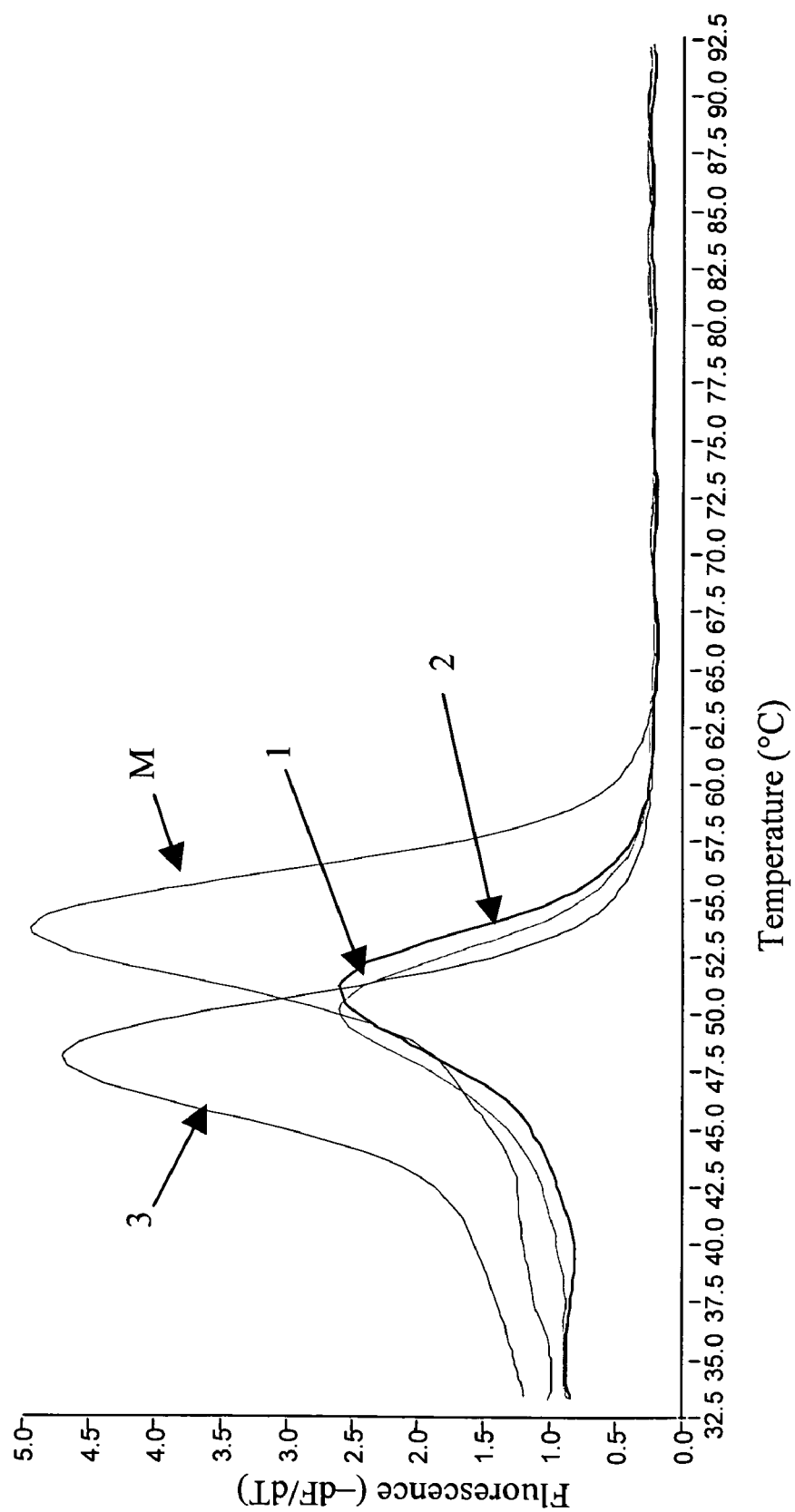
Figure 4B:
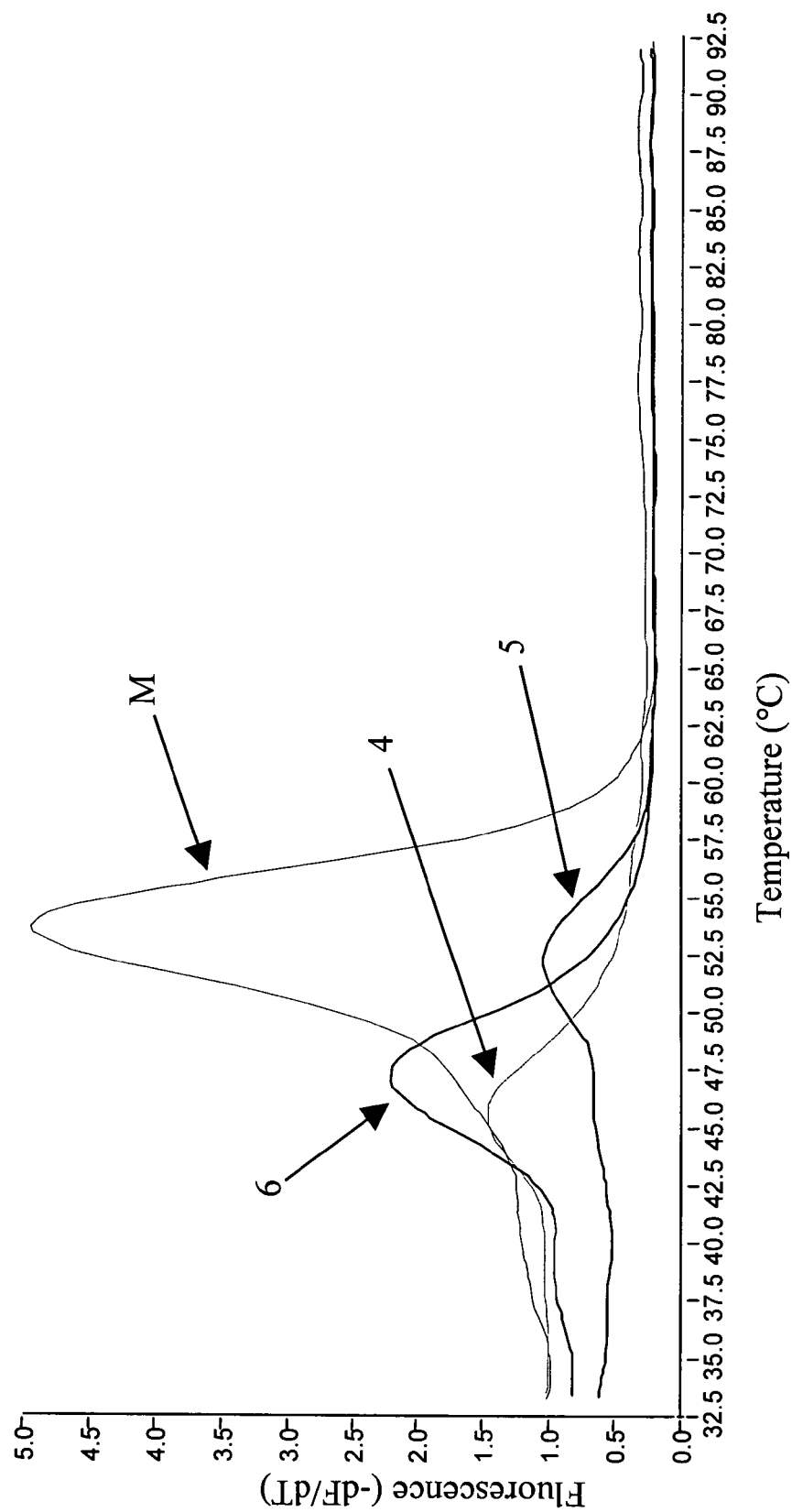

FIG. 4: Melting analysis of InDel polymorphisms. The TB0993 NAT2*4 probe was hybridised to a series of oligonucleotide targets to determine whether hybridisation beacons have the potential to discriminate insertion and deletion polymorphisms. Matched target (M), 3 oligonucleotides containing single nucleotide insertions (1-3) and 3 oligonucleotides containing single nucleotide deletions (4-6) were compared. Melting analysis was performed for each HyBeacon/target duplex. In all cases, matched probe generated melting curves with higher Tms than the mismatched InDel reactions, such that SNPs may be discriminated on the basis of melt peak Tm. a) Insertion Oligonucleotides. b) Deletion oligonucleotides. c) Demonstrates that SNPs may also be discriminated on the basis of amount of fluorescence emission, where matched beacon emits more fluorescence than hybridisation to all InDel mismatches.

Figure 5A:
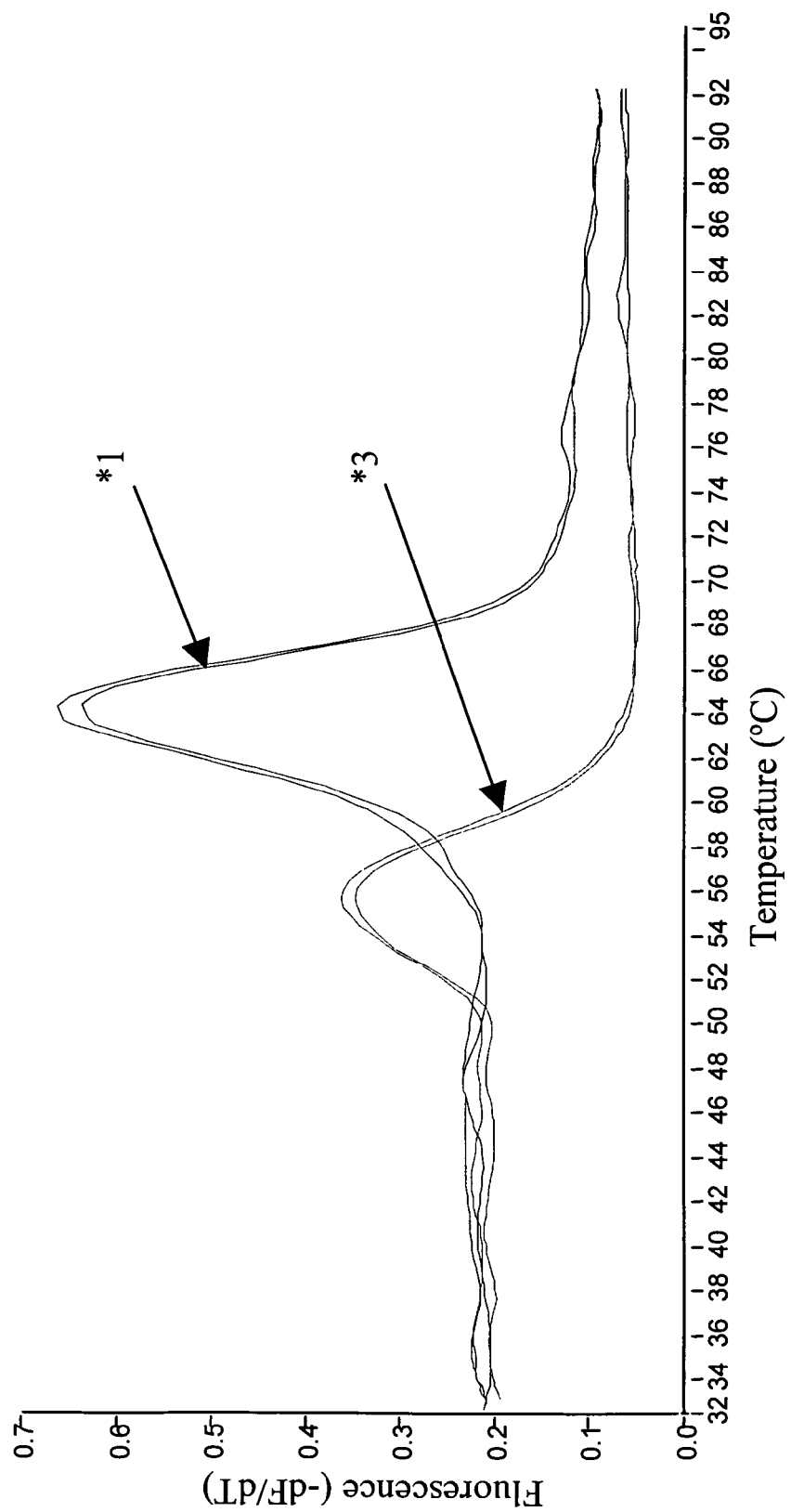
Figure 5B:
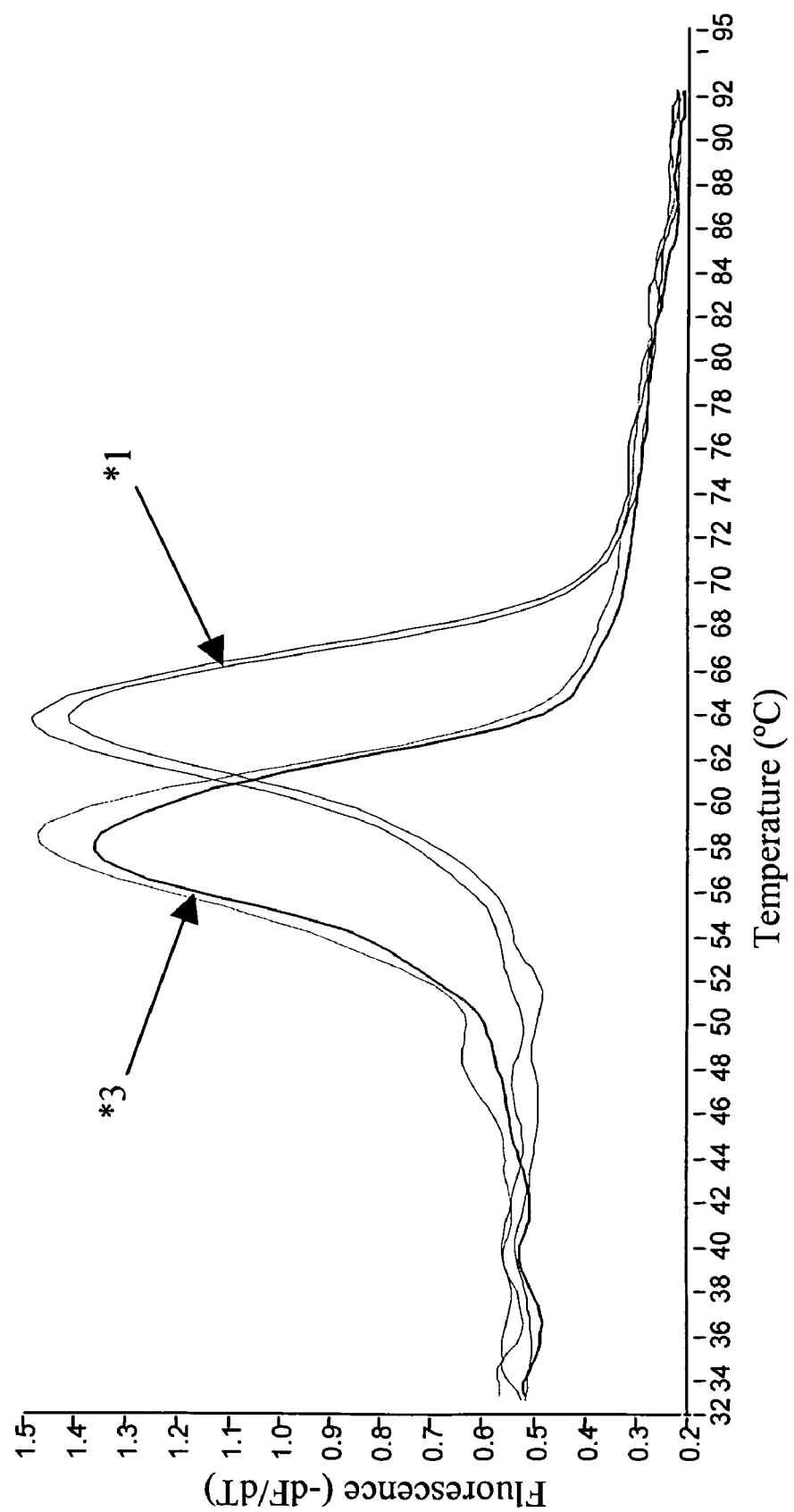

FIG. 5: Discrimination of SNPs in a heterogeneous format. F and F-Q HyBeacon probes were employed to discriminate targets containing the CYP2D6*3 polymorphism, where the DNA targets employed were isolated 119 bp PCR products. F (2D63B) and F-Q (2D63A) probes are identical nucleotide sequences, being perfectly matched to the *1 allele of the CYP2D6 gene and possessing a single base mismatch when hybridised to the *3 allele. a) The 2D63A F-Q probe generates melt peaks with Tms of approximately 65° C. and 56° C. when hybridised to matched and mismatched targets respectively. b) The 2D63B F HyBeacon produces melt peaks with Tms of approximately 65° C. and 58° C. when hybridised to *1 and *3 PCR targets respectively.

Figure 6:
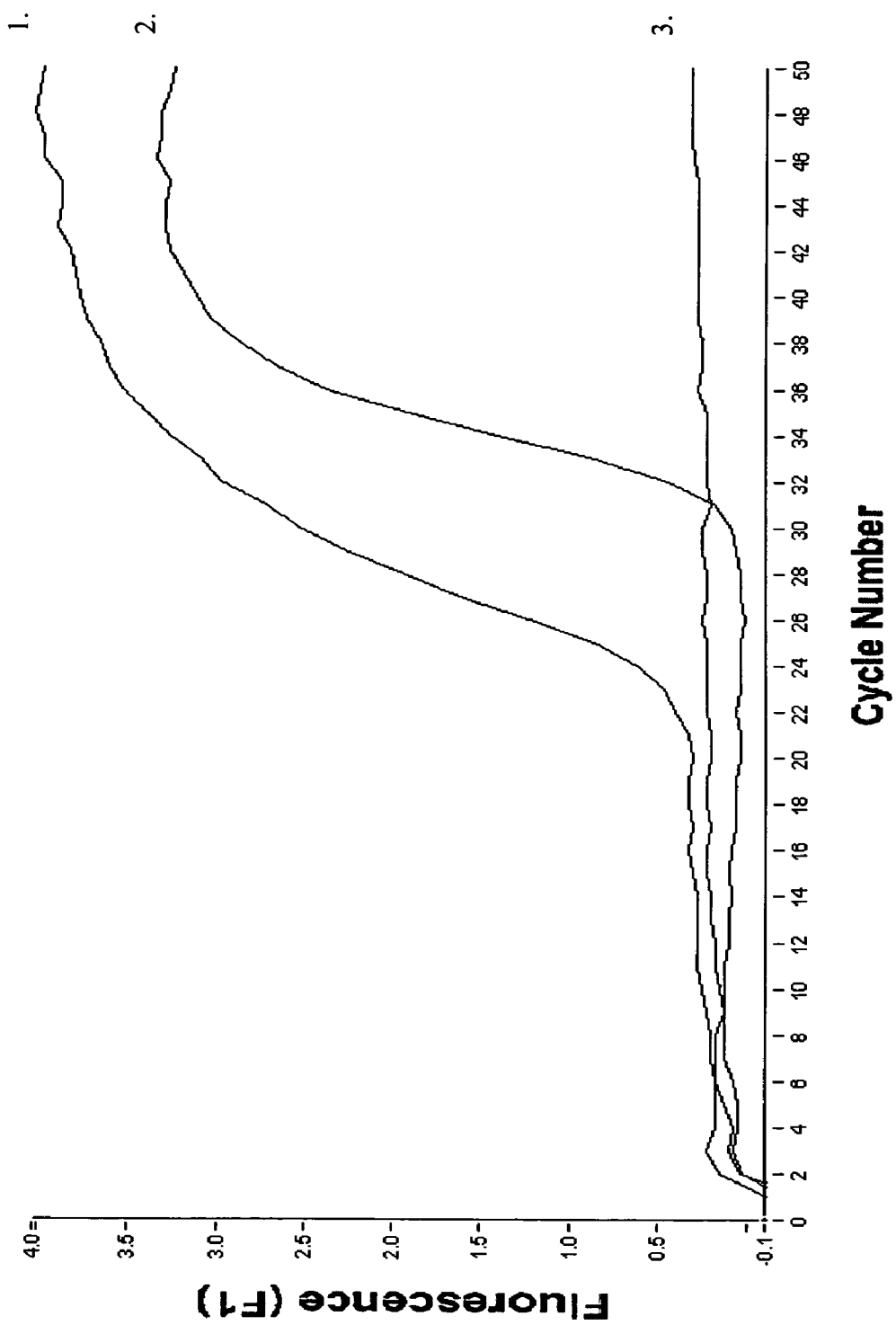

FIG. 6: Homogeneous detection of DNA sequences. Detection of CYP2D6*1 sequence in genomic DNA (1) and saliva (2) samples using the 2D64C*HyBeacon probe to monitor the real-time accumulation of PCR product. The amount of fluorescence emitted from HyBeacon probes is correlated with the amplification of specific target sequences. Control reactions (3) that do not contain template DNA or amplified product also do not display elevated levels of fluorescence emission during PCR.

FIG. 7: Discrimination of SNPs in a homogeneous format. The F HyBeacon probe 0203002, which is perfectly matched to NAT2*4 sequence, was employed to discriminate *4 and *5A SNPs in homogeneous LightCycler assays. a) SNPs were reliably discriminated through 'real-time' PCR amplification, where only reactions containing the matched *4 template produced significant increases in fluorescence emission. b) SNPs were also discriminated post-amplification by melting analysis, where matched *4 alleles generated melt peaks with significantly higher Tms than mismatched *5A target sequences. End-point analysis of amplified products permits validation of 'real-time' data.

Figure 8:
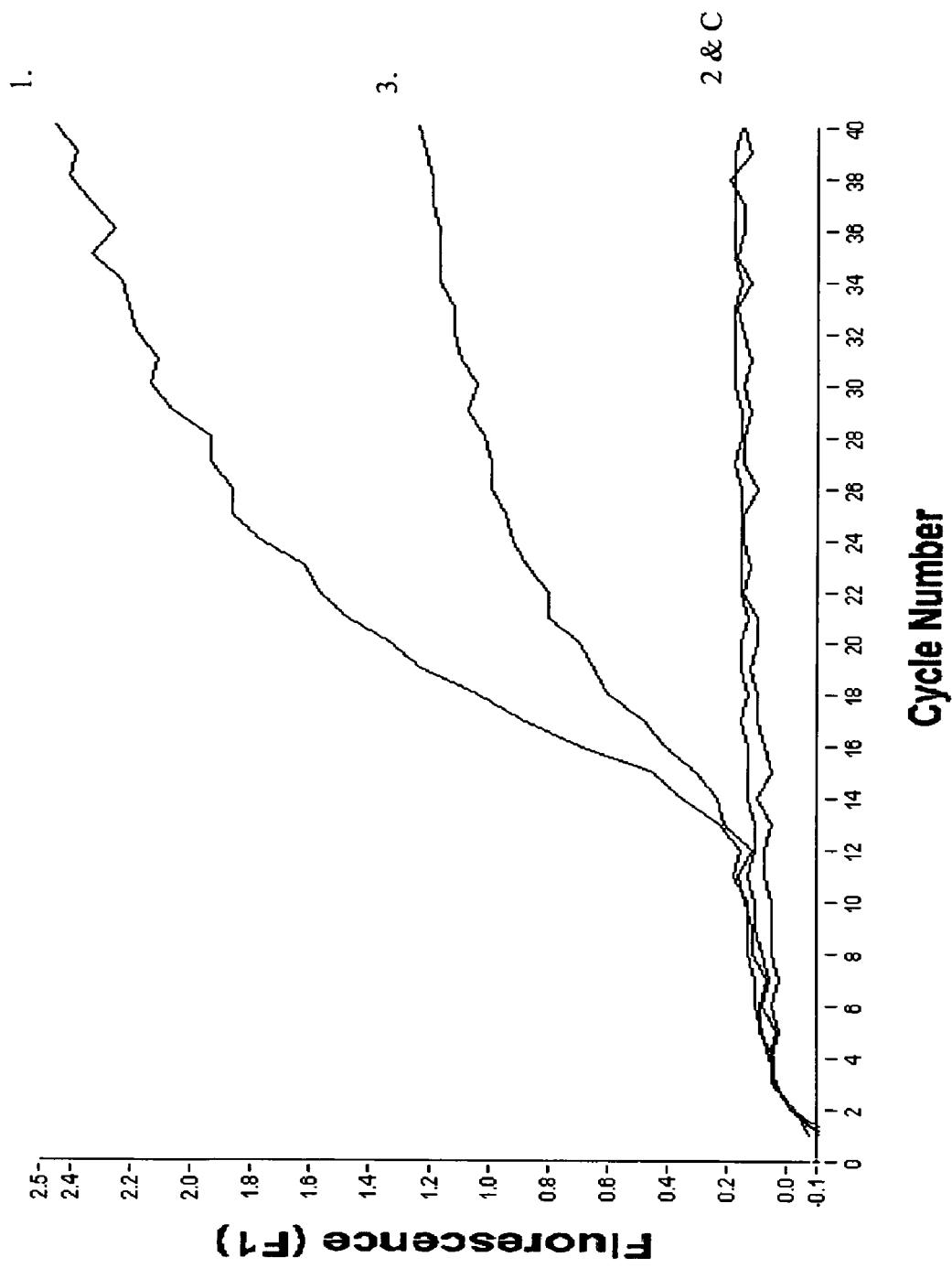

FIG. 8: Real-time discrimination of the CY2D6*4 polymorphism: The 2D64C* HyBeacon was employed to detect and discriminate the *1 and *4 alleles of the CYP2D6 gene. Polymorphic sequences were amplified from pGEM-T plasmids containing the *1 allele (1), and the *4 allele (2). A mixture of *1 and *4 plasmids was employed to simulate heterozygous DNA (3). No template control reactions (C) were also included in the analysis. Only those reactions that contain the *1 allele (i.e. samples 1 & 3) generate increases in fluorescence emission during real-time PCR amplification. Homozygous *4 samples and no template controls do not produce elevated fluorescent signals. Samples that are heterozygous for *1 and *4 alleles cause intermediate quantities of fluorescence to be generated during amplification.

Figure 9:
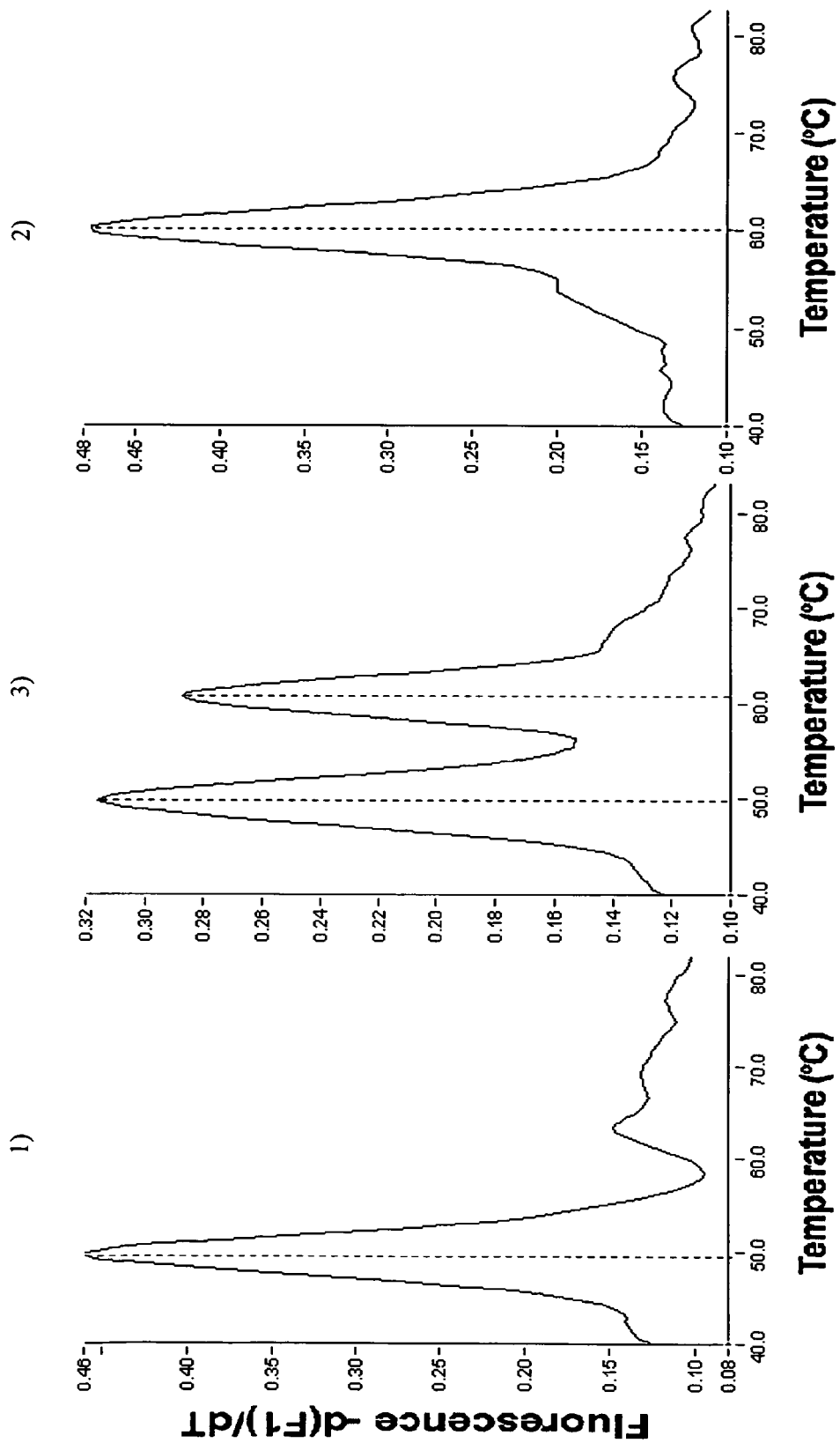

FIG. 9: Discrimination of CYP2D6*1 and *4 alleles by melt peak analysis. Polymorphic targets were amplified from genomic DNA samples and the melt peaks displayed here were derived from post-amplification analysis of samples 1 (homozygous *4), 2 (homozygous *1) and 3 (heterozygous DNA). The 2D64C* HyBeacon is fully complementary to the *1 allele of the CYP2D6 gene and generates single melt peaks possessing Tms of 49° C. and 60° C. with homozygous *4/*4 and *1/*1 samples respectively. Heterozygous samples, possessing both *4 and *1 alleles, generate traces possessing 49° C. and 60° C. melt peaks.

Figure 10A:
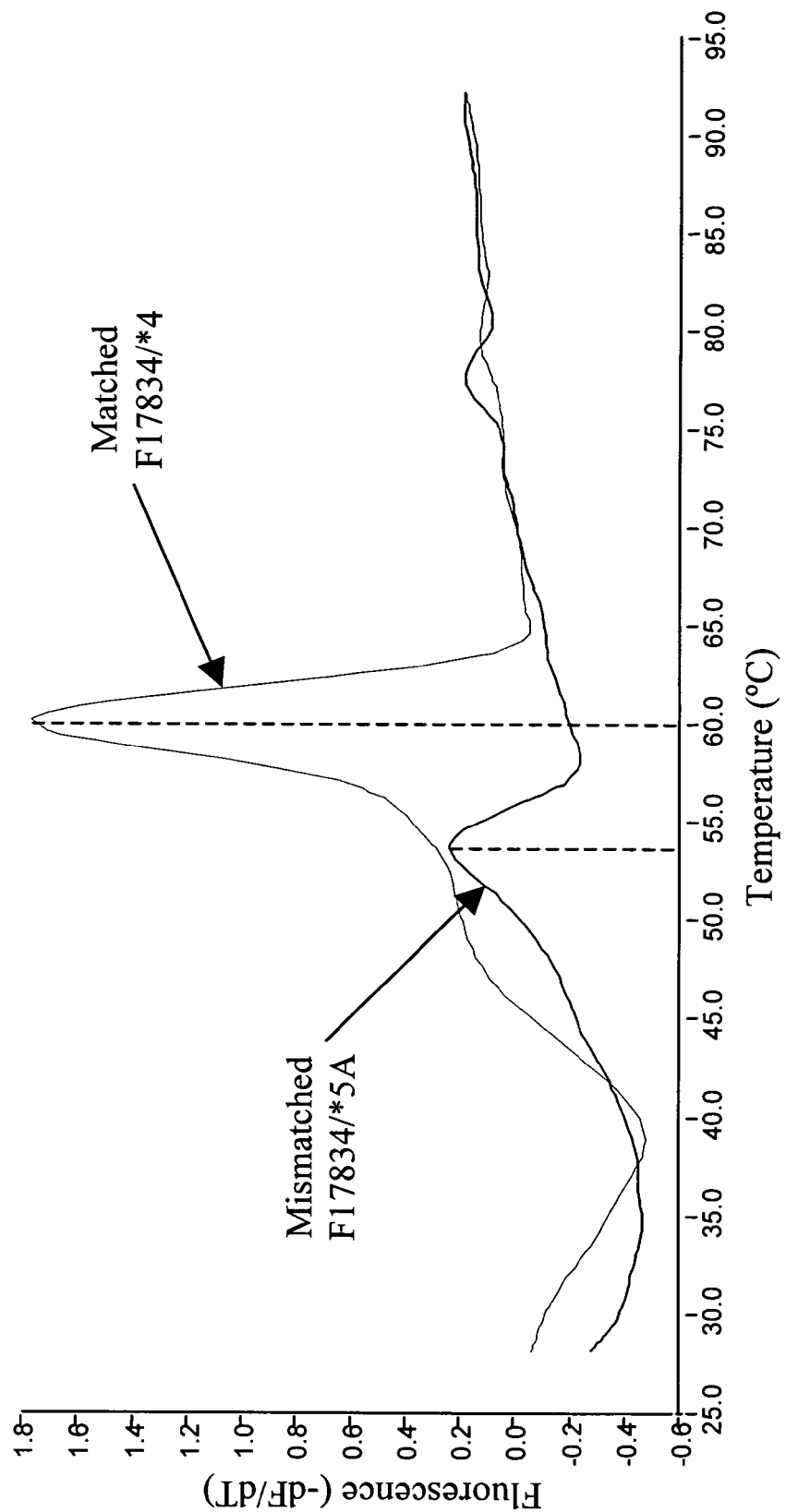
Figure 10B:
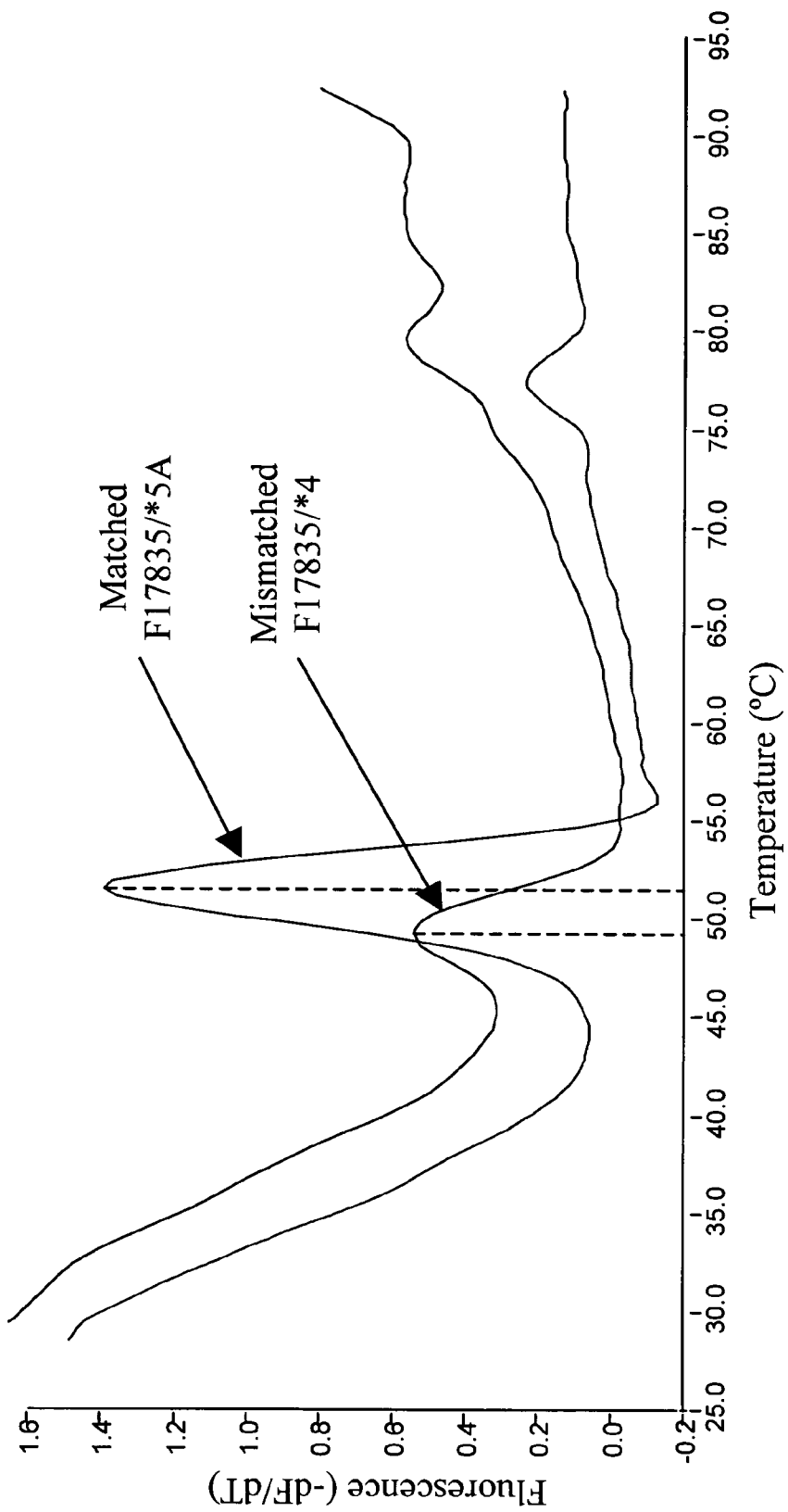
Figure 10C:
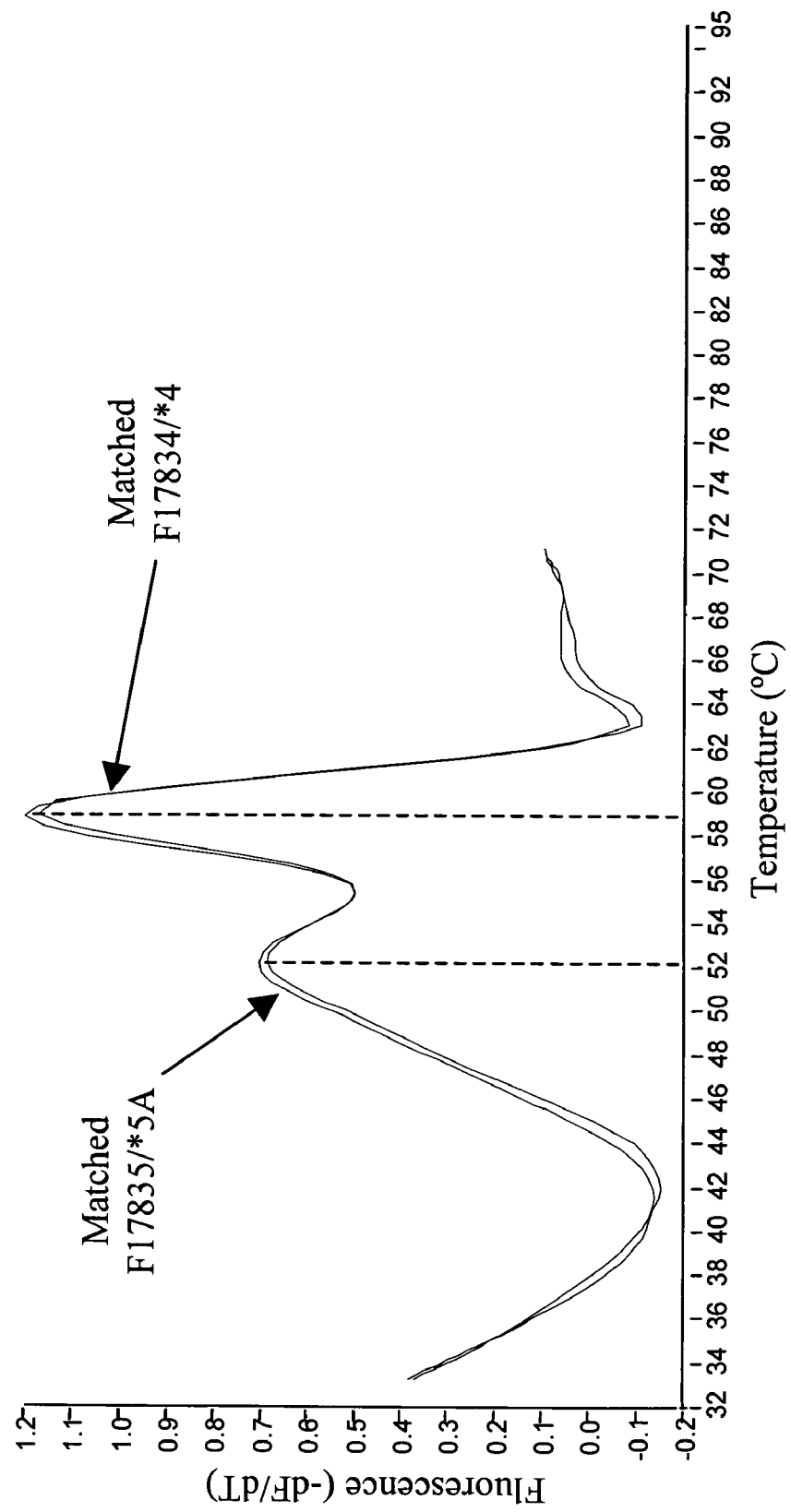

FIG. 10: Identification of heterozygosity using F-Q HyBeacons. Two F-Q HyBeacons, perfectly matched to both alleles of an SNP were required to distinguish homozygous samples (containing only one allele of a polymorphism) from heterozygous samples (containing both alleles). The F17834 and F17835 HyBeacons are perfectly matched to *4 and *5A alleles of the NAT2 gene respectively. F17834 and F17835 possess significantly different Tms to distinguish the two FAM labelled probes. a) F17834 generates melting peaks possessing Tms of approximately 60° C. and 54° C. in the presence of homozygous *4 and *5A alleles respectively. b) F17835 generates melting peaks possessing Tms of approximately 52° C. and 49° C. in the presence of homozygous *5A and *4 alleles respectively. c) Reactions containing F17834 or F17835 HyBeacons produce only matched melting peaks in the presence of heterozygous DNA. Reactions containing both probes produce melting traces possessing Tms of approximately 59° C. and 52° C. in the presence of a mixture *4 and *5A alleles. The presence of two peaks within a single melting trace allows identification of heterozygous samples.

Figure 11A:
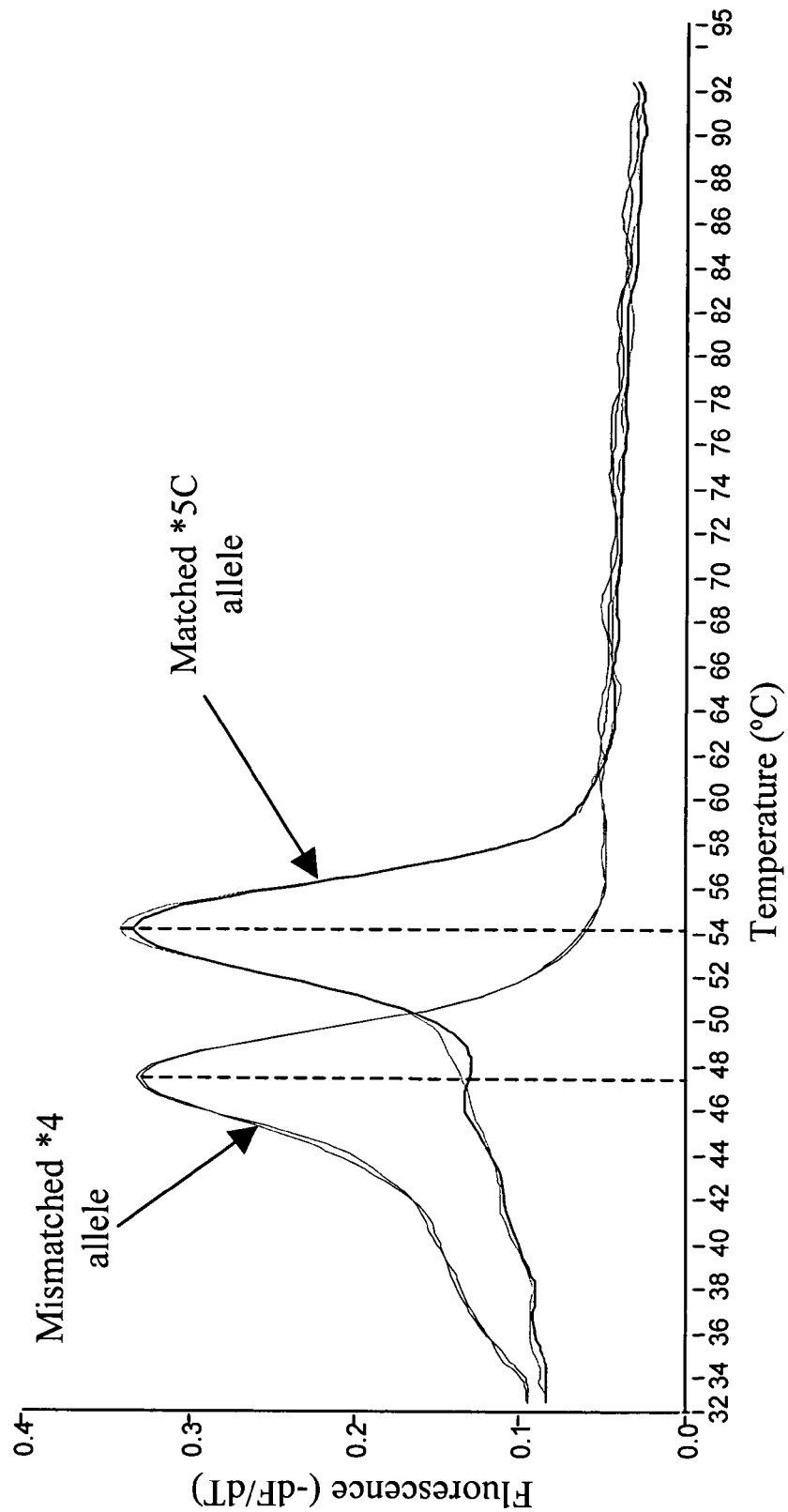
Figure 11B:
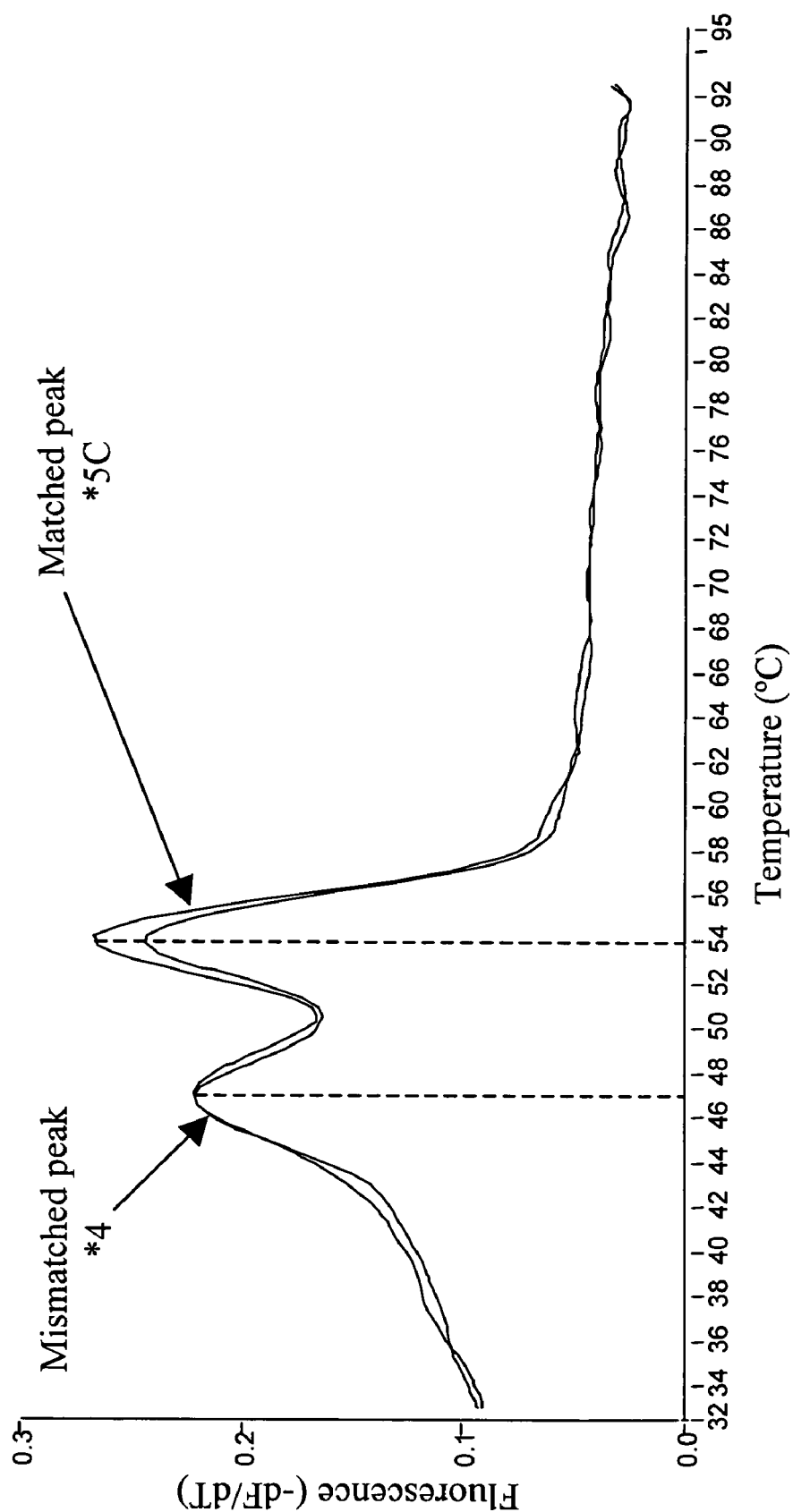

FIG. 11: Analysis of heterozygosity using an F HyBeacon. The HyBeacon DdeFL1, which is perfectly matched to the NAT2*5C polymorphic sequence, was used to test the potential of F HyBeacons to discriminate heterozygous samples. a) Homozygous samples analysed with DdeFL1 generate melting traces possessing a single peak. The DdeFL1 probe was hybridised to homozygous *5C and *4 PCR targets, in heterogeneous assays, generating 54° C. and 47° C. melting curves respectively. b) Reactions containing the DdeFL1 HyBeacon and a mixture of matched and mismatched targets generate curves possessing both the 54° C. and 47° C. peaks in the same melting trace. The presence of two peaks in a melting trace permits identification of heterozygous samples.

FIG. 12: The limitations of HyBeacon multiplex analysis. To examine the potential for HyBeacon multiplex analysis, the 2D64B HyBeacon probe was included in reactions containing both specific and non-specific PCR templates. PCR templates comprised a mixture of specific (CYP2D6) and non-specific (NA T2) DNA, such that the proportion of specific template was varied between 100% and 5%. a) Reactions contained CYP2D6 primers but lacked NAT2 primers, such that only specific targets were produced. A small variation in crossing-point was observed as the concentration of specific target was reduced. However, amplification and detection efficiencies were comparable between reactions. b) Reactions contained CYP2D6 and NAT2 primers, such that specific and non-specific targets were generated. Significant reductions in amplification and detection efficiencies were observed as the proportion of specific target was reduced. However, results suggest that multiplex reactions containing up to 4 or 5 targets may be possible.

FIG. 13: Multiplex HyBeacon analysis. a) NAT2*4 and CYP2D6 *1 targets were simultaneously amplified and detected in a single microtitre plate well using FAM (BamFL1) and HEX (2D64E) labelled probes respectively. Only reactions containing genomic DNA and sequences fully complementary to HyBeacon probes displayed elevated levels of fluorescence emission throughout amplification. Negative control reactions did not generate increases in fluorescence emission. b) Melt peaks were derived from FAM, HEX and TET labelled probes using the ABI PRISM 7700 instrument and an Excel macro. Melt peaks displayed here were derived from probe hybridisation to complementary oligonucleotides.

Figure 14A:
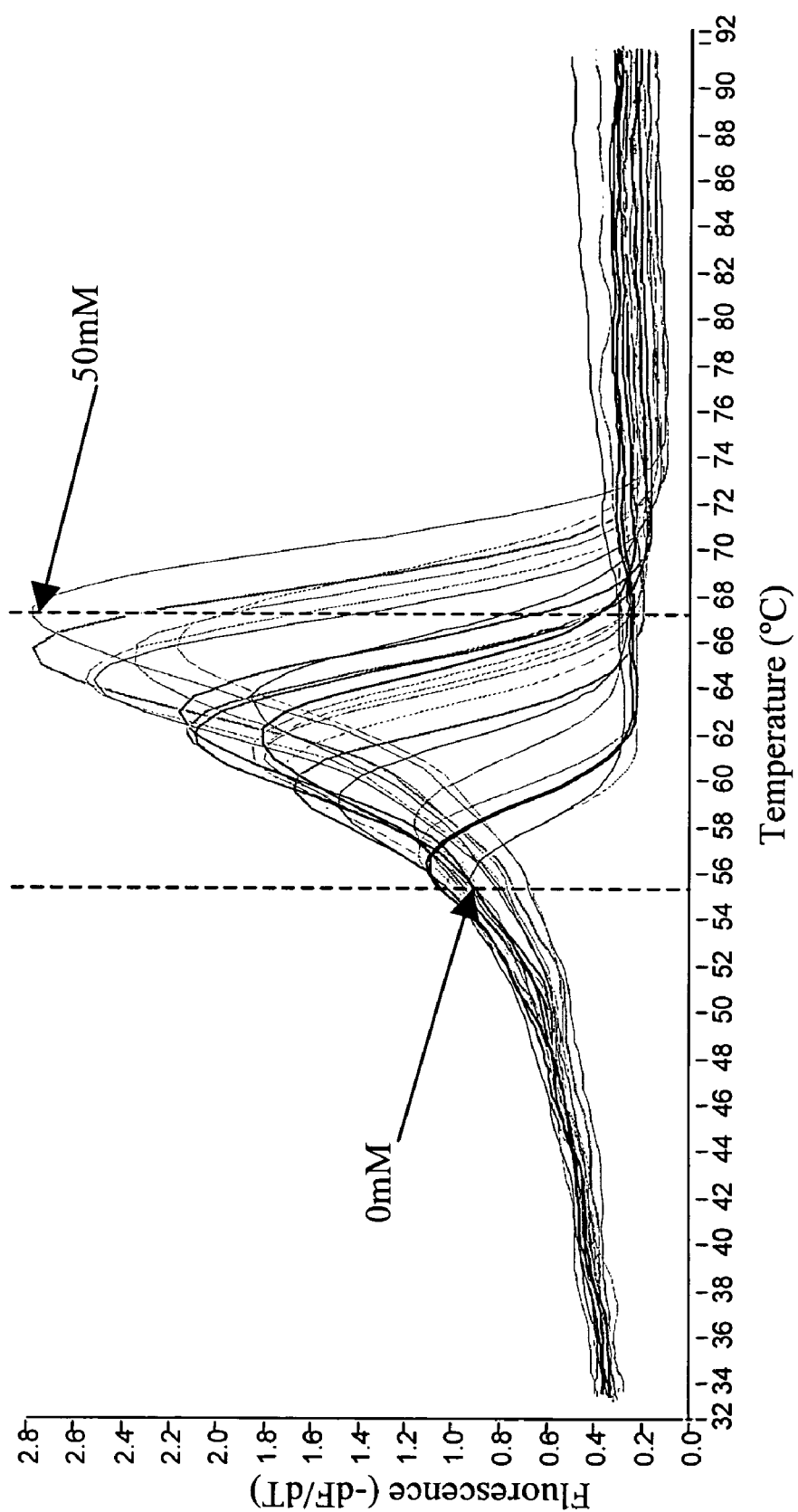
Figure 14B:
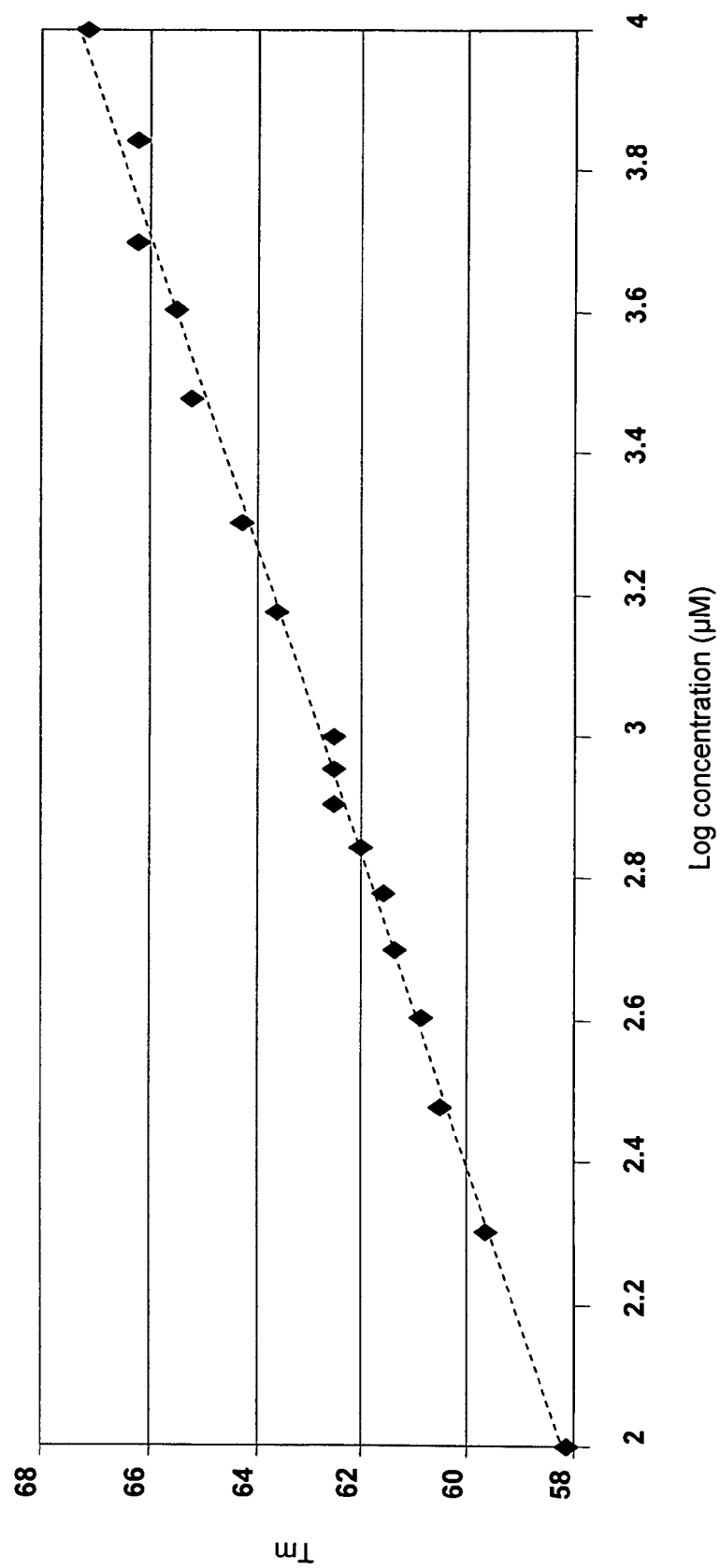
Figure 15A:
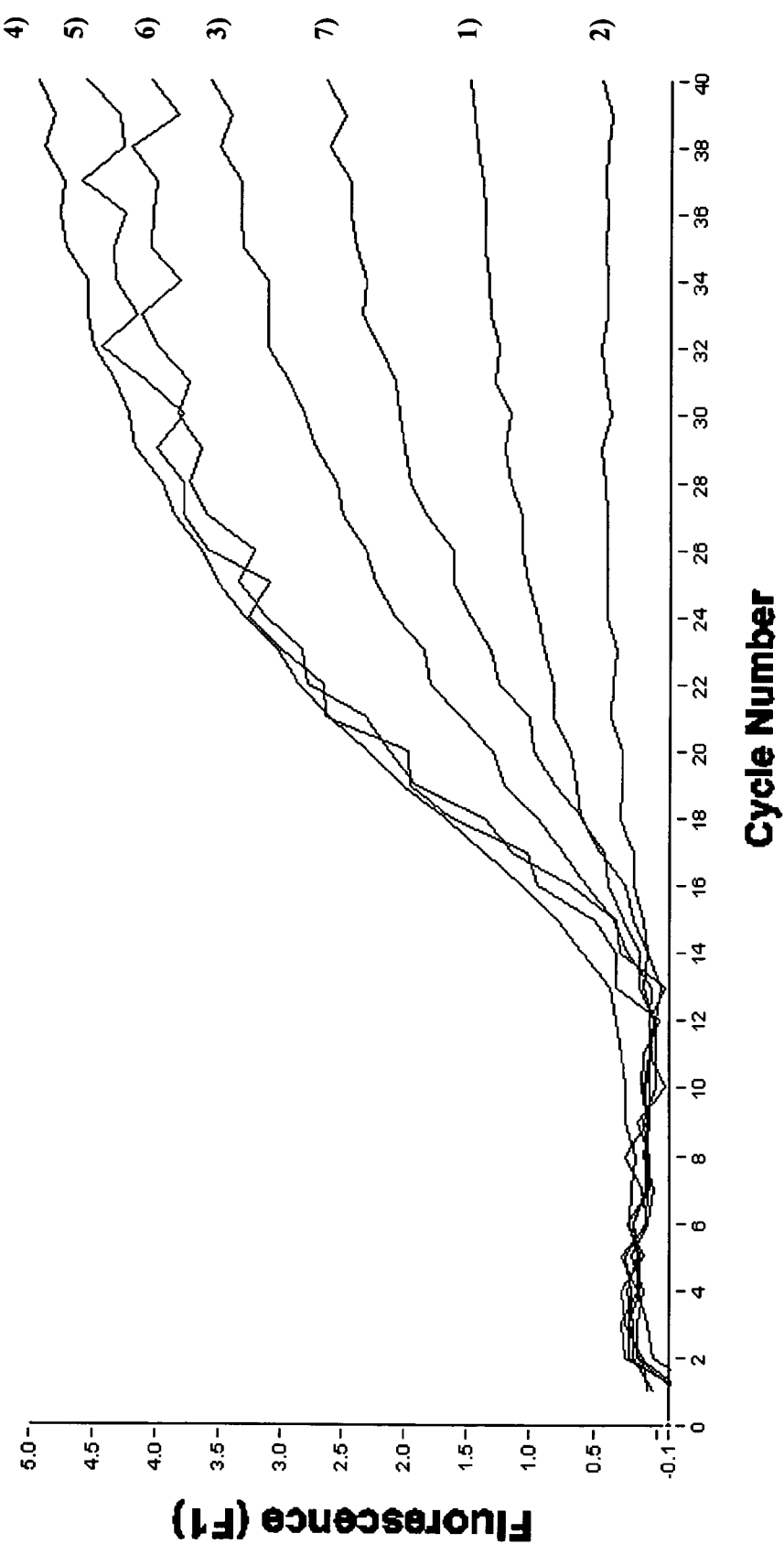
Figure 15B:
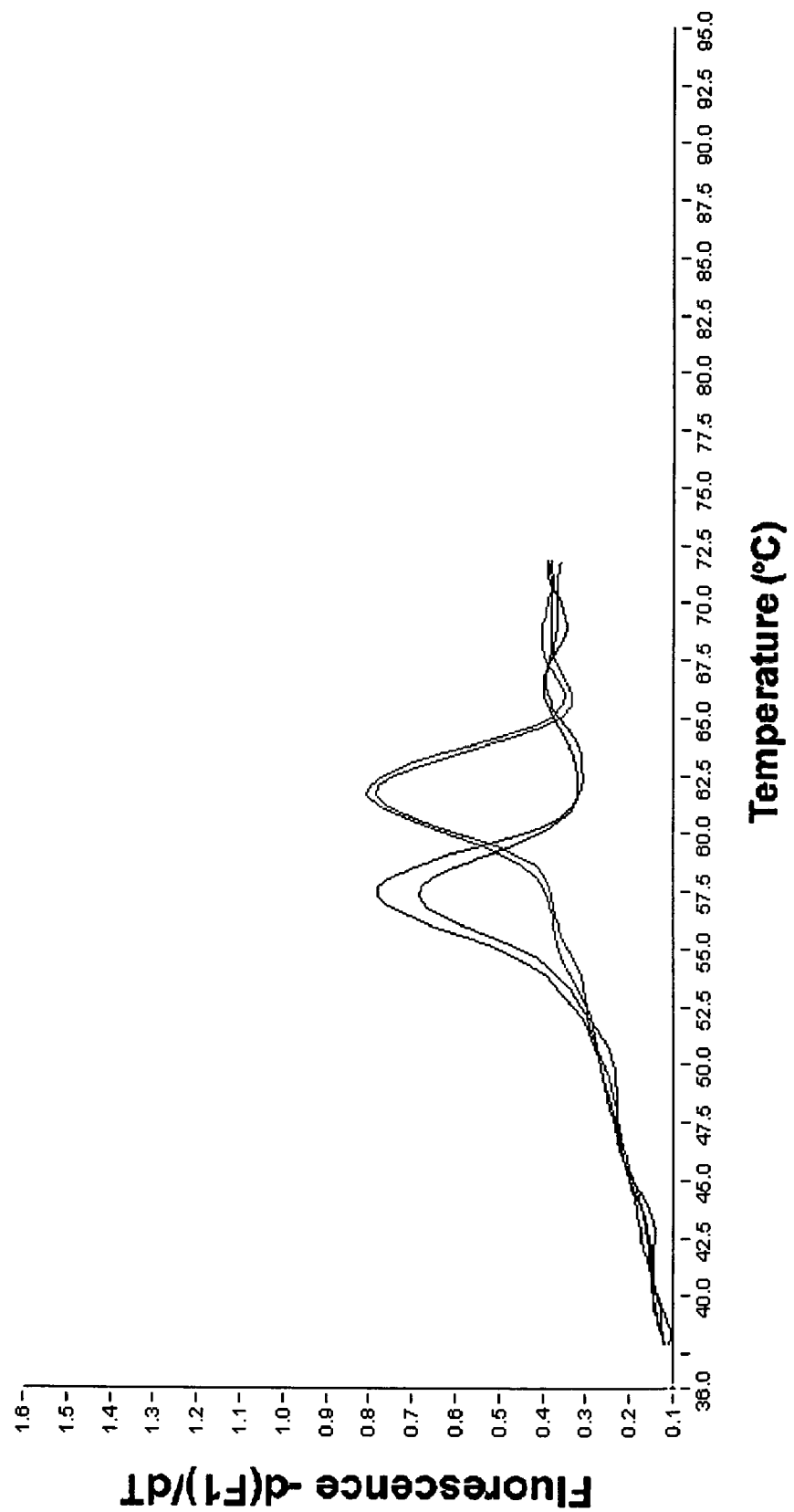
Figure 15C:
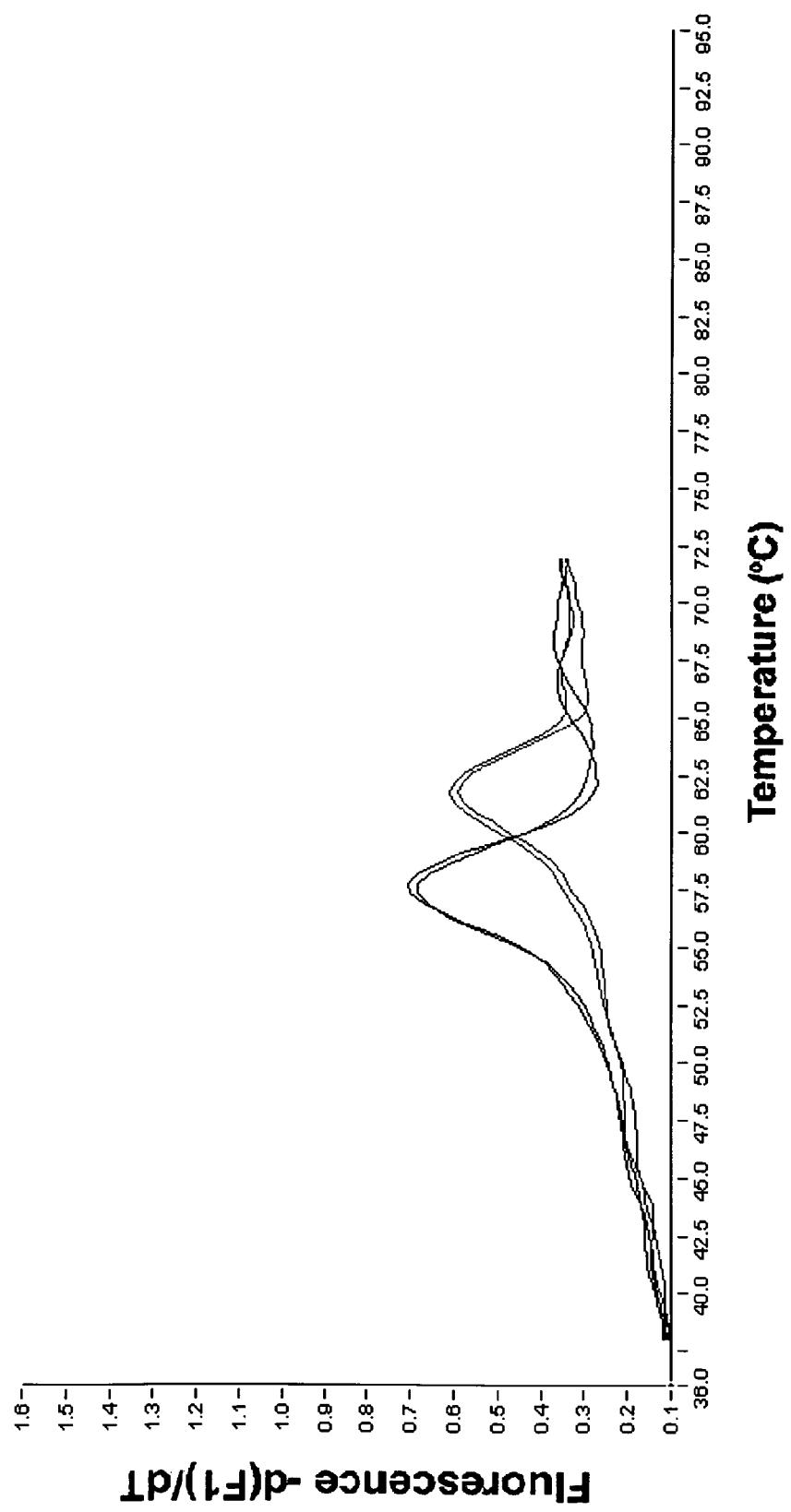
Figure 15D:
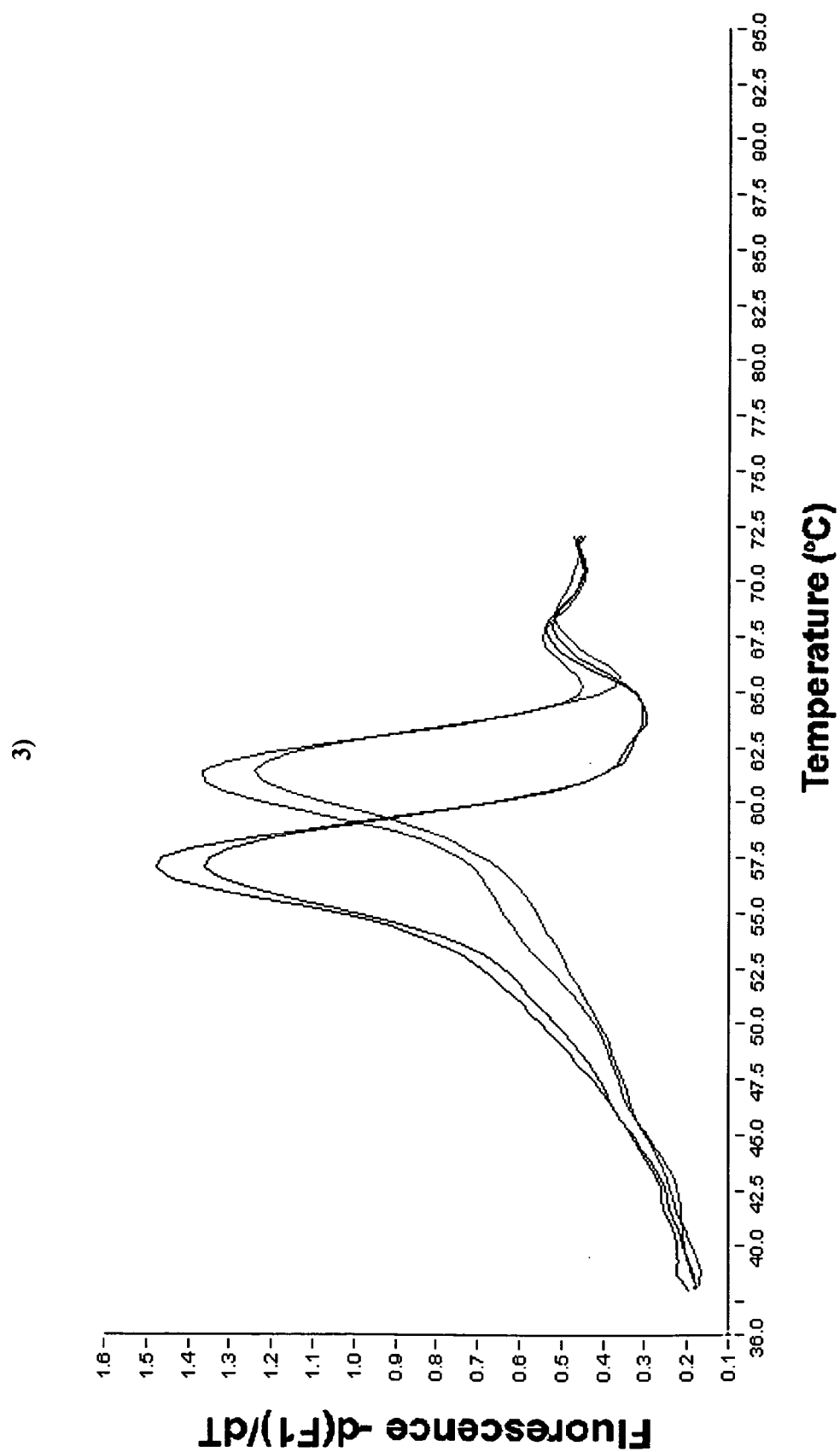
Figure 15E:
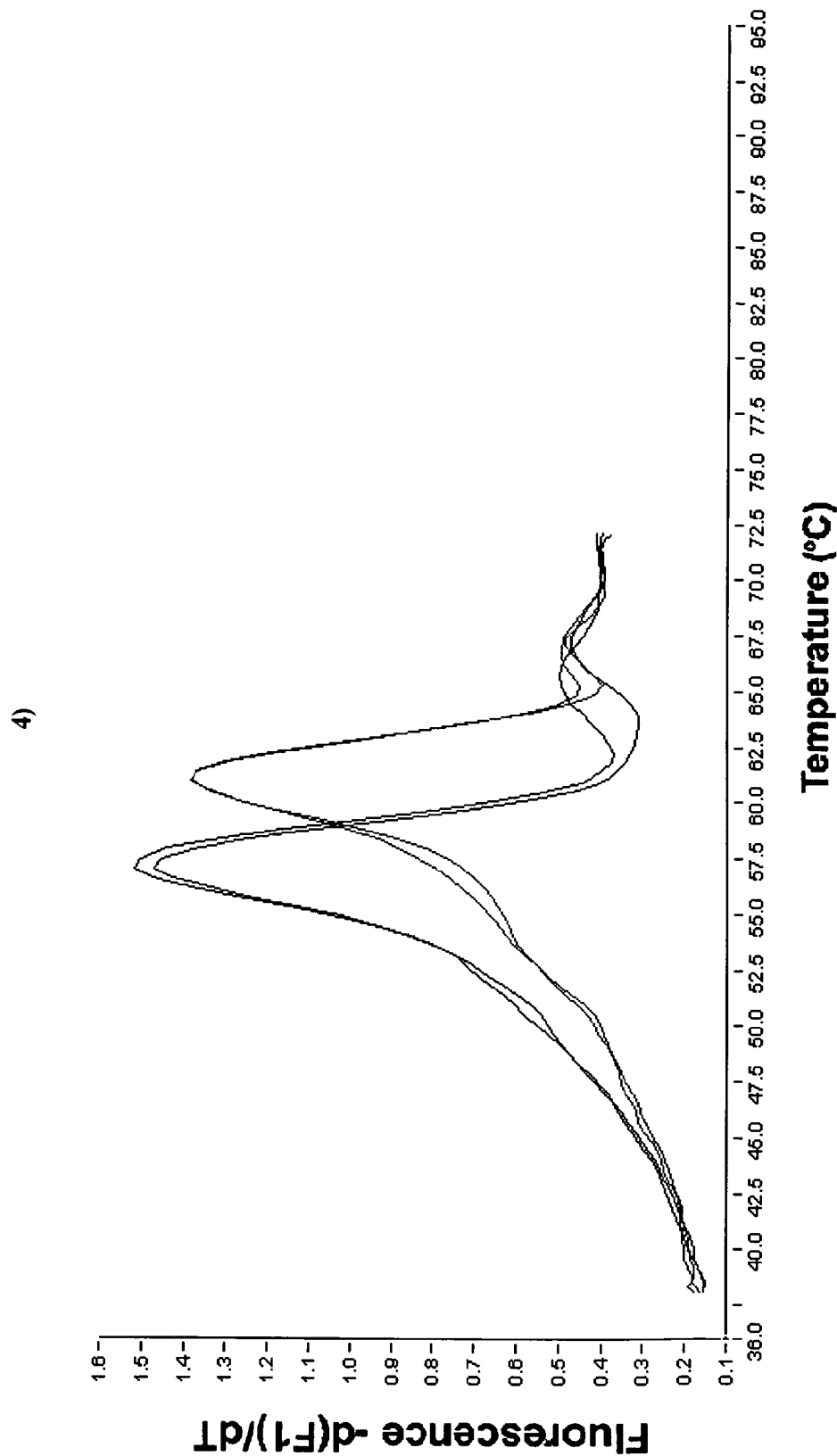
Figure 15F:
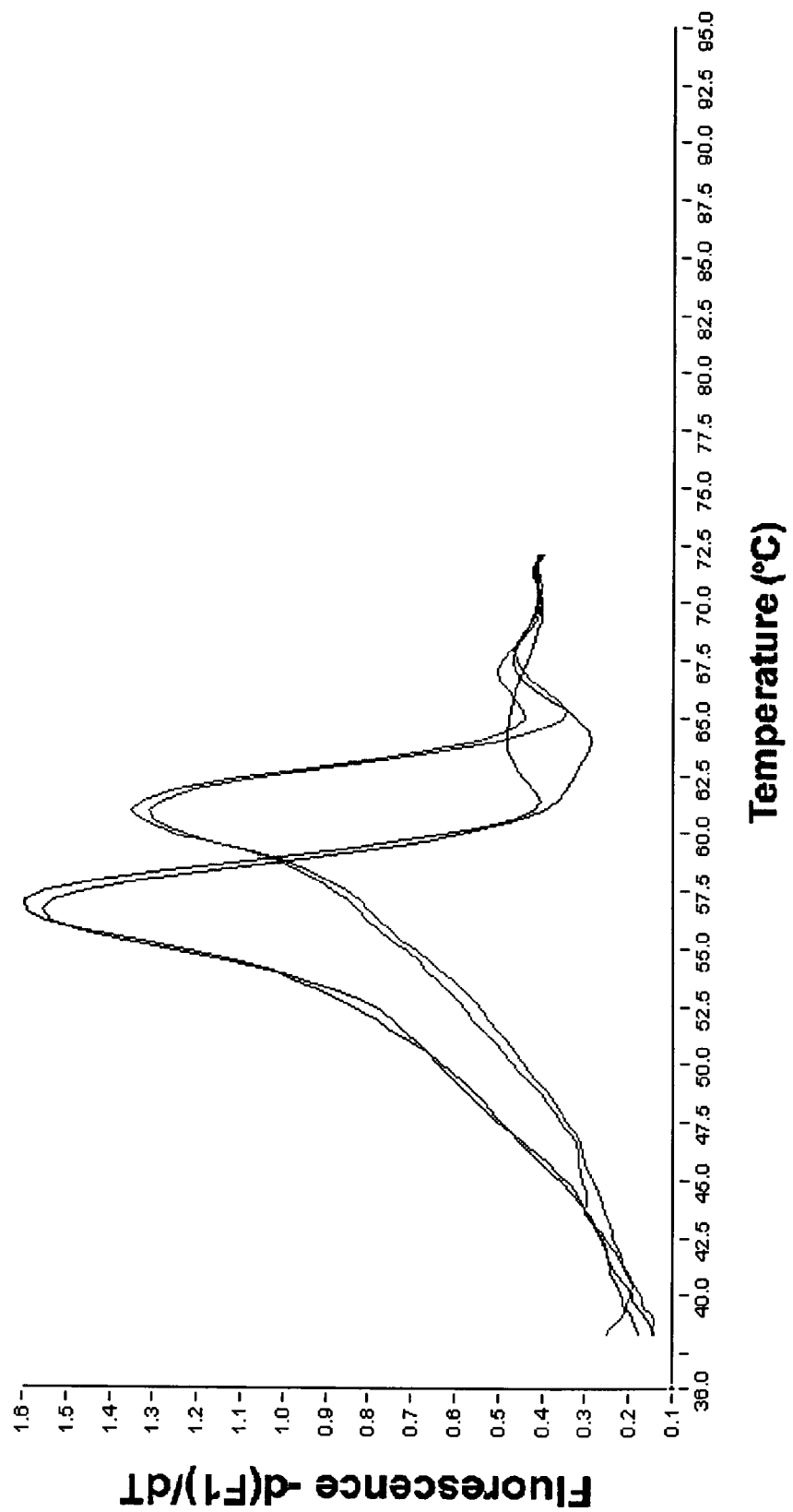
Figure 15G:
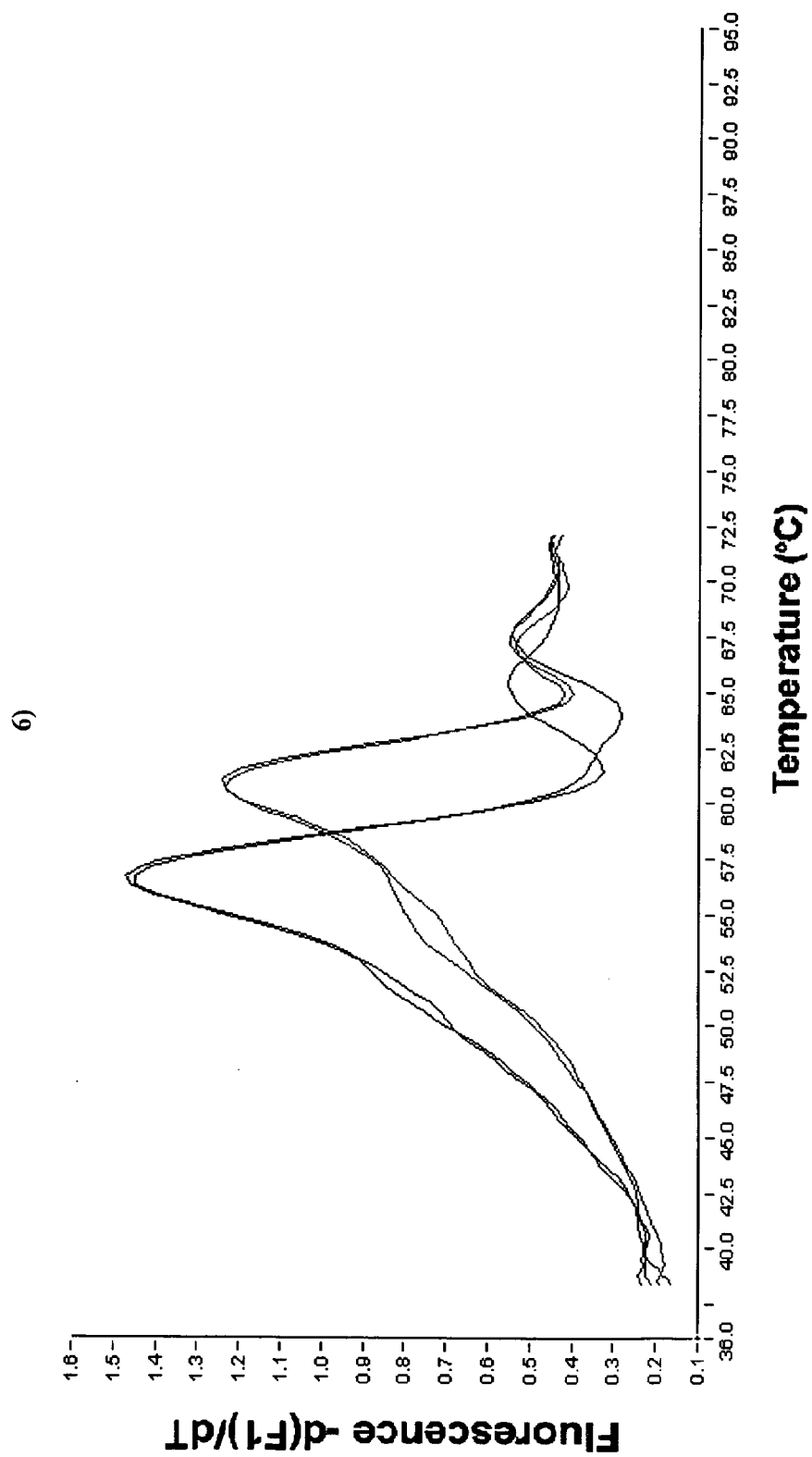
Figure 15H:
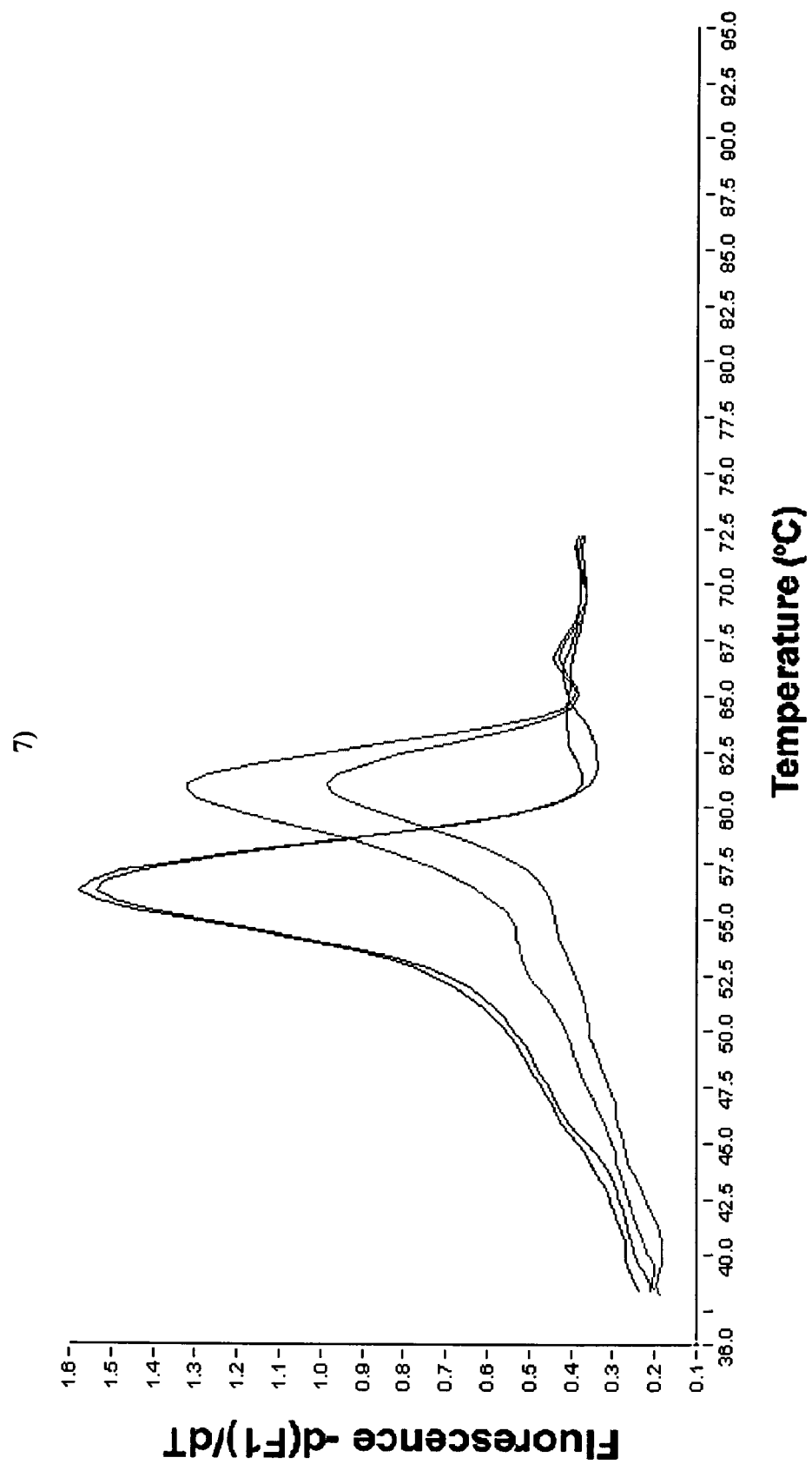

FIG. 14: The effect of $MgCl_2$ concentration on HyBeacon Tm. The hybridisation beacon F17834 was hybridised to a fully complementary oligonucleotide in a series of $MgCl_2$ concentrations, varying from 0mM to 50 mM. The Tm of the hybridisation beacon has been demonstrated to increase as the $MgCl_2$ concentration rises. a) Illustrates the hybridisation beacon melt curves derived from reactions containing: 0 mM, 0.001 mM, 0.005 mM, 0.01 mM, 0.05 mM, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 3 mM, 4 mM, 5 mM, 7 mM, 10 mM and 50 mM $MgCl_2$ (left to right respectively). b) Demonstrates the positive correlation that exists between $MgCl_2$ concentration and HyBeacon Tm. When the Tm of the hybridisation beacon is plotted against the log of $MgCl_2$ concentration, a linear relationship is observed within a defined concentration range (in this case between 0.1 mM and 10 mM). Linear regression analysis performed on this data set generated an $R^2$ value of 99.4%.

FIG. 15: Generation of a HyBeacon PCR buffer—The affect of BSA. Displays the real-time PCR data and post-amplification melt results derived from a series of PCR buffers, using a NAT2*5A HyBeacon (NAT2*5) to monitor target amplification. A range of BSA concentrations were added to a PCR buffer designed for HyBeacon analysis: 1) 0 ng/µl, 2) 1 ng/µl, 3) 2.5 ng/µl, 4) 5 ng/µl, 5) 7.5 ng/µl and 6) 10 ng/µl. TaKaRa Z-Taq PCR buffer (7) was also analysed for comparison. Concentrations of BSA greater than 2.5 ng/µl enhance the efficiency of target amplification and detection in real-time analyses, such that the magnitude of the fluorescence increase is superior to TaKaRa buffer in this instance. The quality of melt peaks derived from HyBeacon analysis is superior in the lower concentrations of BSA. The higher concentrations of BSA decrease melt quality by generating peak 'shoulders' and increasing peak width. The optimal concentration of BSA in real-time and post-amplification analyses appears to be between 2.5 ng/µl and 5 ng/µl.

Figure 16A:
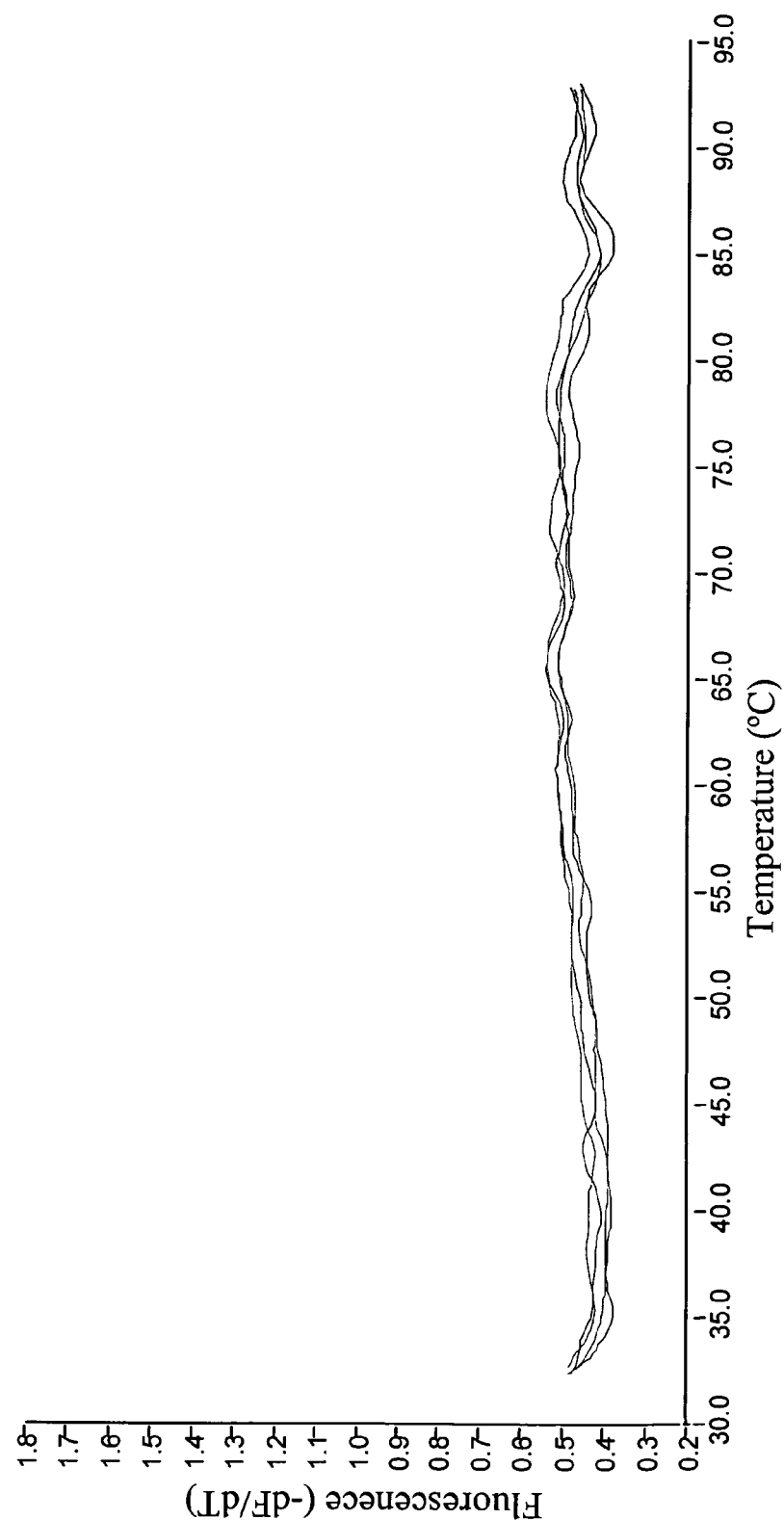
Figure 16B:
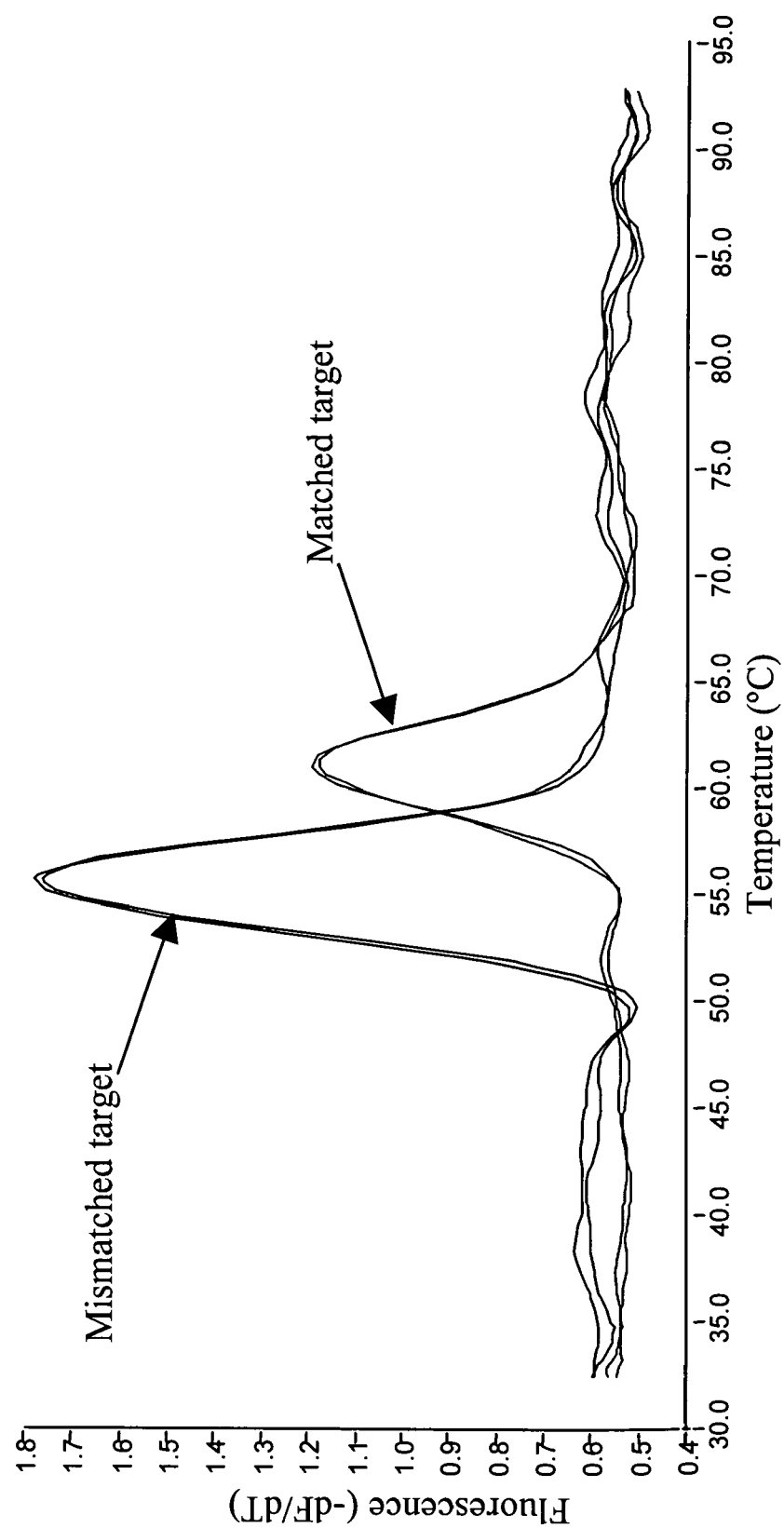

FIG. 16: SNP discrimination efficiency and amplicon size. The size and position of target amplicons has been demonstrated to have significant affects on the efficiency of homogeneous and heterogeneous HyBeacon SNP assays. Two sets of primers, amplifying NAT2*4 products (flanking the *6 SNP) differing in size by 22 bp, were compared in heterogeneous melting curve analysis experiments. a) The 103 bp NAT2 product, amplified from TaqF and TaqR primers, does not generate any melt peaks in heterogeneous assays containing the F17836 HyBeacon. b) However, the 81 bp NAT2*4 product, amplified from TaqF2 and TaqR2 primers, does generate matched and mismatched melting curves with the F17836 probe. 103 bp and 81 bp samples were both detected on agarose gels, confirming that the dissimilarity between amplicons is due to variations in probe hybridisation and not to differences in amplification efficiency.

Figure 17A:
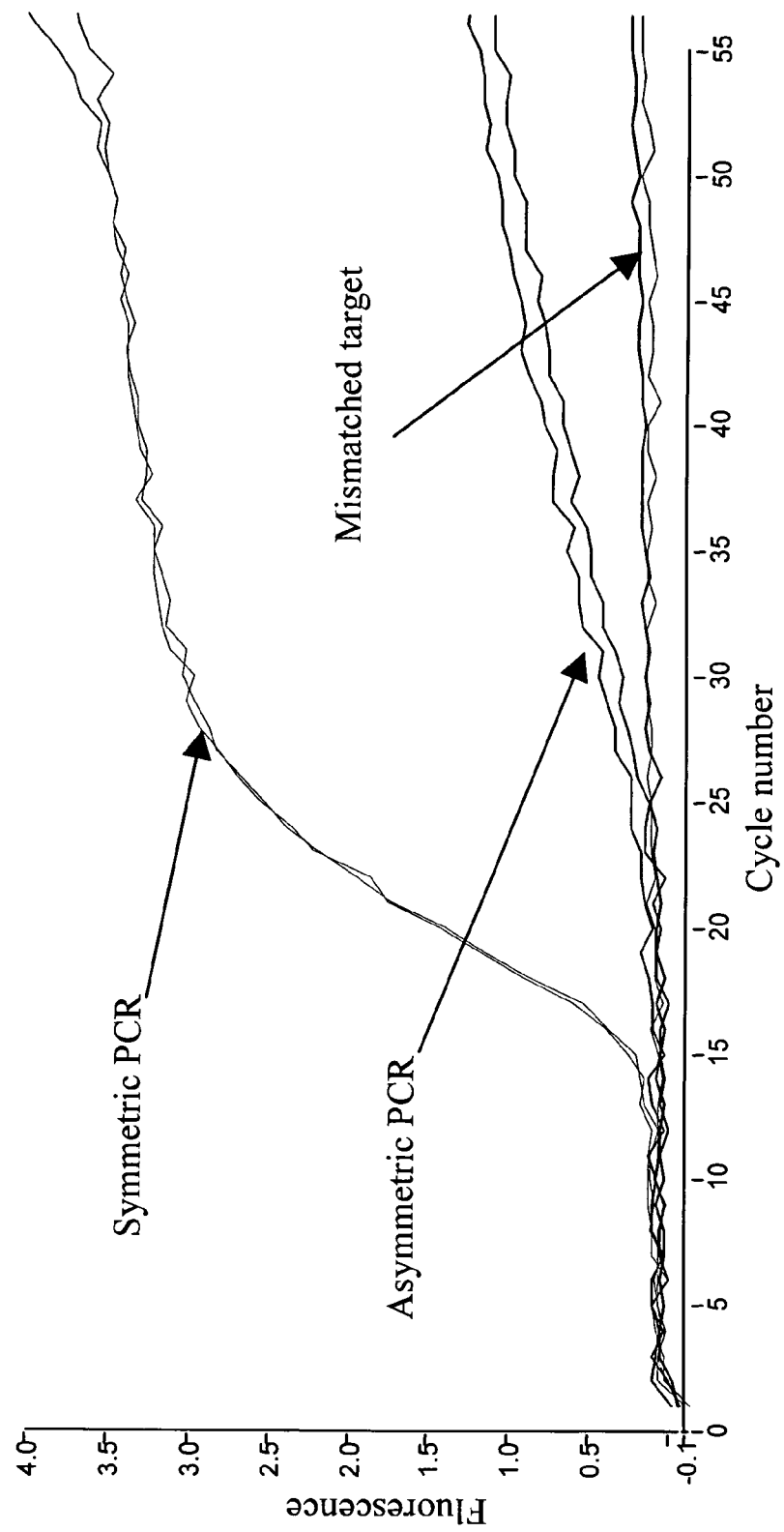

FIG. 17: SNP discrimination using asymmetric target amplification. The efficiencies of HyBeacon mediated target detection and SNP discrimination were compared in symmetric and asymmetric PCR assay formats. Both types of PCR amplification only generate increases in fluorescence signal in the presence of matched target. Eight HyBeacons were compared; four of which displayed equivalent efficiencies between symmetric and asymmetric amplification methods (data not shown). a) The F17836 HyBeacon probe possessed a significantly reduced detection efficiency when employed in asymmetric assays. b) Whilst three other HyBeacons displayed greater amounts of fluorescence increase by asymmetric amplification compared with that generated by symmetric amplification (as demonstrated by the 2D64B probe).

Figure 18:
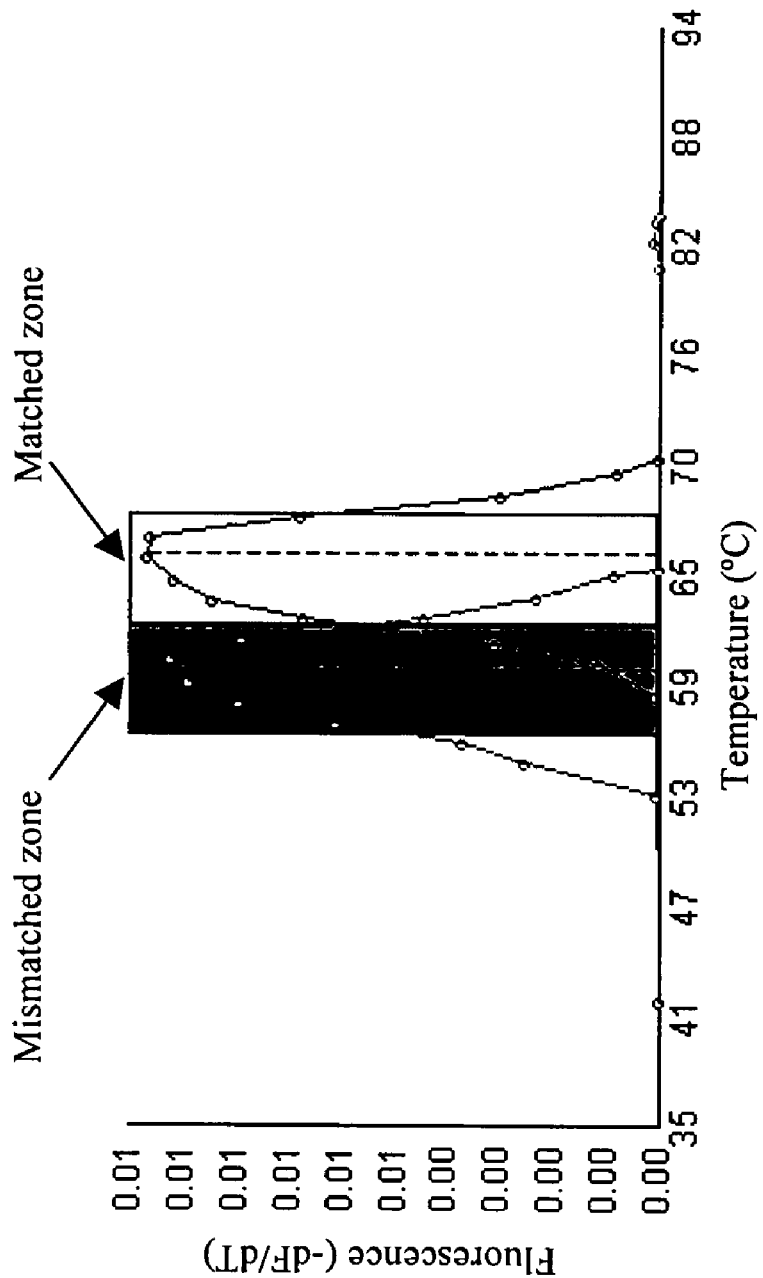

FIG. 18: SNP discrimination using hybridisation beacons and the DASH instrument. The hybridisation beacon F17832, which is fully complementary to the NAT2*4 allele of the *5A polymorphism, was used to discriminate *4 and *5A polymorphic targets immobilised on a solid phase. The hybridisation beacon is fully complementary and mismatched when hybridised to *4 and *5A sequences respectively. Matched and mismatched hybridisation generates melting curves possessing Tms of approximately 66° C. and 60° C. respectively. Establishing matched and mismatched zones for the hybridisation beacon allows automatic classification of samples using the DASH software.

Figure 19A:
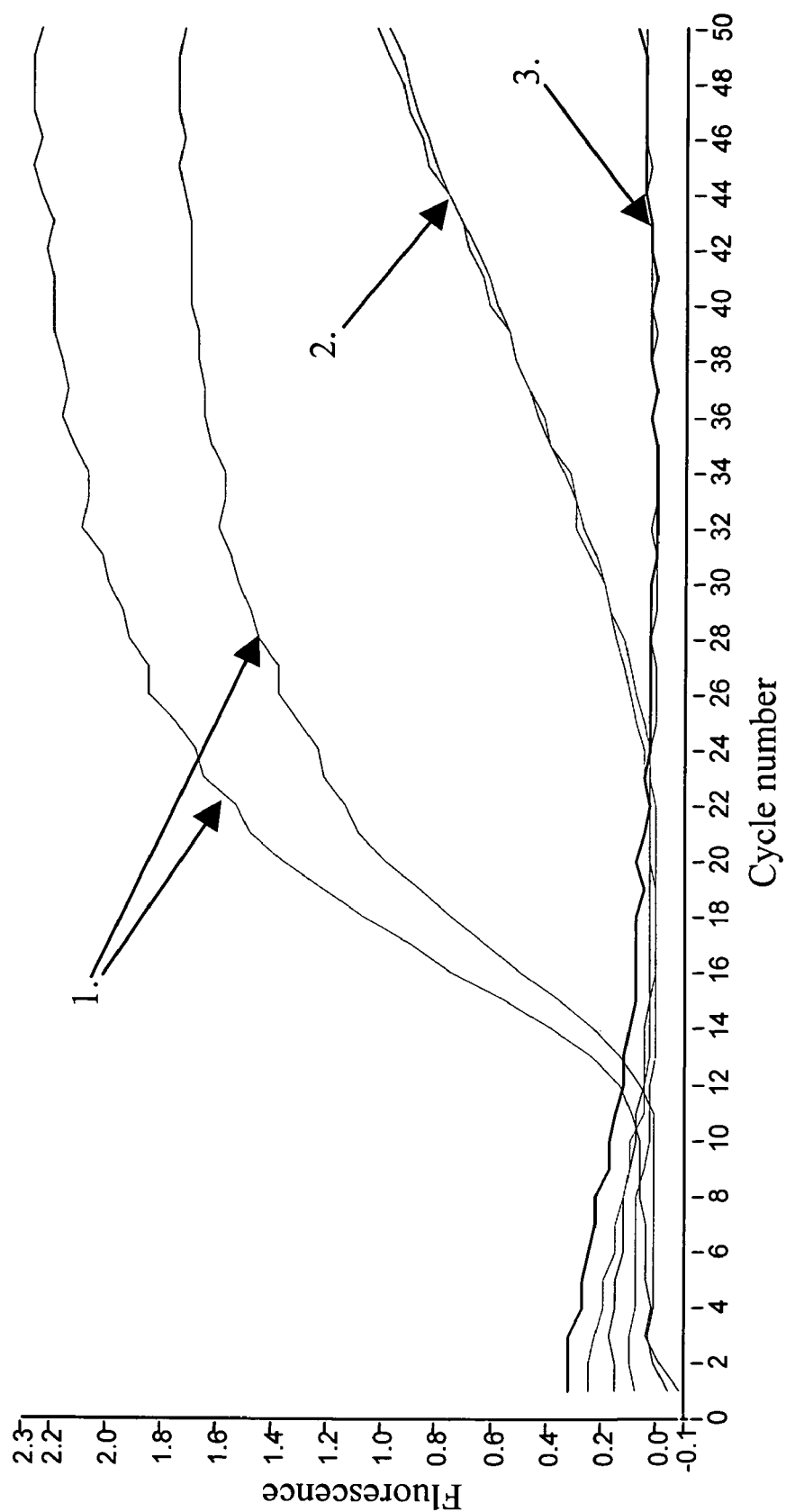
Figure 19B:
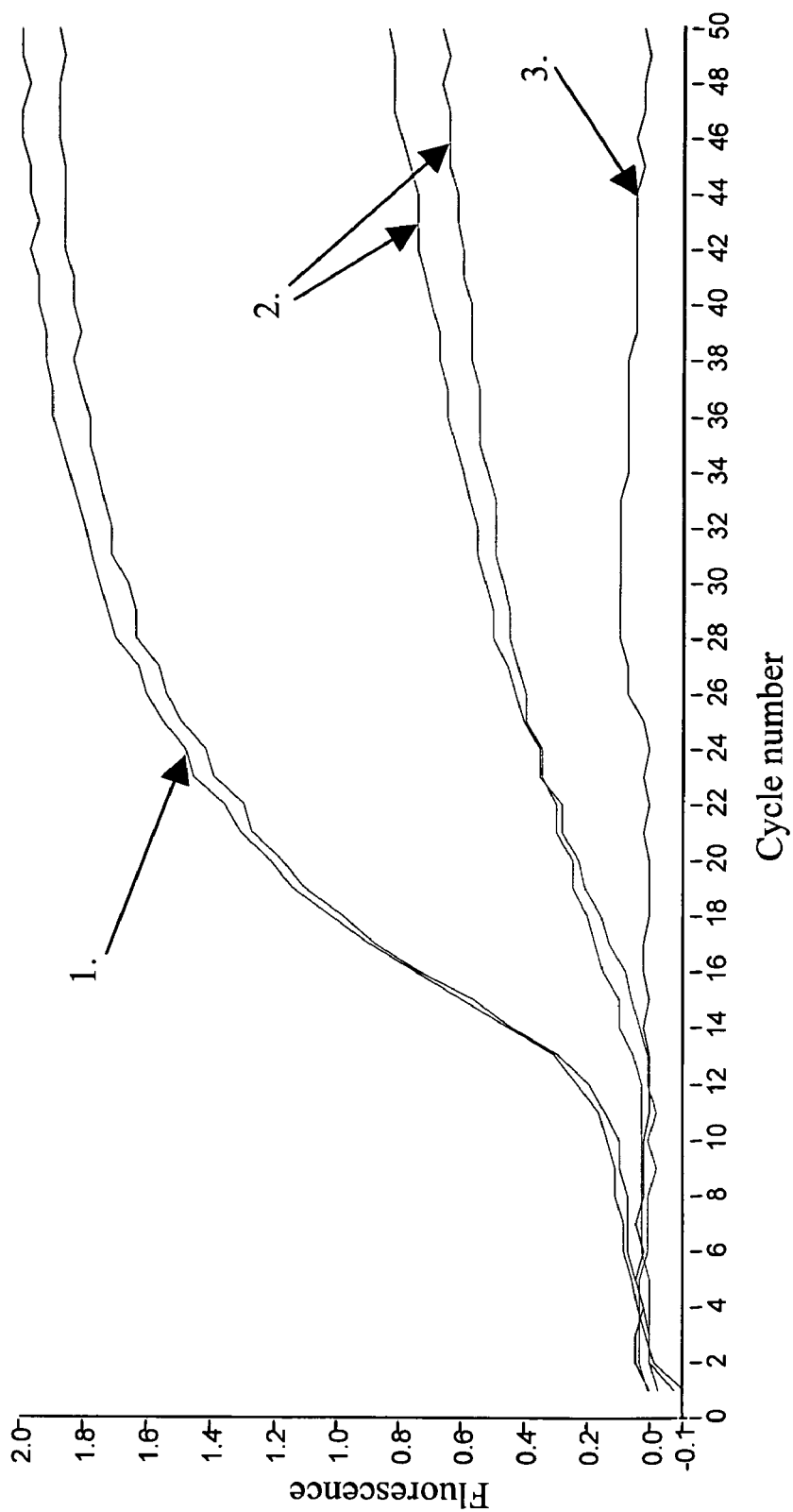

FIG. 19: SNP discrimination using DNA polymerases lacking 5'-3'-exonuclease activity. NAT2*4 and *5A alleles were amplified with DNA polymerases that possess (Taq) and lack (Deep Vent and Stoffel fragment) 5'-3' exonuclease activity, to examine whether F HyBeacon probe digestion is required to generate increases in fluorescence emission. The F HyBeacon 0203002 was used to detect amplification and discriminate SNPs. a) Comparison of Taq (1) and Deep Vent (2) polymerases amplifying the fully complementary *4 sequence. Both polymerases generate 'real-time' increases in fluorescence emission with the matched template whilst reactions containing mismatched *5A template do not produce increases in fluorescence emission (3). b) Comparison of Taq (1) and Stoffel fragment (2) polymerases amplifying the fully complementary *4 allele. Both polymerases generate 'real-time' increases in fluorescence emission in the presence of matched *4 template but reactions containing only the mismatched *5A allele do not produce increases in fluorescence emission (3).

Figure 20A:
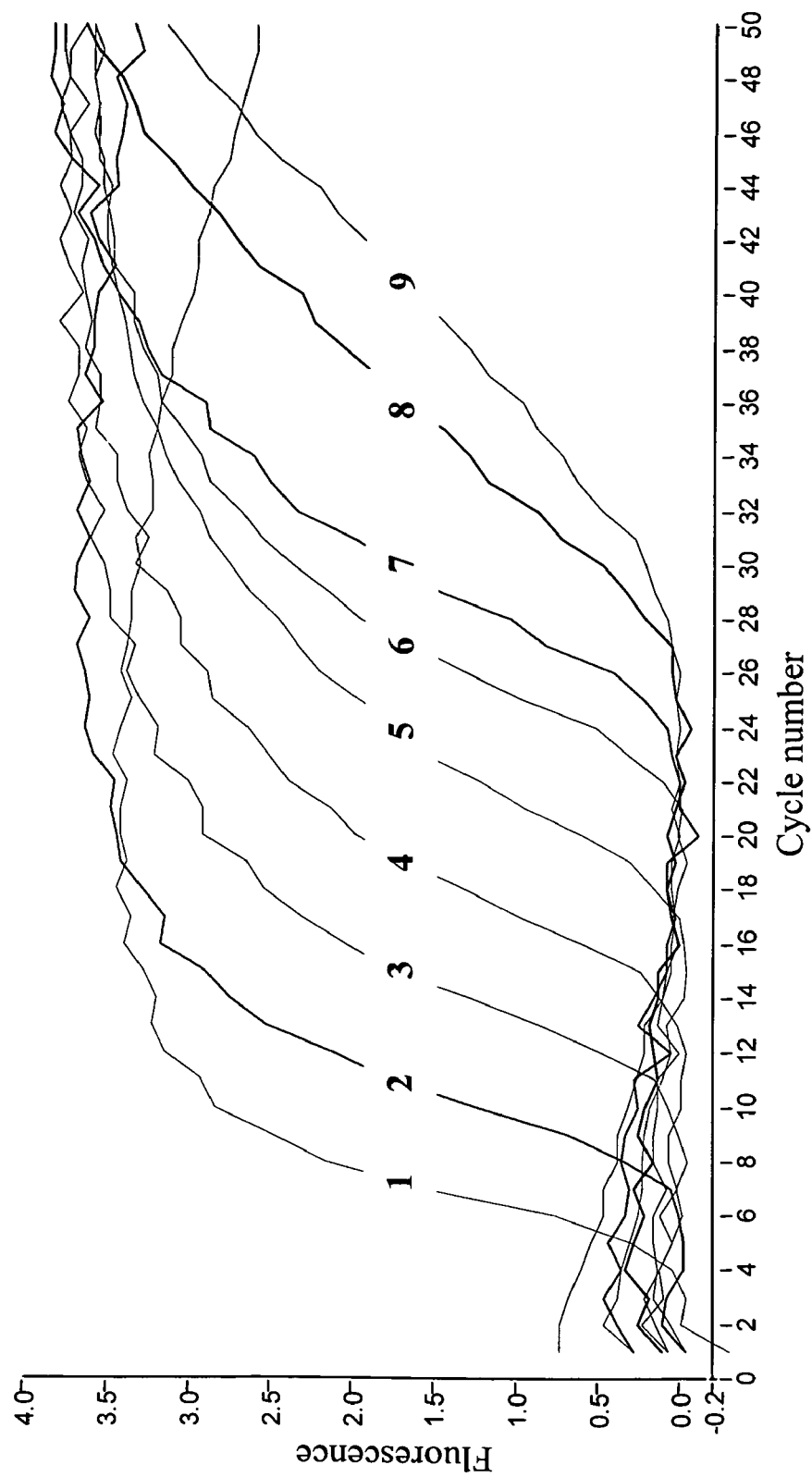
Figure 20B:
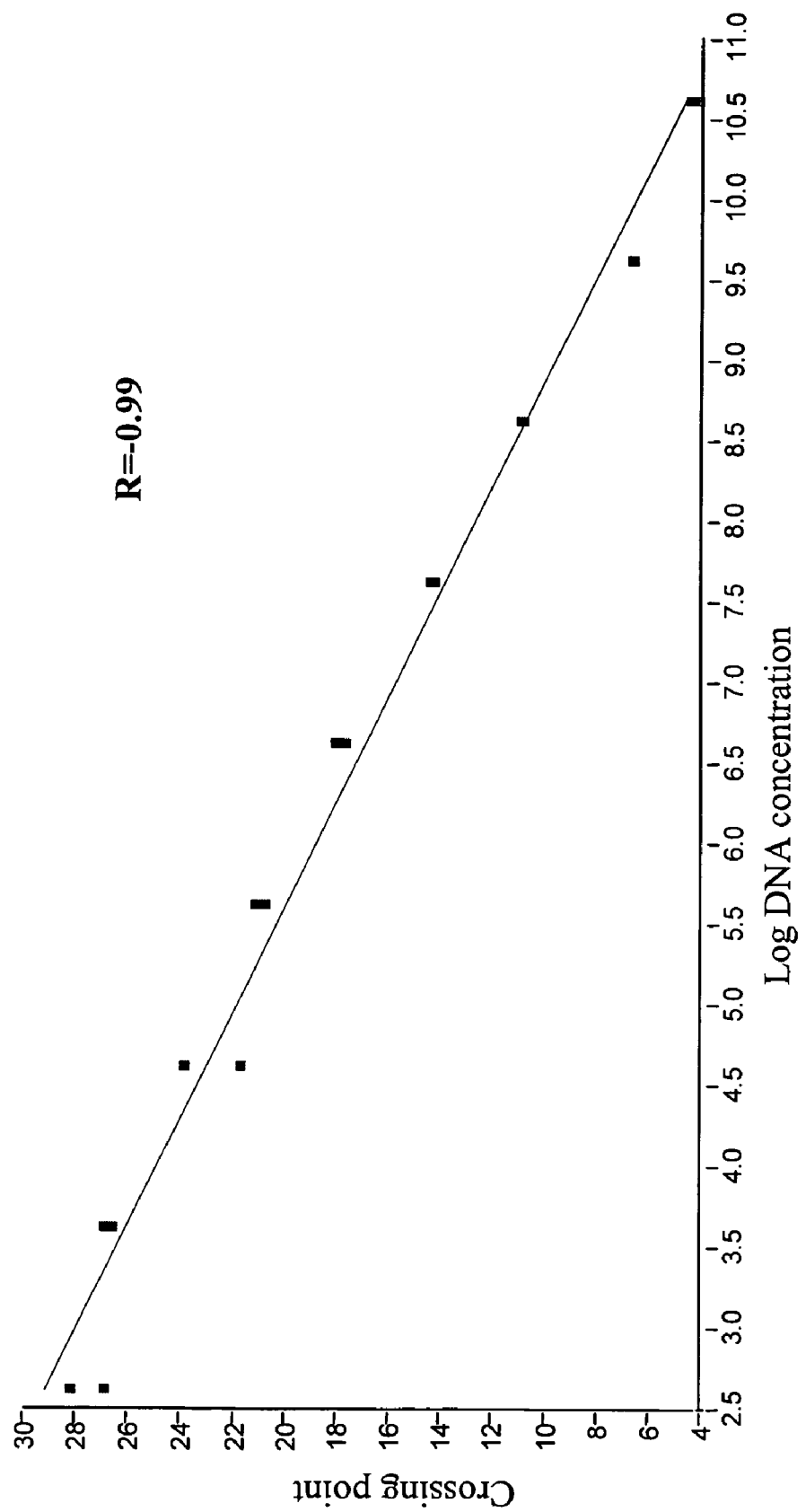

FIG. 20: 'Real-time' quantitative PCR using a HyBeacon probe. a) 'Real-time' homogeneous assays were performed using the 2D64B HyBeacon to monitor amplification of a CYP2D6 sequence. A range of known DNA concentrations were analysed: 1) $41.5 \times 10^9$ attograms per microlitre (ag/µl), 2) $41.5 \times 10^8$ ag/µl, 3) $41.5 \times 10^7$ ag/µl, 4) $41.5 \times 10^6$ ag/µl, 5) $41.5 \times 10^5$ ag/µl, 6) $41.5 \times 10^4$ ag/µl, 7) $41.5 \times 10^3$ ag/µl, 8) $41.5 \times 10^2$ ag/µl and 9) 415 ag/µl. Crossing points were measured for each DNA concentration. b) Standard curves were constructed by plotting Log DNA concentration against crossing-point. Standard curves were used to quantify DNA concentrations present in 'unknown' reaction samples.

Figure 21A:
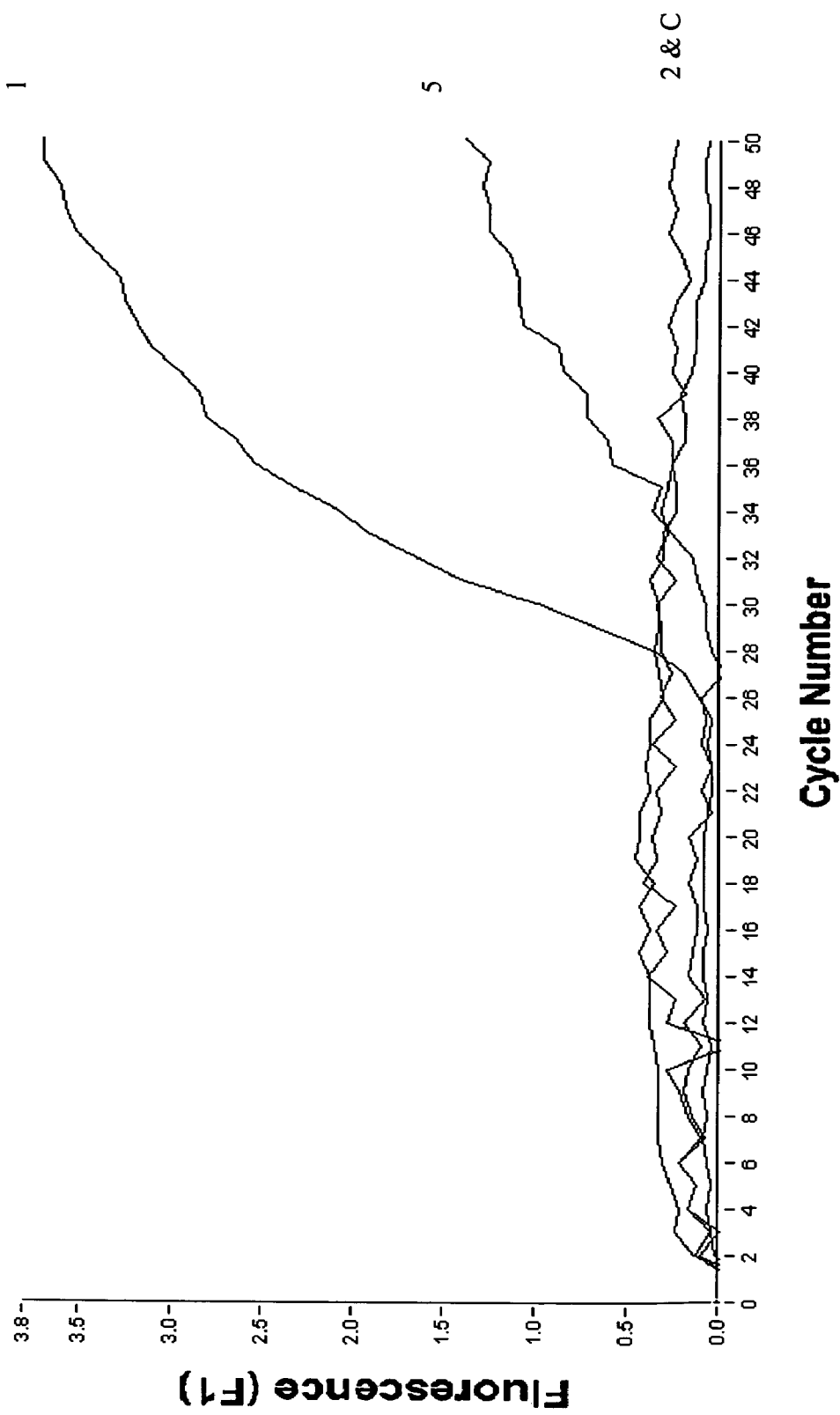
Figure 21B:
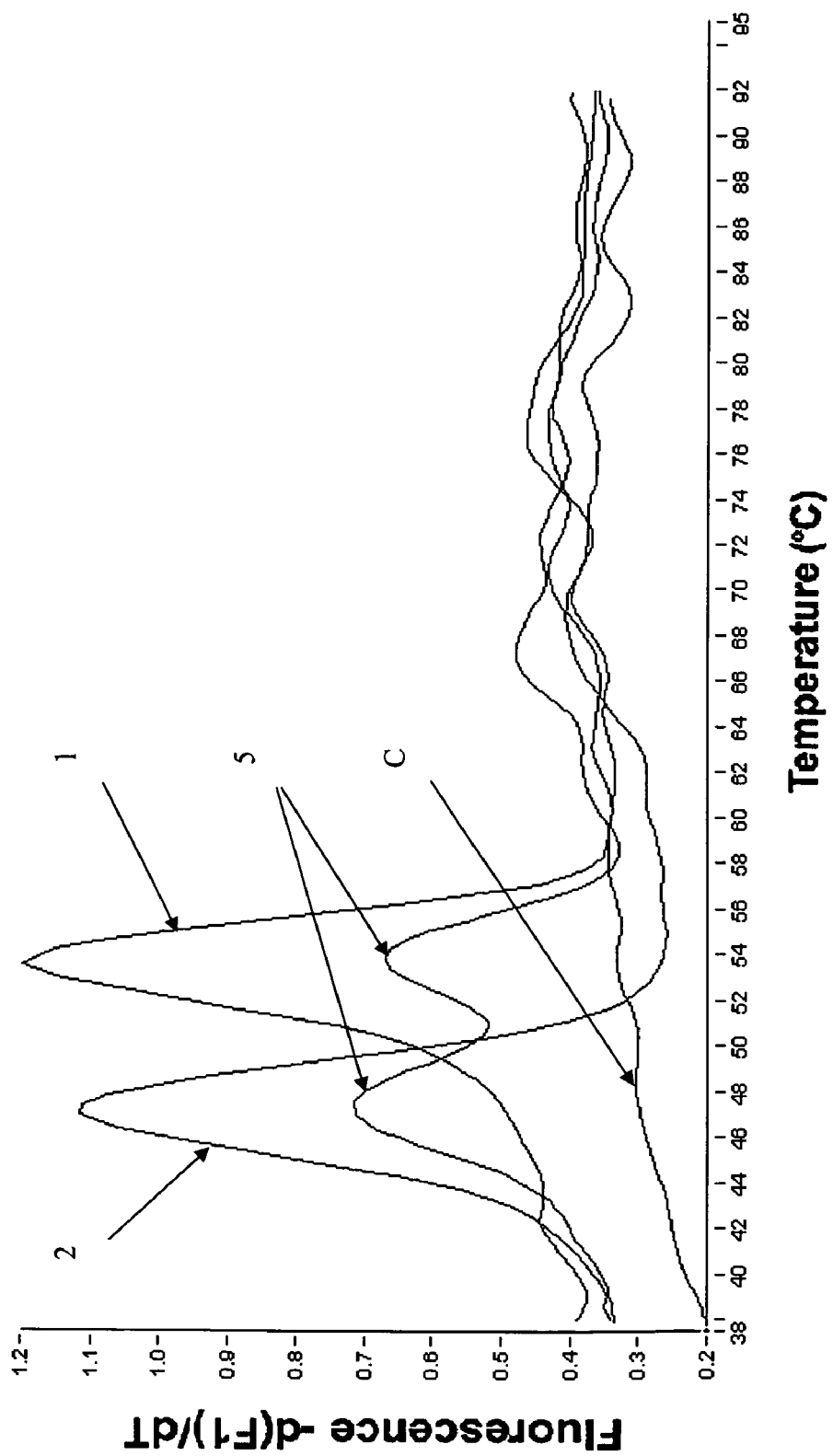

FIG. 21: Homogenous real-time saliva analysis. Detection and discrimination of NAT2*4 and *5C polymorphic targets were performed by real-time PCR and melting analysis methodologies. The DdeFL1 HyBeacon, which is fully complementary to the *5C allele of the NAT2 gene, was used to genotype three saliva samples (1, 2 & 5). A no template control reaction (C) was also included in the analysis. a) Increases in fluorescent signal are only generated in homogeneous PCR reactions in the presence of the *5C allele. Therefore, reactions that are homozygous and heterozygous for the *5C allele (i.e. samples 1 & 5 respectively) generate significant increases in fluorescent signal, whilst reactions homozygous for the *4 allele (sample 2) do not produce increases in fluorescent signal. Heterozygous samples, possessing both *5C and *4 alleles, cause intermediate quantities of fluorescence to be generated during amplification. b) The DdeFL1 probe generates single melt peaks, possessing Tms of 47.6° C. and 54.1° C., when hybridised to homozygous *4 and *5C DNA respectively. Heterozygous samples generate traces possessing both 47.6° C. and 54.1° C. melt peaks, whilst reactions that lack target DNA do not generate either peak.

Figure 22:
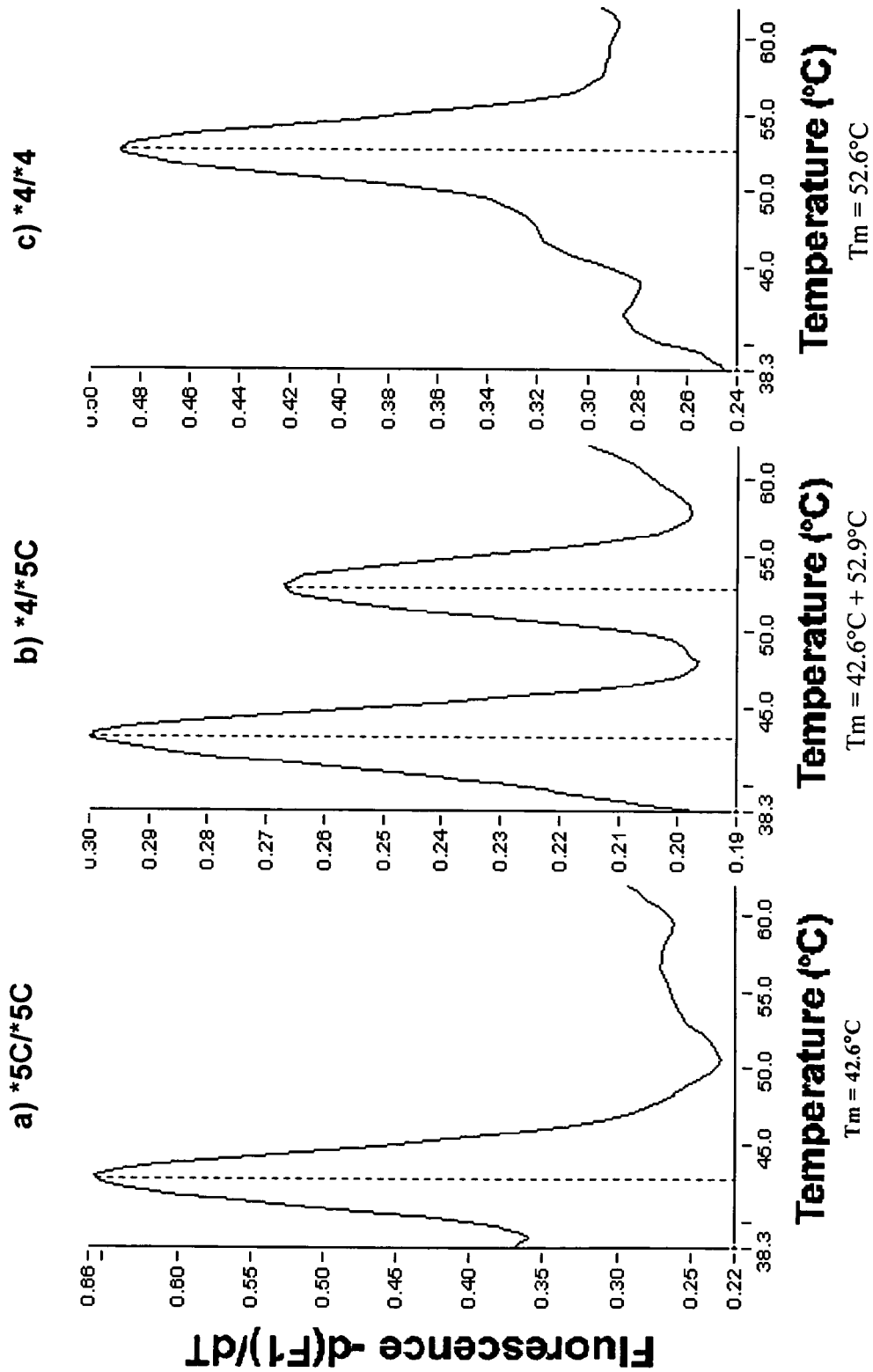

FIG. 22: HyBeacon melting peak analysis of saliva amplified DNA. The DdeFL1*4 HyBeacon, which is fully complementary to the *4 allele of the NAT2 gene, was employed to genotype saliva samples with respect to the *5C polymorphism. a) Saliva sample 1 is homozygous for the *5C allele since HyBeacon hybridisation results in a single mismatched melt peak possessing a Tm of 42.6° C. b) Saliva sample 3 is heterozygous for *5C and *4 alleles since two peaks are generated during melting analysis. c) Saliva sample 2 is homozygous for the *4 allele since probe hybridisation produces a single matched melt peak possessing a Tm of 52.6° C.

FIG. 23: RFLP saliva analysis. Restriction Fragment Length Polymorphism analysis was performed for NAT2*4 and *5C PCR products amplified from saliva samples. Lane M is a 10 bp ladder (GIBCO BRL). Restriction enzyme digestion permits samples 1-3 to be typed as *5C/*5C, *4/*4 and *4/*5C respectively.

Figure 24B:
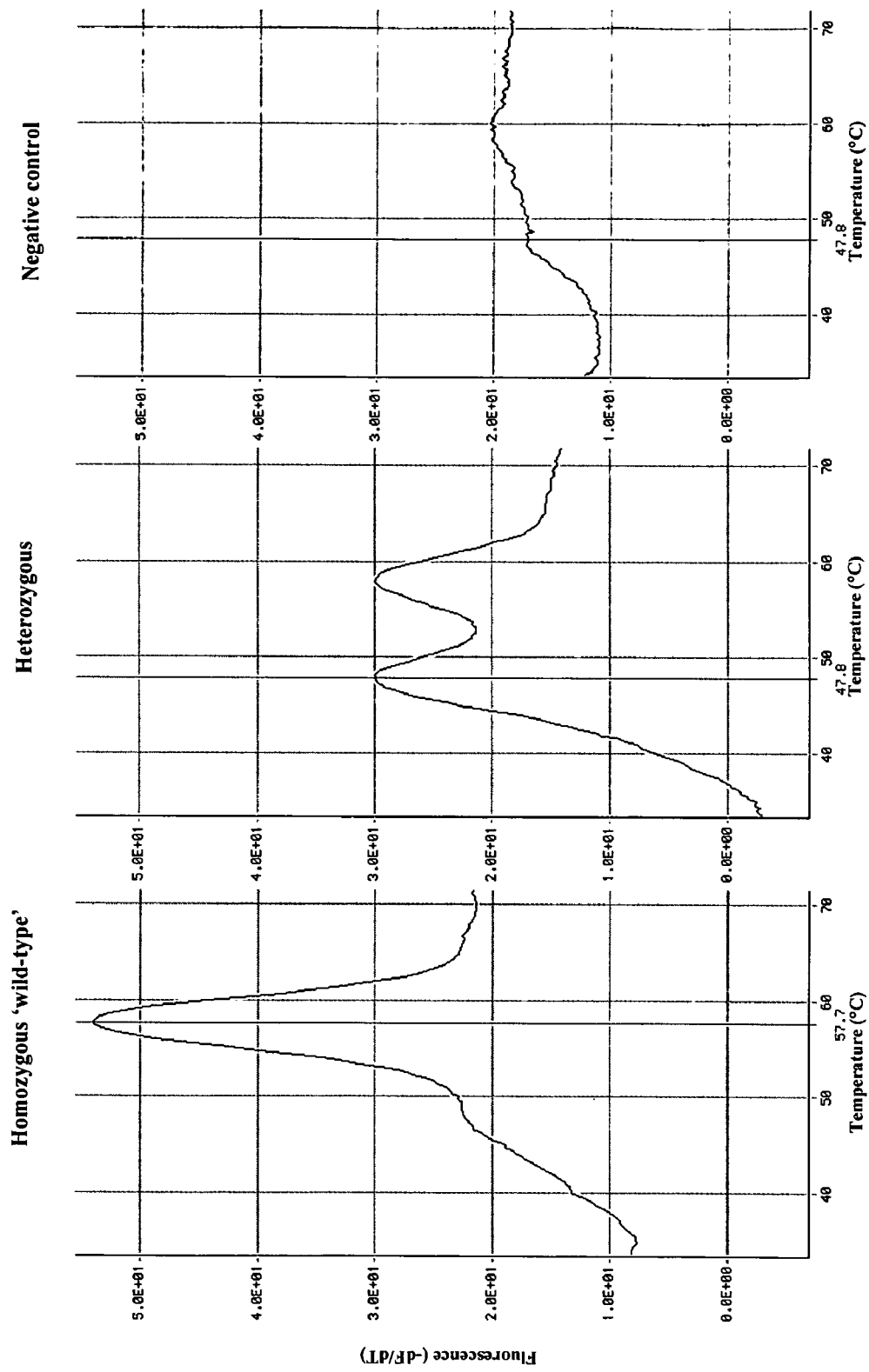

FIG. 24: Analysis of factor V Leiden sequences. Melt peaks were derived, following amplification of polymorphic target sequences, using a) LightCycler and b) ABI 7700 instruments. The HyBeacon probe FVG1 generates a single melt peak possessing a Tm of approximately 58° C. when hybridised to the fully complementary 'wild-type' allele of the factor V gene. Hybridisation to the mismatched 'mutant' allele of the R506Q polymorphism results in peaks possessing Tms of 48° C. Heterozygous samples generate melting traces possessing both the 48° C. and 58° C. peaks. In the absence of target DNA, no melt peaks are observed.

Figure 25:
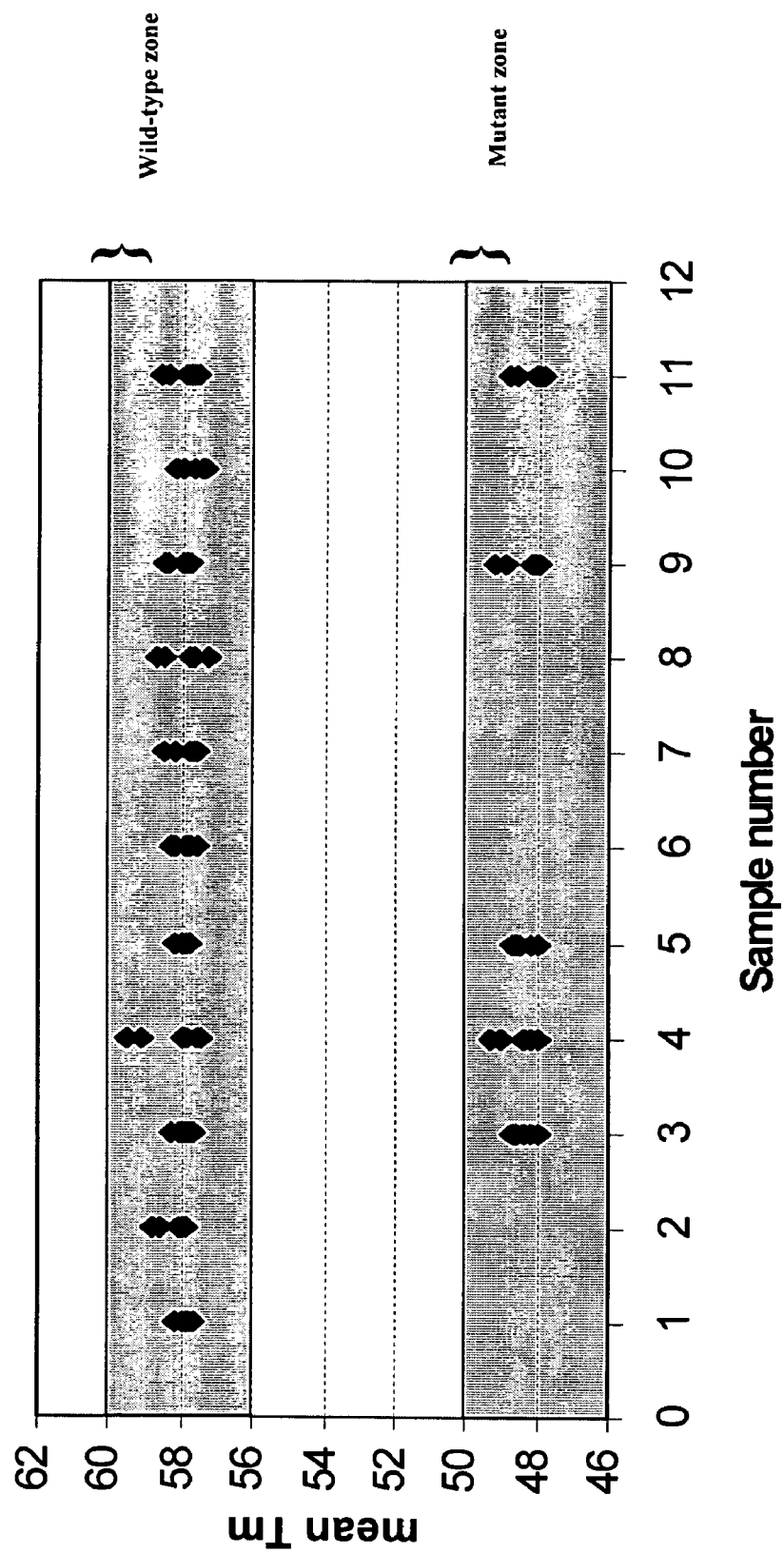

FIG. 25: Assay variation and confidence of analysis. Nine clinical samples (1-9) and two control templates (10-11) were typed with respect to the factor V Leiden polymorphism using the FVG1 probe. Despite small variations of melting temperature between reactions, all Tm values were located within two discrete zones established for wild-type and mutant alleles. Wild-type and mutant Tm zones were established using the 99.9% confidence intervals calculated for samples 1-11, using at least 6 replicates of each. Samples may be genotyped with at least 99.9% confidence, since Tm values are not observed between the two Tm zones.

Figure 26A:
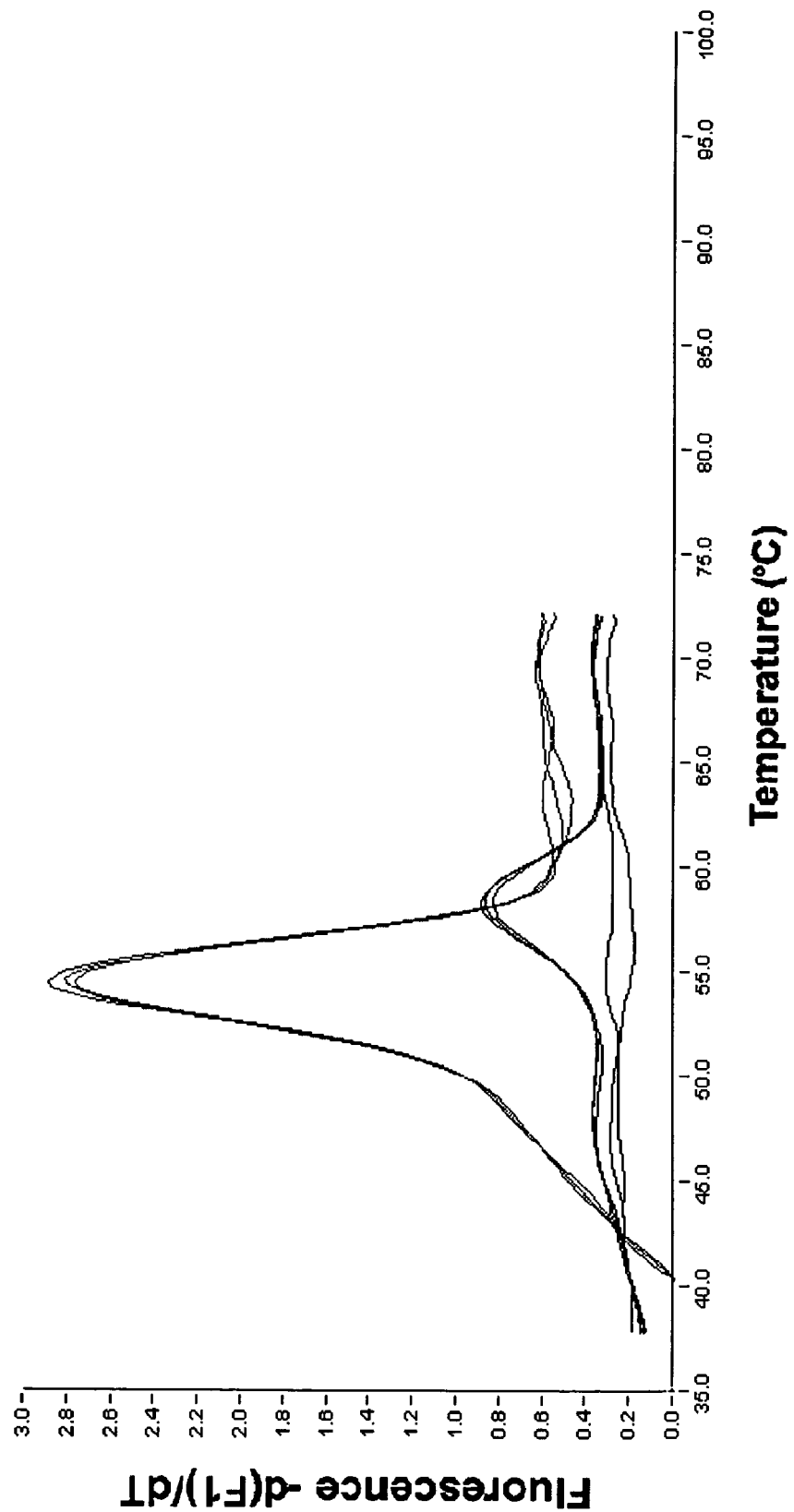
Figure 26B:
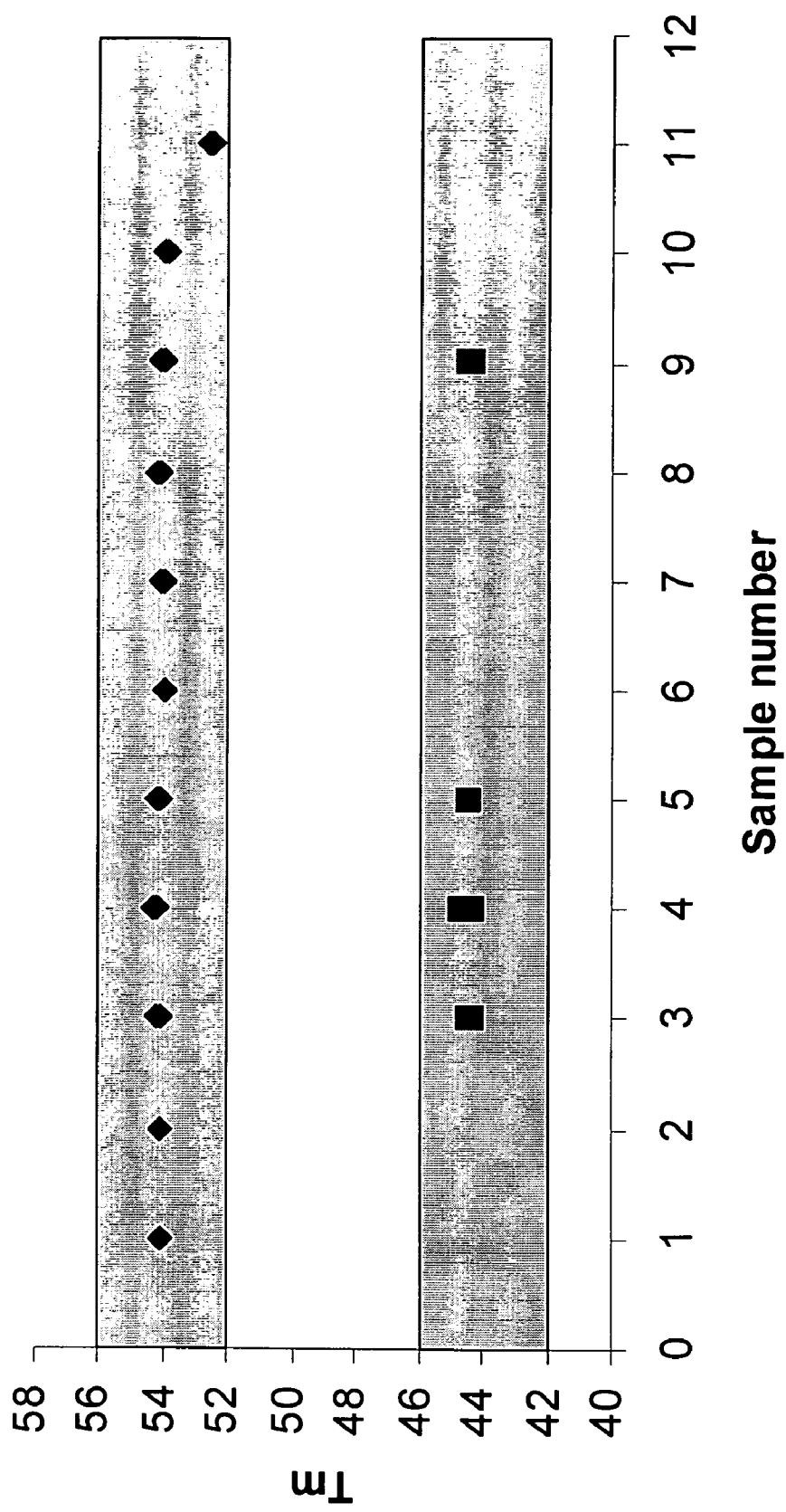

FIG. 26: Dual-labelled F hybridisation beacons. Hybridisation beacons containing either one or two dU C6 FAM monomers were employed to genotype samples with respect to the factor V Leiden polymorphism. a) The single and dual-labelled probes are both fully complementary to the wild-type allele of the R506Q polymorphism, generating melt peaks of 58° C. and 54° C. when hybridised respectively. The additional fluorophore of the dual-labelled probe destabilises hybridisation and reduces Tm by approximately 4° C. However, the relative heights of melt peaks derived from the dual-labelled probe are approximately 4 times greater than those derived from the equivalent single-labelled probe. b) Clinical samples and control DNAs were typed for the factor V Leiden polymorphism using the dual-labelled probe. Homozygous wild-type samples generate single melt peaks possessing Tms of approximately 54° C. Whereas, samples that are heterozygous for wild-type and mutant alleles generate two peaks that possess Tms of approximately 54° C. and 44.5° C. respectively.

MATERIALS AND METHODS

(i) Hybridisation Beacon Design.

HyBeacon probes were designed to hybridise to ten SNPs located in the human N-acetyltransferase 2 (NAT2) gene (see table 1) and the cytochrome P450 encoding (CYP) genes (see tables 2 and 3). Probes were designed such that polymorphic nucleotides are positioned towards the centre of HyBeacon sequences. All HyBeacon probes are approximately 20 nucleotides in length and possess fluorophore moieties linked to internal uracil residues (replacing thymine in DNA sequences). The fluorescent dyes 6-carboxyfluorescein (FAM), tetrachlorofluorescein (TET) and hexachlorofluorescein were attached to U residues by novel chemistries (available from Oswel DNA services, Southampton, UK) and six fluorophore linkage chemistries (FAM propo dU, FAM propargyl dU, dU C6 FAM, dU FAM, FAM cap prop dU and FMOC dU) were evaluated. The dU C6 FAM and FMOC dU fluorophores were found to generate slightly superior data and were used preferentially. In F-Q HyBeacons, quencher moieties (Methyl Red) were also positioned on internal U residues, where HyBeacons with 1, 3, 5, 6, 7, 8 and 9 nucleotide residues separating fluorophore and quencher molecules have been tested. F-Q HyBeacons possessing fluorophore and quencher molecules flanking and non-flanking the polymorphic nucleotide were investigated. The majority of HyBeacons synthesised possess a 3' phosphate or octanediol component to prevent Taq mediated extension from HyBeacons when the probes are incorporated into real-time PCR assays. F and F-Q HyBeacons were designed to be perfectly matched to one allele of NAT2 and CYP polymorphic sequences, such that the other variant of an SNP created a position of mismatch upon probe hybridisation. HyBeacon probes, fully complementary to both alleles, were synthesised for each biallelic SNP.

The NAT2 polymorphic sequence (Sequence ID No. 60). Sequence of the human gene for arylamine N-acetyltraferase 2 (NAT2). Positions containing single nucleotide polymorphisms (SNPs) are shown in bold type. Restriction fragment length polymorphisms exist of positions 481 (*5A), 590 (*6), 803 (*5C) and 857 (*7A).

(ii) Amplification of NA T2 and CYP2D6 Polymorphic PCR Products.

Polymorphic targets were amplified from either saliva (diluted to 50% with water), genomic DNA isolated from reference blood samples (University of Dundee), human placental genomic DNA (Sigma-Aldrich) or pGEM-T plasmids (Promega) containing amplified NAT2 and CYP products. Various primer pairs, generating NAT2 and CYP amplicons differing in size and position relative to the polymorphic sites, were evaluated. For example, the optimal primer pairs used to amplify the NAT2*5A, NAT2*5C, NAT2*6, NAT2*7A, CYP2D6*3 and CYP2D6*4 polymorphic sequences were 195991/195993, DdeF2/DdeR, TaqF2/TaqR2, BamF2/BamR, 2D63F/2D63R and 2D64F2/2D64R2 respectively (table 4). Standard polymerase chain reaction (PCR) was performed to amplify DNA fragments of approximately 80-150 bp that contained the polymorphic nucleotides. Target detection and SNP discrimination assays were performed in heterogeneous and homogeneous formats.

TABLE 2

The nucleotide sequences of F-Q HyBeacon probes designed for NAT2 (*5A, *5C, *6 and *7A) and CYP2D6 (*3 and *4) polymorphisms. FAM fluorophore (5) and quencher (6) moieties were linked to internal uracil residues by novel chemistries. The majority of oligonucleotide probes were end-blocked using a 3'-phosphate (3P).

| HyBeacon | Description | Sequence (5' → 3') |
|---|---|---|
| B9412 | FAM propo dU, NAT2 *5A | GAATCTGGTA5C6GGACCAA Sequence ID No. 1 |

TABLE 1

```
  1 ATGGACATTG AAGCATATTT TGAAAGAATT GGCTATAAGA ACTCTAGGAA CAAATTGGAC

61 TTGGAAACAT TAACTGACAT TCTTGAGCAC CAGATCCGGG CTGTTCCCTT TGAGAACCTT

121 AACATGCATT GTGGGCAAGC CATGGAGTTG GGCTTAGAGG CTATTTTTGA TCACATTGTA

181 AGAAGAAACC GGGGTGGGTG GTGTCTCCAG GTCAATCAAC TTCTGTACTG GGCTCTGACC

241 ACAATCGGTT TTCAGACCAC AATGTTAGGA GGGTATTTTT ACATCCCTCC AGTTAACAAA

301 TACAGCACTG GCATGGTTCA CCTTCTCCTG CAGGTGACCA TTGACGGCAG GAATTACATT

361 GTCGATGCTG GGTCTGGAAG CTCCTCCCAG ATGTGGCAGC CTCTAGAATT AATTTCTGGG

421 AAGGATCAGC CTCAGGTGCC TTGCATTTTC TGCTTGACAG AAGAGAGAGG AATCTGGTAC

481 CTGGACCAAA TCAGGAGAGA GCAGTATATT ACAAACAAAG AATTTCTTAA TTCTCATCTC

541 CTGCCAAAGA AGAAACACCA AAAAATATAC TTATTTACGC TTGAACCTCG AACAATTGAA

601 GATTTTGAGT CTATGAATAC ATACCTGCAG ACGTCTCCAA CATCTTCATT TATAACCACA

661 TCATTTTGTT CCTTGCAGAC CCCAGAAGGG GTTTACTGTT TGGTGGGCTT CATCCTCACC

721 TATAGAAAAT TCAATTATAA AGACAATACA GATCTGGTCG AGTTTAAAAC TCTCACTGAG

781 GAAGAGGTTG AAGAAGTGCT GAAAAATATA TTTAAGATTT CCTTGGGGAG AAATCTCGTG

841 CCCAAACCTG GTGATGGATC CTTACTATT TAGAATAAGG AACAAAATAA ACCCTTGTGT

901 ATGTATCACC CAACTCACTA ATTATCAACT
```

TABLE 2-continued

The nucleotide sequences of F-Q HyBeacon probes designed for NAT2 (*5A, *5C, *6 and *7A) and CYP2D6 (*3 and *4) polymorphisms. FAM fluorophore (5) and quencher (6) moieties were linked to internal uracil residues by novel chemistries. The majority of oligonucleotide probes were end-blocked using a 3'-phosphate (3P).

| HyBeacon | Description | Sequence (5' → 3') |
|---|---|---|
| B9413 | FAM propo dU, NAT2 *5A | GAATCTGG5ATC6GGACCAA Sequence ID No. 2 |
| B9414 | FAM propo dU, NAT2 *5A | GAATC5GGTATC6GGACCAA Sequence ID No. 3 |
| TB0993 | FAM propargyl dU, NAT2 *5A | GAATC5GGTACC6GGACCAA3P Sequence ID No. 4 |
| TB0994 | FAM propargyl dU, NAT2 *5A | GAATC5GCTACC6GGACCAA3P Sequence ID No. 5 |
| F17830 | dU C6 FAM, NAT2 *5A | GATTTGGTCCAGG5ACCAGA6TC3P Sequence ID No. 6 |
| F17831 | dU FAM, NAT2 *5A | GATTTGGTCCAGG5ACCAGA6TC3P Sequence ID No. 7 |
| F17832 | dU C6 FAM, NAT2 *5A | GAT5TGGTCCAGG6ACCAGATTC3P Sequence ID No. 8 |
| F17833 | dU FAM, NAT2 *5A | GAT5TGGTCCAGG6ACCAGATTC3P Sequence ID No. 9 |
| F17834 | dU C6 FAM, NAT2 *5A | GAGAGGAATC5GGTACC6GGACC3P Sequence ID No. 10 |
| F17835 | dU C6 FAM, NAT2 *5A | GAATC5GGTACT6GGACCAA3P Sequence ID No. 11 |
| F17836 | dU C6 FAM, NAT2 *5A | C5TGAACC6CGAACAATTGAAG3P Sequence ID No. 12 |
| F17837 | dU C6 FAM, NAT2 *5A | CTTGAACC5CGAACAA6TGAAG3P Sequence ID No. 13 |
| F17838 | dU C6 FAM, NAT2 *6 | CTTGAACC5CGAACAAT6GAAG3P Sequence ID No. 14 |
| F17839 | dU C6 FAM, NAT2 *6 | CTTCAATTG5TCGAGG6TCAAG3P Sequence ID No. 15 |
| F17840 | dU C6 FAM, NAT2 *6 | CTTCAA5TGTTCGAGG6TCAAG3P Sequence ID No. 16 |
| TaqFLA | dU C6 FAM, NAT2 *6 | CTTCAA5TGTTTGAGG6TCAAG3P Sequence ID No. 17 |
| F17847 | dU C6 FAM, NAT2 *5C | GAAGTGC5GAGAAA6ATATTTAAG3P Sequence ID No. 18 |
| F18140 | dU propargyl FAM, NAT2 *5A | GATTTGGTCCAGG5ACCAGA6TC3P Sequence ID No. 19 |
| F18141 | dU propargyl FAM, NAT2 *5A | GAT5TGGTCCAGG6ACCAGATTC3P Sequence ID No. 20 |
| F34324 | FAM cap prop dU, NAT2 *5A | GAATC5GGTACC6GGACCAA3P Sequence ID No. 21 |
| F34325 | FAM cap prop dU, NAT2 *5A | GAATC5GGTACT6GGACCAA3P Sequence ID No. 22 |
| 2D63A | dU C6 FAM, CYP2D6 *3 | CCCAGG5CATCCTG6GCTCAG3P Sequence ID No. 23 |
| 2D64A | dU C6 FAM, CYP2D6 *4 | GGGGCGTCC5GGGGG6GG3P Sequence ID No. 24 |

TABLE 3

SNPs within N-acetyltransferase (NAT2) and Cytochrome P450 encoding (CYP2D6, CYP2C9 and (CYP2C19) genes were used to aid the design of HyBeacon assays. The types of polymorphism, the allele names and the sequences of F HyBeacon probes used in SNP discrimination assays are included. Bold and underlined characters in HyBeacon sequences represent the polymorphic nucleotide and the fluorophore labelled uracil respectively (F = FAM dU, E = TET dU and H = HEX dU). 3P and 3O represent 3' phosphate and 3'-octanediol respectively.

| Gene | Polymorphism | Allele | HyBeacon | Sequence (5' → 3') |
|---|---|---|---|---|
| NAT2 | $C_{481} \rightarrow T$ | *4 (F1) | 2303002 | GAGAGGAATCFGGTACCTGGACC3P Sequence ID No. 25 |
| | | *5A (S1k) | NAT2*5 | GAGAGGAATCFGGTACTTGGACC3P Sequence ID No. 26 |
| NAT2 | $A_{803} \rightarrow G$ | *4 (F1) | DdeFL1*4 | GAAGTGCFGAAAAATATATTTAAG3P Sequence ID No. 27 |
| | | *5C (S1d) | DdeFL1 | GAAGTGCFGAGAAATATATTTAAG3P Sequence ID No. 28 |
| | | *4 (F1) | DdeFL1*4T | GAAGTGCEGAAAAATATATTTAAG3O Sequence ID No. 29 |
| NAT2 | $G_{590} \rightarrow A$ | *4 (F1) | TaqFL2 | CTTCAAFTGTTCGAGGTTCAAG3P Sequence ID No. 30 |

TABLE 3-continued

SNPs within N-acetyltransferase (NAT2) and Cytochrome P450 encoding (CYP2D6, CYP2C9 and (CYP2C19) genes were used to aid the design of HyBeacon assays. The types of polymorphism, the allele names and the sequences of F HyBeacon probes used in SNP discrimination assays are included. Bold and underlined characters in HyBeacon sequences represent the polymorphic nucleotide and the fluorophore labelled uracil respectively (F = FAM dU, E = TET dU and H = HEX dU). 3P and 3O represent 3' phosphate and 3'-octanediol respectively.

| Gene | Polymorphism | Allele | HyBeacon | Sequence (5' → 3') |
|---|---|---|---|---|
| NAT2 | $G_{857}$ → A | *4 (F1) | BamFL1 | CCTGGTGAFGGATCCCTTAC3P Sequence ID No. 31 |
|  |  | *7A (S3) | BamFL1*7 | CCTGGTGAFGAATCCCTTAC3P Sequence ID No. 32 |
| CYP2D6 | Deletion $A_{2637}$ | *1 | 2D63C* | CCCAGGFCATCCTGTGCTC3P Sequence ID No. 33 |
|  |  | *1 | 2D63B | CCCAGGFCATCCTGTGCTCAG3P Sequence ID No. 34 |
|  |  | *3 | 2D63C | CCCAGGFCATCCGTGCTC3P Sequence ID No. 35 |
| CYP2D6 | $G_{1934}$ → A | *1 | 2D64C* | GGGCGFCCTGGGGGTG3P Sequence ID No. 36 |
|  |  | *1 | 2D64B | GGGGCGFCCTGGGGGTGGG3P Sequence ID No. 37 |
|  |  | *4 | 2D64C | GGGCGTCTFGGGGGTG3P Sequence ID No. 38 |
|  |  | *1 | 2D64E | GGGCGHCCTGGGGGTG3O Sequence ID No. 39 |
| CYP2C9 | $C_{430}$ → T | *1 | C9*2C | CATTGAGGACCGFGTTCAAG3P Sequence ID No. 40 |
|  |  | *2 | C9*2T | CATTGAGGACTGFGTTCAAG3P Sequence ID No. 41 |
| CYP2C9 | $A_{1075}$ → C | *1 | C9*3A | GAAGGFCAATGTATCTCTGG3P Sequence ID No. 42 |
|  |  | *3 | C9*3C | GAAGGFCAAGGTATCTCTGG3P Sequence ID No. 43 |
| CYP2C19 | $G_{681}$ → A | *1 | C19m1G | GATTATTFCCCGGGAACCC3P Sequence ID No. 44 |
|  |  | *2 | C19m1A | GATTATTFCCCAGGAACCC3P Sequence ID No. 45 |
| CYP2C19 | $G_{636}$ → A | *1 | C19m2G | TACCFGGATCCAGGGGTG3P Sequence ID No. 46 |
|  |  | *3 | C19m1A | TACCFGGATTCAGGGGTG3P Sequence ID No. 47 |

TABLE 4

Oligonucleotide primers used to amplify polymorphic target sequence

| Polymorphism |  | Primer Sequence |
|---|---|---|
| NAT2*5A | 195991 | 5'(CTGCTCTCTCCTGATTTGGTCC)3' Sequence ID No. 48 |
| NAT2*5A | 195993 | 5'(CCTCTAGAATTAATTTCTGGG)3' Sequence ID No. 49 |
| NAT2*5C | DdeF2 | 5'(CCTATAGAAAATTCAATTATAAAG)3' Sequence ID No. 50 |
| NAT2*5C | DdeR | 5'(CACGAGATTTCTCCCCAAGG)3' Sequence ID No. 51 |

TABLE 4-continued

Oligonucleotide primers used to amplify polymorphic target sequence

| Polymorphism | Primer | Sequence |
|---|---|---|
| NAT2*6 | TaqF2 | 5'(CCTGCCAAAGAAGAAACACC)3'<br>Sequence ID No. 52 |
| NAT2*6 | TaqR2 | 5'(GTATTCATAGACTCAAAATCTTC)3'<br>Sequence ID No. 53 |
| NAT2*7A | BamF2 | 5'(GAAGAGGTTGAAGAAGTGCTG)3'<br>Sequence ID No. 54 |
| NAT2*7A | BamR | 5'(CAAGGGTTTATTTTGTTCCTTATTC)3'<br>Sequence ID No. 55 |
| CYP2D6*3 | 2D63F | 5'(CCACCGTGGCAGCCACTCTC)3'<br>Sequence ID No. 56 |
| CYP2D6*3 | 2D63R | 5'(CCAGCTGGATGAGCTGCTAAC)3'<br>Sequence ID No. 57 |
| CYP2D6*4 | 2D64F2 | 5'(CGAAGCGGCGCCCGCAGG)3'<br>Sequence ID No. 58 |
| CYP2D6*4 | 2D64R2 | 5'(GGGACGGGGAAGGCGACC)3'<br>Sequence ID No. 59 |

(iii) Heterogeneous Melting Analysis of SNPs.

PCR volumes were typically 30 µl, containing approximately 200 ng of DNA template, 1×PCR buffer (Pharmacia), 0.5 µM each primer, 1 unit Taq polymerase (Amersham Pharmacia Biotech) and 1 mM dNTPs (Amersham Pharmacia Biotech). Following a denaturation reaction step (94° C. 5 min), PCR targets were amplified using 40 cycles comprising denaturation (94° C. 30 s), primer annealing (50° C. 1 min) and extension of products (72° C. 1 min). Following amplification, PCR products were precipitated with 0.1 volumes of 3M sodium acetate and 2 volumes of ethanol. After 10 minutes incubation at −20° C., 30 minutes centrifugation at 13,000 r.p.m. and two wash steps with 70% ethanol, pellets were resuspended in 1× hybridisation buffer/probe mix (50 mM Tris pH7.4, 3 mM $MgCl_2$, appropriate HyBeacon), where 5 µl of buffer/probe mix was added per initial PCR reaction. F-Q HyBeacons were typically used at concentrations between 500 nM-1 µM, whilst F HyBeacons were used between 100 nM and 300 nM concentrations. 5 µl reaction volumes were analysed with a LightCycler™ (Roche) using a melting curve analysis program. Hybridisation analysis comprised an initial fluorescence read (30° C. for 30 s), hybridisation (94° C. for 1 min followed by 30° C. for 2 min), normalisation (65° C. for 1 s, 85° C. for 1 s, 30° C. 1 s) and melt analysis (30° C. to 95° C., with a 0.1° C./s transition rate). With the exception of normalisation, which used single fluorescence acquisitions, fluorescence was monitored continuously. Melting curves were constructed using the LightCycler software, by plotting the negative derivative of fluorescence with respect to temperature (−dF/dT on the y-axis) against temperature (x-axis).

(iv) Homogeneous 'Real-Time' PCR Amplification Assays

PCR volumes were 20 µl, containing 2 µl of 50% saliva or approximately 200 ng genomic DNA, 1× Z-Taq™ buffer (TaKaRa) or 1× HyBeacon PCR buffer (10 mM Tris.Cl pH 8.8, 25 mM KCl, 3.5 mM $MgCl_2$, 5 ng/µl BSA), 0.5 µM primers, 1 unit Taq polymerase (Amersham Pharmacia Biotech) and 1 mM dNTPs. 'Real-time' PCR assays, that utilised fluorescent probes to monitor the accumulation of amplified target, also contained an additional 500-1000 nM or 100-300 nM of the appropriate F-Q and F HyBeacon/s respectively. Polymorphic target sequences were amplified with LightCycler™ (Roche) and ABI PRISM® 7700 Sequence Detector (Applied Biosystems) instruments. Reactions, performed in LightCycler capillaries, were denatured by incubation at 95° C. for 1 min (genomic and plasmid DNA) or 5-10 min (saliva samples), prior to amplification of polymorphic targets using 40-50 cycles, comprising denaturation (95° C. 0 s), primer annealing (Faq 10 s) and extension of products (72° C. 10 s). Fluorescence acquisition was performed at the end of each primer annealing step. The fluorescence acquisition temperature (Faq) varies between amplicons and HyBeacons, where Faq is approximately midway between matched and mismatched probe Tms (see table 5). For example, 2D64C* HyBeacon assays employ a 57° C. Faq to discriminate CYP2D6*1 and *4 SNPs by real-time amplification. Following amplification, reactions were denatured (95° C. 0 s) and cooled (35° C. 2 min) prior to melt analysis (35° C. to 95° C., with a 0.1° C./s transition rate), where fluorescence was acquired continuously. Melt peaks were constructed using LightCycler software, by plotting the negative derivative of fluorescence with respect to temperature (−dF/dT on the y-axis) against temperature (x-axis).

(v) Asymmetric Amplification of HyBeacon Targets.

Asymmetric PCR was used to generate single-stranded DNA target molecules for probe hybridisation. Amplifications were performed in LightCycler capillaries. Anti-sense primers were employed to amplify the single-stranded product containing the homologous DNA sequence required for HyBeacon hybridisation. Sense primers were involved with the initial amplification of double-stranded DNA to generate the strand that did not contain the probe-binding site. Anti-sense and sense primers were typically used at a ratio of 50:1. pGEM-T plasmids containing polymorphic NAT2 and CYP2D6 targets were used as PCR templates. PCR reaction volumes were typically 20 µl, containing approximately 200 ng of plasmid DNA, 1× Z-Taq™ PCR buffer (TaKaRa), 0.5 µM anti-sense primer, 10 nM sense primer, 1 unit Taq polymerase (Amersham Pharmacia Biotech), 1 mM dNTPs (Amersham Pharmacia Biotech) and the appropriate hybridisation beacon. Homogeneous amplification and melting peak analysis was performed as described above.

(vi) Solid Phase Analysis of Polymorphic Targets.

PCR amplification was performed as described above for the heterogeneous assays, with the exception that the anti-sense primer was biotinylated at the 5' terminus. Following amplification, 10-15 µl of biotinylated PCR product was added to individual wells of streptavidin coated microtitre plates (Hybaid). 1×DASH buffer gold (Hybaid) was added to each well to yield a final volume of 50 µl. Following a 1-hour incubation at room temperature, the solution was removed from each well. 50 µl 0.1 M NaOH was added to wells to denature double-stranded DNA. After 5 minutes incubation, wells were washed once with 50 µl 0.1 M NaOH and twice with 50 µl 1×DASH buffer to remove the non-biotinylated DNA strand. An excess of HyBeacon (>1 µM) in 1×DASH buffer (2 µl probe+48 µl buffer) was added to each well. Probes were hybridised to immobilised single-stranded DNA by heating reactions to 95° C. for 1 minute then cooling to 25° C. at an approximate rate of 0.08° C./sec. Solution and unhybridised probe was removed from wells and replaced with 50 µl of fresh 1×DASH buffer. Melting analysis of hybridised probe was performed on a DASH (Dynamic Allele Specific Hybridisation) instrument (Hybaid) using temperature transition rates between 0.02-0.07° C./sec.

(vii) Multiplex HyBeacon Target Detection

Reactions containing multiple primer pairs and HyBeacon probes were performed using the ABI PRISM® 7700

Sequence Detector. NAT2*4 (*7A locus), NAT2*4 (*5C locus) and CYP2D6*1 polymorphic targets were amplified and detected using FAM, TET and HEX labelled HyBeacon probes respectively (table 4). Following a denaturation reaction step (95° C. 5 min), polymorphic targets were amplified from genomic DNA using 40 cycles, comprising denaturation (95° C. 15 s), primer annealing (50° C. 30 s) and extension of products (72° C. 30 s). Fluorescence acquisition was performed during each primer annealing step of amplification.

Results and Discussion (i) The Polymorphic Target Sequences.

The human N-acetyltransferase 2 (NAT2) locus has been demonstrated to be polymorphic. Defective copies of the NAT2 gene are known to result in slow acetylation of several arylamine drugs and toxicants. Epidemiological studies have associated this slow acetylation phenotype with a risk for bladder and colorectal cancers. Analysis of polymorphic NAT2 loci has identified a number of slow alleles, containing nucleotide substitutions (see Table 1). These substitutions include point mutations at positions 481 (C to T), 590 (G to A), 803 (A to G) and 857 (G to A), which produce *5A, *6, *5C and *7A restriction fragment length polymorphisms (RFLPs) respectively. At each of these polymorphic loci, *1 is the allelic variant which occurs more frequently in human genomes.

The Cytochrome P450 enzyme (debrisoquine 4-hydroxylase), encoded by the genes such as CYP2D6, CYP2C9 and CYP2C19 in humans, is responsible for the metabolism of more than 30 commonly prescribed drugs, including antidepressants, anti-arrhythmics and anti-hypertensive agents. Approximately 5-10% of Caucasians exhibit a poor metabolism phenotype due to deficient activity of the cytochrome P450 enzyme. Many allelic variants have been identified in the CYP2D6 gene locus, the most common of which being the CYP2D6*3 (also known as CYP2D6A) and CYP2D6*4 (also known as CYP2D6B) single nucleotide polymorphisms. Individuals possessing *3 and *4 genotypes have been shown to possess poor enzyme activity phenotypes.

The NAT2 and CYP polymorphisms have been used to test the potential of hybridisation beacons to detect specifically amplified DNA sequences and to discriminate targets containing single nucleotide polymorphisms.

(ii) Differential Probe Hybridisation to Oligonucleotide Targets.

When a HyBeacon probe hybridises to a target sequence, the interaction may be either perfectly matched or mismatched. FIG. 1 illustrates the differences between matched, mismatched and double mismatched duplexes, classifying each type of interaction. HyBeacon probes were hybridised to perfectly matched and mismatched oligonucleotides and analysed in a LightCycler. When the quantities of fluorescence emitted from HyBeacons in single-stranded and double-stranded states were compared, it was observed that significantly more fluorescence was emitted when probes were hybridised to target molecules than when free in solution. These differences in fluorescence emission, generated by single-stranded and double-stranded HyBeacon probes, were statistically significant ($p<0.01$ in single-factor ANOVA) and provided a method by which the presence of target DNA could be detected through fluorescence quantitation (FIG. 2).

Monitoring the changes in fluorescence emission caused by alterations in temperature and probe hybridisation status allows the generation of melting peaks with HyBeacon/homologue pairs. HyBeacon probes hybridised to mismatched oligonucleotides produce melt curves with reduced Tms compared with probes hybridised to fully complementary target molecules. FIG. 2 demonstrates the differential hybridisation of a NAT2*4 HyBeacon (at the *5A SNP) to matched and mismatched oligonucleotide targets. Regions of mismatch reduce probe Tm and allow discrimination of polymorphic targets through melt peak analysis. Matched, single mismatched and multiple mismatched targets may be reliably discriminated by melt peak Tm. Furthermore, fluorescence acquisition performed at a temperature midway between matched and mismatched Tms allows discrimination of polymorphic targets on the basis of fluorescence quantitation. At the fluorescence acquisition temperature, the matched HyBeacon is hybridised to its target and is emitting more fluorescence than a mismatched probe that has melted away from its target (FIG. 2).

In solution, HyBeacons only emit small amounts of background fluorescence. However, upon binding to target sequences, significantly more fluorescence is emitted as a direct result of hybridisation. It has been demonstrated that sequences differing by as little as a single nucleotide may be distinguished by (i) the amount of fluorescence produced when the hybridisation beacon molecule hybridises to its target sequence and (ii) the melting temperature (Tm) of the probe/target duplex.

Fluorescence quantitation and melting analysis methods have been performed with F-Q and F HyBeacon probes, generating results of comparable quality. FIG. 3 illustrates melting curves derived from F and F-Q NAT2*4 HyBeacons hybridised to oligonucleotide targets. F-Q HyBeacons may have some dependence on fluorophore and quencher spacing and angular disposition effects (data not shown). However, F HyBeacons display elevated levels of fluorescence emission upon target hybridisation despite the absence of a quencher moiety. Fluorophore moieties in F and F-Q HyBeacon probes emit significantly more fluorescence when in the double-stranded state than in the single-stranded conformation (see below).

(iii) Varieties of Single Nucleotide Polymorphisms.

Discrimination of the single base substitution polymorphisms present in the NAT2 and CYP2D6 alleles has been demonstrated using HyBeacon probes. A series of oligonucleotide targets were hybridised to the TB0993 NAT2*4 probe to test the ability of hybridisation beacon molecules to discriminate insertion and deletion (InDel) polymorphisms. Three insertion and three deletion oligonucleotides, varying in type and position of polymorphism, were analysed. Each InDel target generated a significantly reduced Tm compared with HyBeacon hybridised to perfectly matched oligonucleotide (FIG. 4). Similar to substitution polymorphisms, InDels may also be distinguished by the Tms of HyBeacon/target duplexes and the amount of fluorescence emitted at a temperature in-between the Tms of matched and mismatched probe.

(iv) Discrimination of SNPs in PCR Products (Heterogeneous Assays).

Heterogeneous assays, that perform target amplification and SNP discrimination in separate tubes, were carried out with NAT2*5A, *5C and *6 polymorphisms and with CYP2D6*3 and *4 SNPs. Successful heterogeneous assays, allowing reliable SNP discrimination through melt peak analysis, have been developed for all polymorphisms tested. PCR products containing polymorphic nucleotides were amplified from NAT2 and CYP2D6 template DNA. Amplicon sizes ranged between 80 bp and 282 bp in length. PCR products were isolated and resuspended in hybridisation buffer containing HyBeacon probe. Probes were hybridised to PCR targets and melting analyses were performed in Light-Cycler capillaries, generating melt peaks with Tms dependent upon the identity of the PCR target. HyBeacons readily discriminate matched and mismatched PCR targets by the melting temperature of probe/target duplexes. F-Q and F HyBeacon variants both perform well in heterogeneous SNP discrimination assays.

Assays performed with the CYP2D6*3 polymorphism demonstrate how F and F-Q HyBeacons permit SNP discrimination in heterogeneous analyses (FIG. 5). A 119 bp PCR product was amplified from CYP2D6*3 polymorphic DNA. PCR products were isolated and resuspended in hybridisation buffer containing either the 2D63A (F-Q) or 2D63B (F) HyBeacon probes. The 2D64 F HyBeacon was used at a 5 times lower concentration than the F-Q probe because of the larger fluorescence background caused by the lack of quencher. FIG. 5 displays the melting curves derived from HyBeacon hybridisation to PCR targets containing the *1 and *3 CYP2D6 alleles. 2D63A and 2D63B probes possess identical nucleotide sequences, being fully complementary to the *1 allele of the CYP2D6 gene and, therefore, containing a single base mismatch when hybridised to the *3 allele. The 2D63A F-Q HyBeacon generated melt peaks with Tms of approximately 56° C. and 65° C. when hybridised to *3 and *1 allelic sequences respectively. The 2D63B F HyBeacon generated melt peaks with similar Tms of approximately 58° C. and 65° C. when hybridised to mismatched and matched PCR products respectively. The melting temperatures, generated by HyBeacon hybridisation to the two alleles of the SNP, are highly reproducible and statistically significant ($p<0.01$ in single factor ANOVA). Therefore, CYP2D6*1 and *3 genotypes, correlating to normal and deficient enzyme metabolism phenotypes respectively, are reliably discriminated in heterogeneous HyBeacon assays.

(v) Real-Time Detection of Nucleic Acid Sequences.

The amount of fluorescence emitted from HyBeacon probes is significantly greater when the oligonucleotides are hybridised to complementary nucleic acid sequences than when in the single-stranded conformation. Therefore, HyBeacons may be included in reactions to monitor the real-time accumulation of specific DNA targets throughout the course of PCR amplification. FIG. 6 demonstrates detection of CYP2D6*1 sequence present in genomic and saliva DNA, using the 2D64C* HyBeacon to monitor the accumulation of product with each cycle of amplification.

(vi) 'Real-Time' Discrimination of SNPs (HOMOGENEOUS Assays).

When HyBeacon probes hybridise to polymorphic target sequences, interactions may either be perfectly matched or mismatched. Positions of nucleotide mismatch destabilise probe/target duplexes such the Tm of hybridisation is reduced compared with fully complementary sequences. Since the amount of fluorescence emitted from hybridised HyBeacon is significantly greater than single-stranded probe, polymorphic target sequences may be discriminated on the basis of hybridisation Tm. The annealing (and fluorescence acquisition) temperature of PCR may be optimised to accomplish real-time discrimination of closely related DNA sequences, by selective probe hybridisation, such that only target sequences that are fully complementary to HyBeacon probes instigate increased in fluorescent signals during amplification. Polymorphic sequences containing SNPs may be identified using the fluorescence data derived during real-time amplification. For example, if a HyBeacon probe is designed to be fully complementary to a DNA sequence containing a mutation, increases in fluorescence emission are only generated in the presence of the mutant allele.

Figure 7A:
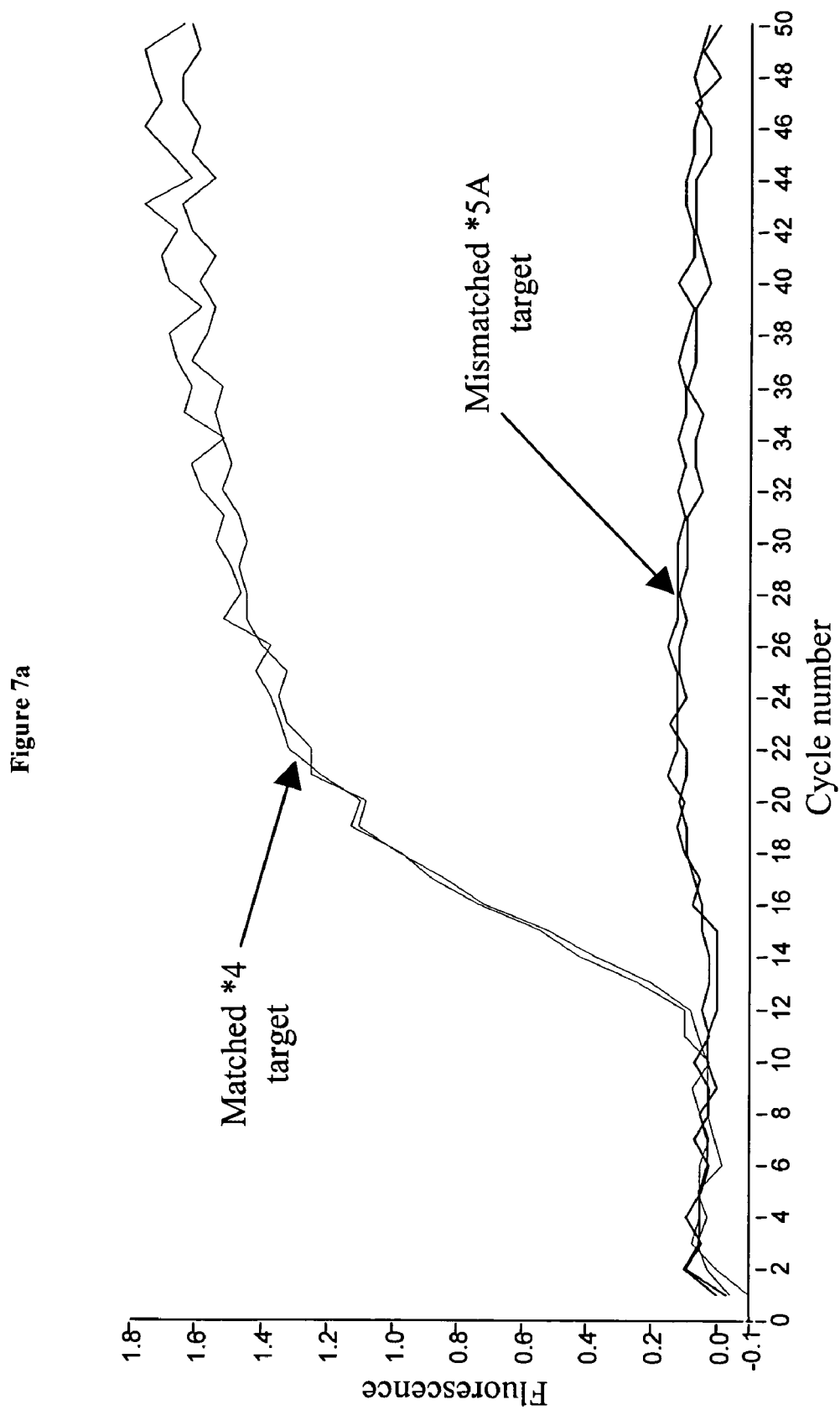

HyBeacon probes were incorporated into polymerase chain reactions designed to amplify NAT2 and CYP polymorphic sequences. At each cycle of amplification, single fluorescence readings were acquired at the primer annealing stage, at a temperature midway between the Tms of matched and mismatched HyBeacon. At the fluorescence acquisition temperature, the HyBeacon is expected to be hybridised to perfectly matched target but is not expected to be hybridised to a mismatched sequence. Differential probe hybridisation, at the fluorescence acquisition temperature, causes reactions containing perfectly matched template to result in fluorescence increases during amplification, whilst reactions containing mismatched template do not yield fluorescence increases. Homogeneous SNP analysis is demonstrated here using the F HyBeacon 0203002, which was employed to discriminate NAT2*4 and *5A polymorphisms. The HyBeacon is perfectly matched to *4 allele of NAT2 and has a single base mismatch when hybridised to *5A sequence. FIG. 7a demonstrates 'real-time' discrimination of SNPs, where only reactions containing the *4 allele generate significant increases in fluorescence emission during PCR cycling. Reactions containing only mismatched *5A alleles do not produce increases in fluorescence emission during amplification.

FIG. 8 is another example of real-time HyBeacon analysis that demonstrates detection and discrimination of polymorphic CYP2D6 *1 and *4 sequences, using plasmid DNAs as the source of template. Discrimination of polymorphic sequences present in genomic DNA and saliva samples may also be achieved by real-time HyBeacon PCR analysis. The 2D64C* HyBeacon, presented in FIG. 8, is perfectly matched to the *1 allele of the CYP2D6 gene and, as such, specifically detects the amplification of the *1 sequence through real-time increases in fluorescence emission. Reactions containing only CYP2D6*1 sequences generate relatively large emission increases whilst samples containing only *4 alleles do not display significant fluorescence increases. Reactions that contain both *1 and *4 alleles display intermediate increases in the quantity of fluorescence emission. Use of the 2D64C HyBeacon, which is fully complementary to the CYP2D6*4 allele, permits confirmation of 2D64C* genotyping results (unpublished data). As with TaqMan™ probes, molecular beacons, hybridisation probes and Scorpion primers, two HyBeacon probes are required to genotype samples, with respect to biallelic SNPs, by real-time PCR to ensure accurate identification of homozygous and heterozygous DNA.

(vii) Discrimination of SNPs by Melting Curve Analysis

Figure 7B:
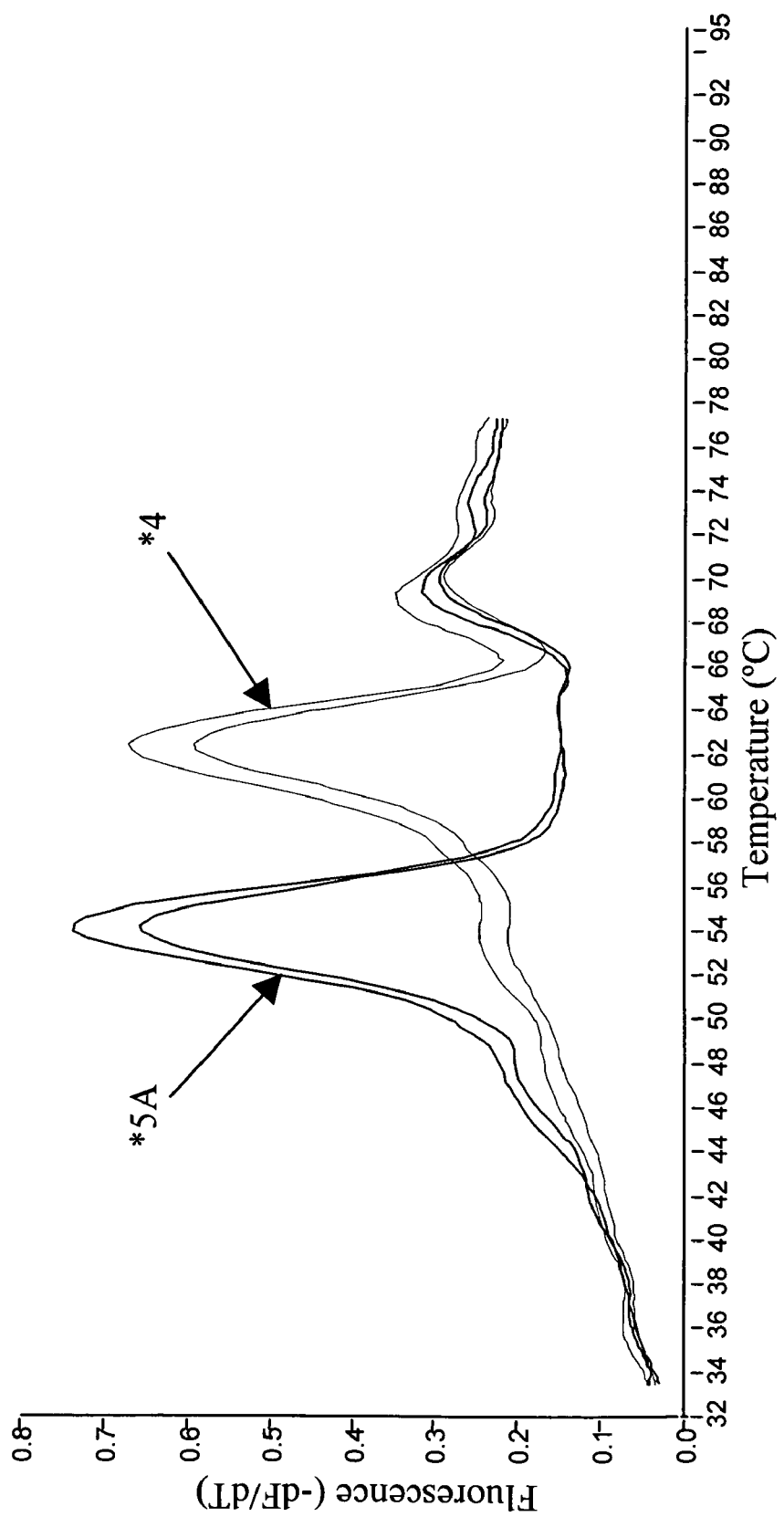

Polymorphic DNA sequences may also be detected and discriminated in an 'end-point' format using HyBeacon probes through melt curve analysis and Tm determination. Homogeneous melting curve analysis of HyBeacon/target duplexes may be performed on LightCycler reactions immediately following amplification. The melting temperatures derived from melt curve analysis permits identification of target DNA sequences, where Tms derived from fully complementary HyBeacons are significantly greater than mismatched probe interactions. Melting analysis performed post-amplification with the 0203002 HyBeacon and the *4 and *5A polymorphic targets generated melt peaks possessing Tms of approximately 62° C. and 54° C. with matched and mismatched sequences respectively (FIG. 7b). Melt peak Tms, produced by hybridisation with matched and mismatched target sequences, are highly reproducible for a given SNP and significantly different between SNPs. Therefore, reliable discrimination of SNPs is achieved by analysis of HyBeacon melting temperatures. Post-amplification melting analysis permits validation of 'real-time' fluorescence data, confirming that the presence or absence of fluorescence increases in PCR are actually correlated with the presence of matched or mismatched targets respectively. Therefore, post-amplification melts permit differentiation between reactions that do not produce fluorescence increases because of the presence of mismatched target and those reactions that do not generate fluorescence increases due to the total absence of target or a failure of PCR amplification. Both F-Q and F HyBeacon variants have been demonstrated to perform well in 'real-time' amplification assays and to generate post-amplification melting curves in homogeneous assays. However, F HyBeacons have been found to typically produce superior quality post-amplification melts compared with F-Q probes of identical DNA sequences.

With F HyBeacon probes, homozygous samples generate single melt peaks, which are matched or mismatched depending on the identity of the target sequence, whilst heterozygous DNA produce melting traces that possess both matched and mismatched peaks. FIG. 9 demonstrates detection and discrimination of polymorphic CYP2D6*1 and *4 sequences, amplified from genomic DNA samples, by melt peak analysis. The 2D64C* HyBeacon generates a single melt peak possessing a Tm of approximately 60° C. when hybridised to homozygous DNA containing fully complementary *1 alleles. Mismatched probe hybridisation to homozygous *4 samples results in a single melt peak with a Tm of approximately 49° C. Heterozygous samples, containing both *1 and *4 alleles, generate traces possessing both 60° C. and 49° C. melt peaks.

(viii) Identification of Homozygous and Heterozygous Samples.

It is considered important that a technology for scoring SNPs is capable of identifying whether a sample is homozygous or heterozygous for a particular allele. Heterozygote analysis utilising F-Q HyBeacons has been found to require two distinct probes, perfectly matched to the two alleles of an SNP, for the identification of heterozygous samples. Two HyBeacons are thought to be necessary since F-Q probes have been found to typically generate only matched melting peaks in reactions containing a mixture of fully complementary and mismatched targets. The mismatched melt peaks are not observed in heterozygous reactions, where either binding to fully complementary target is either thermodynamically favoured or melting analysis reveals the matched curve whilst masking the mismatched peak. If the two HyBeacons possessed spectrally distinct fluorophores that could be excited and detected simultaneously, homogeneous heterozygote discrimination assays using F-Q probes could be performed in a single tube. However, at present the LightCycler may only excite fluorescein. Therefore, differential beacon hybridisation analysis using two distinct HyBeacons in the same Light-Cycler capillary was performed using probes possessing significantly different Tms. Two F-Q HyBeacon probes, F17834 and F17835, of different length and Tm were used in isolation and in combination to discriminate homozygous and heterozygous NAT2*4 and *5A samples (FIG. 10). The F17834 and F17835 probes generate matched melting curves possessing Tms of approximately 60° C. and 52° C. when hybridised to homozygous *4 and *5A DNA respectively. When the F17834 and F17835 HyBeacons are used in combination with a mixed DNA, containing *4 and *5A sequences (heterozygote), two melt peaks possessing Tms of approximately 59° C. and 52° C. are generated in the same melting trace. The presence of two peaks within a single melting trace may be employed as an indicator of heterozygosity.

An important feature of the F HyBeacon technology is that, unlike F-Q probes and previously reported flourescent probes, homozygous and heterozygous samples may be reliably identified using a single F HyBeacon. Fluorescent probes, such as TaqMan™ probes, molecular beacons and Scorpion primers, typically require two probes to reliably detect and discriminate bialleleic sequences by real-time PCR methods. Furthermore, hybridisation probes require a pair of fluorescent oligonucleotides to identify homozygous and heterozygous DNA by melting curve analysis. HyBeacon probes may reliably distinguish homozygous and heterozygous samples through melting curve analysis by Tm determination and the number of melt peaks generated. FIGS. 9 and 11 demonstrate identification of homozygous and heterozygous samples by melt peak analysis, where homozygous samples are identified by specific Tms and heterozygotes by the presence of two peaks with a single melting trace. FIG. 11 illustrates the melting curves derived from a NAT2*5C F HyBeacon (DdeFL1) hybridised to homozygous and heterozygous DNA targets. In homogeneous and heterogeneous assays, DdeFL1 generates single melting peaks with Tms of approximately 54° C. and 47° C. with homozygous matched (*5C) and mismatched (*4) targets respectively. Samples heterozygous for the *4 and *5C alleles were found to generate both the matched and mismatched peaks within a single melting trace. Therefore, the presence of two peaks within a HyBeacon melting trace permits reliable identification of heterozygous samples.

The ability to detect heterozygous DNA using HyBeacon probes depends on the magnitude of the ΔTm (the difference in Tm between fully complementary and mismatched hybridisation). Table 5 illustrates the Tm and ΔTm values displayed by HyBeacon probes during hybridisation to NAT2 and CYP polymorphic genes. A probe that permits reliable identification of homozygous and heterozygous samples by melt peak analysis has been developed for each of the nine SNPs investigated here. It is apparent that ΔTm values exceeding approximately 5.2° C. are required to reliably detect the presence of heterozygous DNA by melting curve analysis. The ΔTm of hybridisation depends on the length of the probe, the position of the nucleotide mismatch and the identity of the mismatch. The length of HyBeacon oligonucleotides should be sufficient enough to ensure specificity of hybridisation, but should not be excessive causing insensitivity to mismatch. HyBeacons should be designed such that polymorphic nucleotides are located towards the centre of probes since mismatches at central positions have greater affects on Tm than mismatches located at oligonucleotide termini. All nucleotide mismatches exhibit destabilising affects on hybridisation Tm, but the magnitude of destabilisation depends on the type of mismatch interaction. Mismatched interactions involving G (i.e. G/T, G/A and G/G) are the most stable at room temperature and mismatches containing C (i.e. C/T, C/A and C/C) are the least stable. Therefore, to maximise the affect of mismatch on ΔTm, mismatches involving G are avoided and mismatches containing C are pursued.

TABLE 5

The Tm and ΔTm values derived from HyBeacon hybridisation to NAT2 and CYP sequences, including the matched and mismatched nucleotide interactions occurring at the polymorphic position. Tm values were obtained from several independent analyses to account for experimental variation and the mean and standard error values are included. Values in italics were derived from hybridisation to oligonucleotides. The ability to identify heterozygous DNA is dependent on the ΔTm and is identified by the presence of both matched and mismatched melt peaks in a single melting trace.

| HyBeacon | Nucleotide interactions | Matched Tm (mean ± SE) | Mismatched Tm (mean ± SE) | ΔTm | Identification of heterozygous DNA? |
|---|---|---|---|---|---|
| 2303002 | C/G, C/A | 63.1° C. ± 0.1 | 55.2° C. ± 0.1 | 7.9 | Yes |
| NAT2*5 | T/A, T/G | 61.3° C. ± 0.2 | 57.1° C. ± 0.2 | 4.2 | No |

TABLE 5-continued

The Tm and ΔTm values derived from HyBeacon hybridisation to NAT2 and CYP sequences, including the matched and mismatched nucleotide interactions occurring at the polymorphic position. Tm values were obtained from several independent analyses to account for experimental variation and the mean and standard error values are included. Values in italics were derived from hybridisation to oligonucleotides. The ability to identify heterozygous DNA is dependent on the ΔTm and is identified by the presence of both matched and mismatched melt peaks in a single melting trace.

| HyBeacon | Nucleotide interactions | Matched Tm (mean ± SE) | Mismatched Tm (mean ± SE) | ΔTm | Identification of heterozygous DNA? |
|---|---|---|---|---|---|
| DdeFL1*4 | A/T, A/C | 53.2° C. ± 0.2 | 42.4° C. ± 0.1 | 10.8 | Yes |
| DdeFL1 | G/A, G/T | 54.1° C. ± 0.1 | 47.6° C. ± 0.1 | 6.5 | Yes |
| BamFL1 | G/C, G/T | 57.6° C. ± 0.6 | *(52.4° C.)* | *(5.2)* | (No) |
| BamFL1*7 | A/T, A/C | *(56.7° C.)* | 48.9° C. ± 0.4 | *(7.8)* | (Yes) |
| 2D63C* | T/A, T/Del | 59.2° C. ± 0.1 | 53.2° C. ± 0.1 | 6.0 | Yes |
| 2D63C | G/C, G/Ins | 59.3° C. ± 0.1 | 52.8° C. ± 0.1 | 6.5 | Yes |
| 2D64C* | C/G, C/A | 60.4° C. ± 0.1 | 49.3° C. ± 0.1 | 11.1 | Yes |
| 2D64C | T/A, T/G | 56.8° C. ± 0.6 | 53.2° C. ± 0.4 | 3.6 | No |
| C9*2C | C/G, C/A | 57.8° C. ± 0.1 | 48.2° C. ± 0.2 | 9.6 | Yes |
| C9*2T | T/A, T/G | 54.8° C. ± 0.1 | 52.1° C. ± 0.1 | 2.7 | No |
| C9*3A | T/A, T/C | 54.5° C. ± 0.1 | 45.5° C. ± 0.2 | 9.0 | Yes |
| C9*3C | G/C, G/A | 56.3° C. ± 0.2 | 50.9° C. ± 0.1 | 5.4 | Yes |
| C19m1G | G/C, G/T | 54.4° C. ± 0.1 | 48.7° C. ± 0.2 | 5.7 | Yes |
| C19m1A | A/T, A/C | 52.9° C. ± 0.3 | 45.0° C. ± 0.1 | 7.9 | Yes |
| C19m2G | C/G, C/A | 57.5° C. ± 0.2 | 47.0° C. ± 0.2 | 10.5 | Yes |
| C19m2A | T/A, T/G | *(56.6° C.)* | 51.5° C. ± 0.3 | *5.1* | *(No)* |

(ix) Multiplex Analysis of SNPs.

Figure 12A:
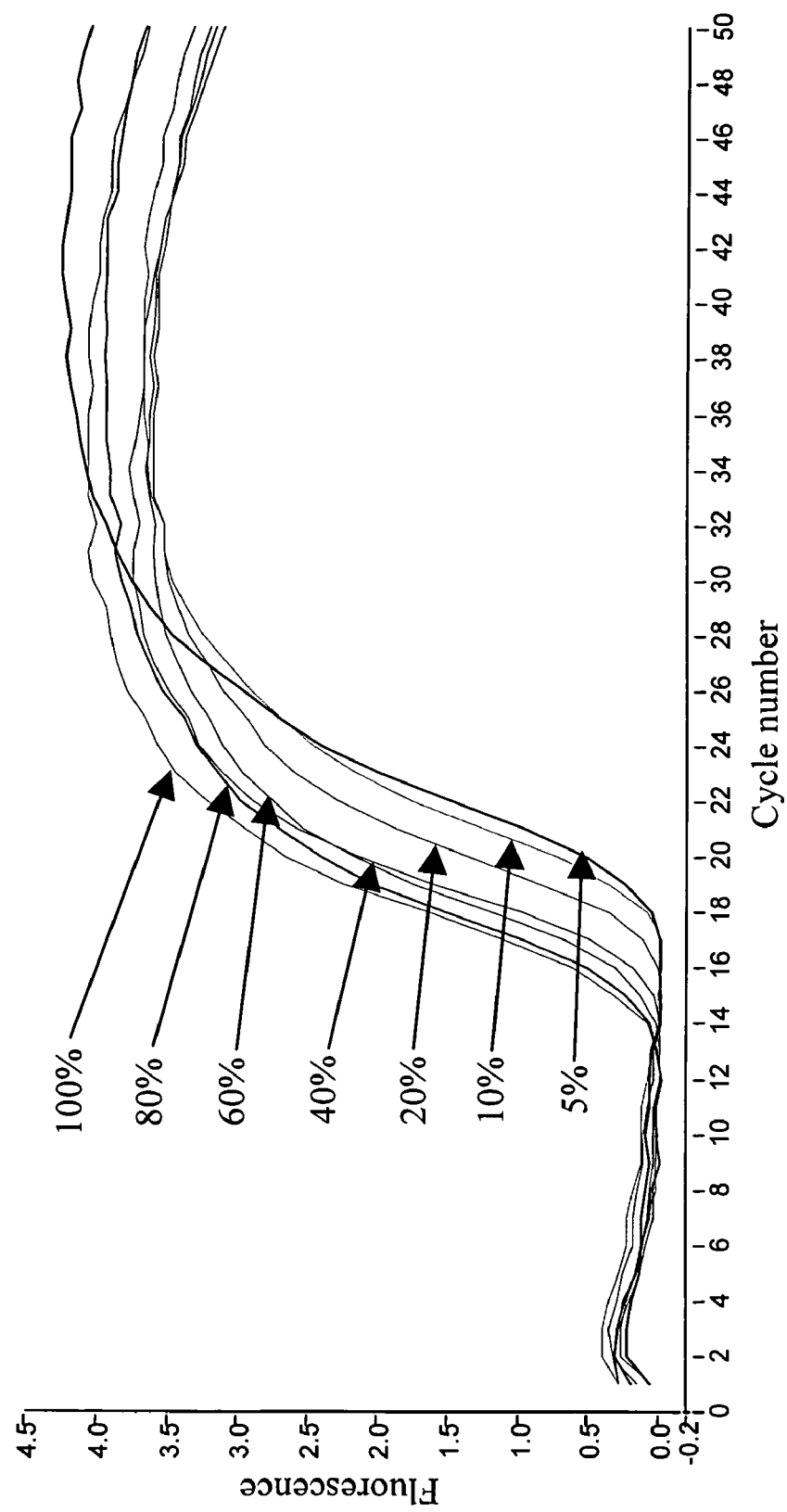
Figure 12B:
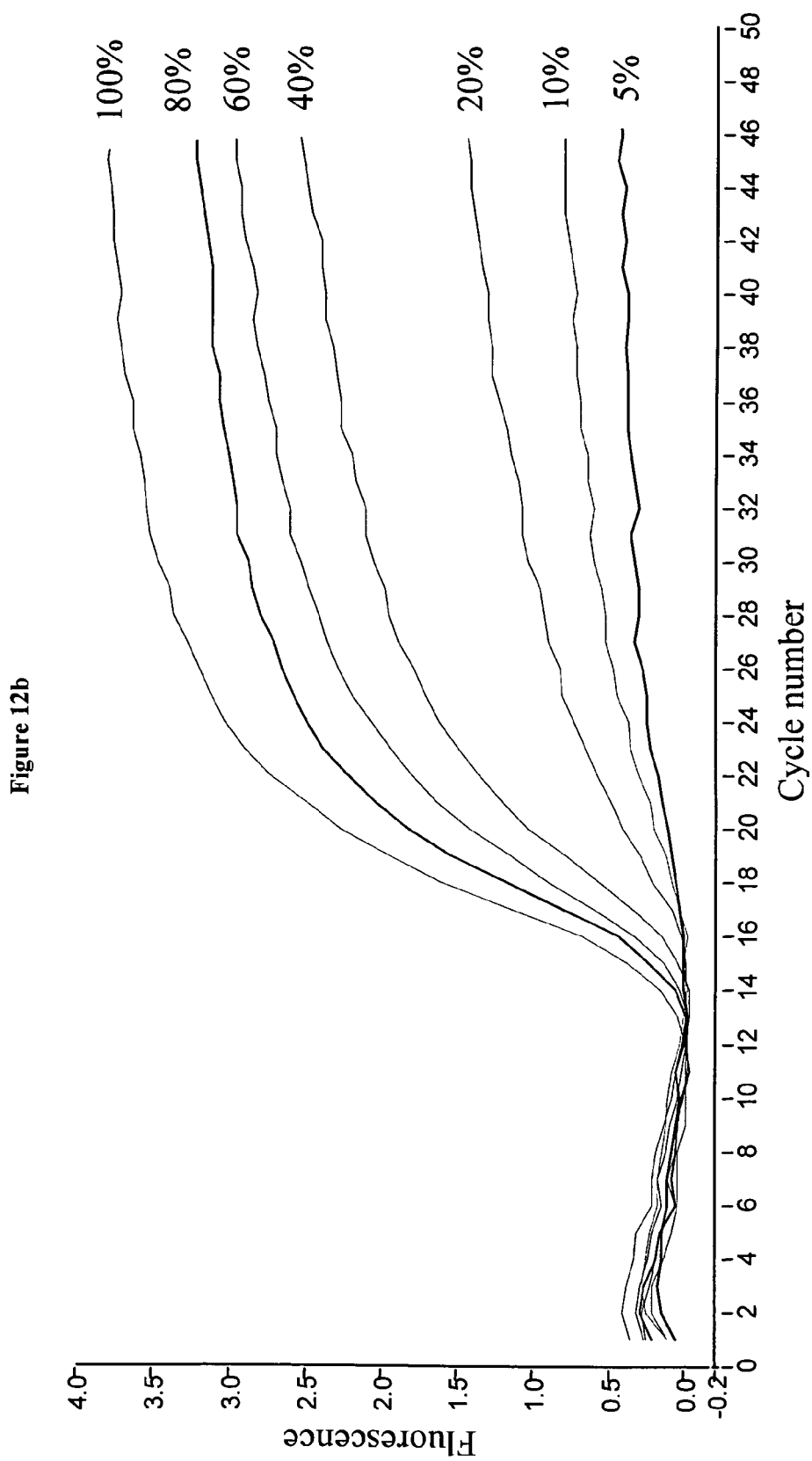

The potential for multiplex analysis using HyBeacon probes has been examined using mixtures of specific and non-specific PCR targets. HyBeacons hybridise to specific DNA targets amplified throughout PCR, resulting in increases in fluorescence emission. Increases in HyBeacon fluorescence emission do not occur with non-specific DNA targets that lack the probe's target sequence. Different proportions of specific and non-specific PCR templates (100, 80, 60, 40, 20, 10 and 5% specific sequence in non-specific DNA) were analysed in homogeneous assays to test the ability of the 2D64B HyBeacon probe to detect the amplification of specific target. In reactions that amplified only the specific target, i.e. no non-specific amplification, all starting concentrations of specific target were readily detected, with equivalent increases in fluorescence emission (FIG. 12a). However, when both specific and non-specific targets were amplified in the same reaction, the ability of the probe to detect specific amplification decreased as the proportion of specific PCR template was reduced (FIG. 12b). The results derived from this experiment suggest that HyBeacon multiplex assays containing up to four or five distinct targets may be possible. However, the use of increased signal fluorophores and higher sensitivity detection instruments may allow multiplex analysis to be extended past five targets.

Figure 13A:
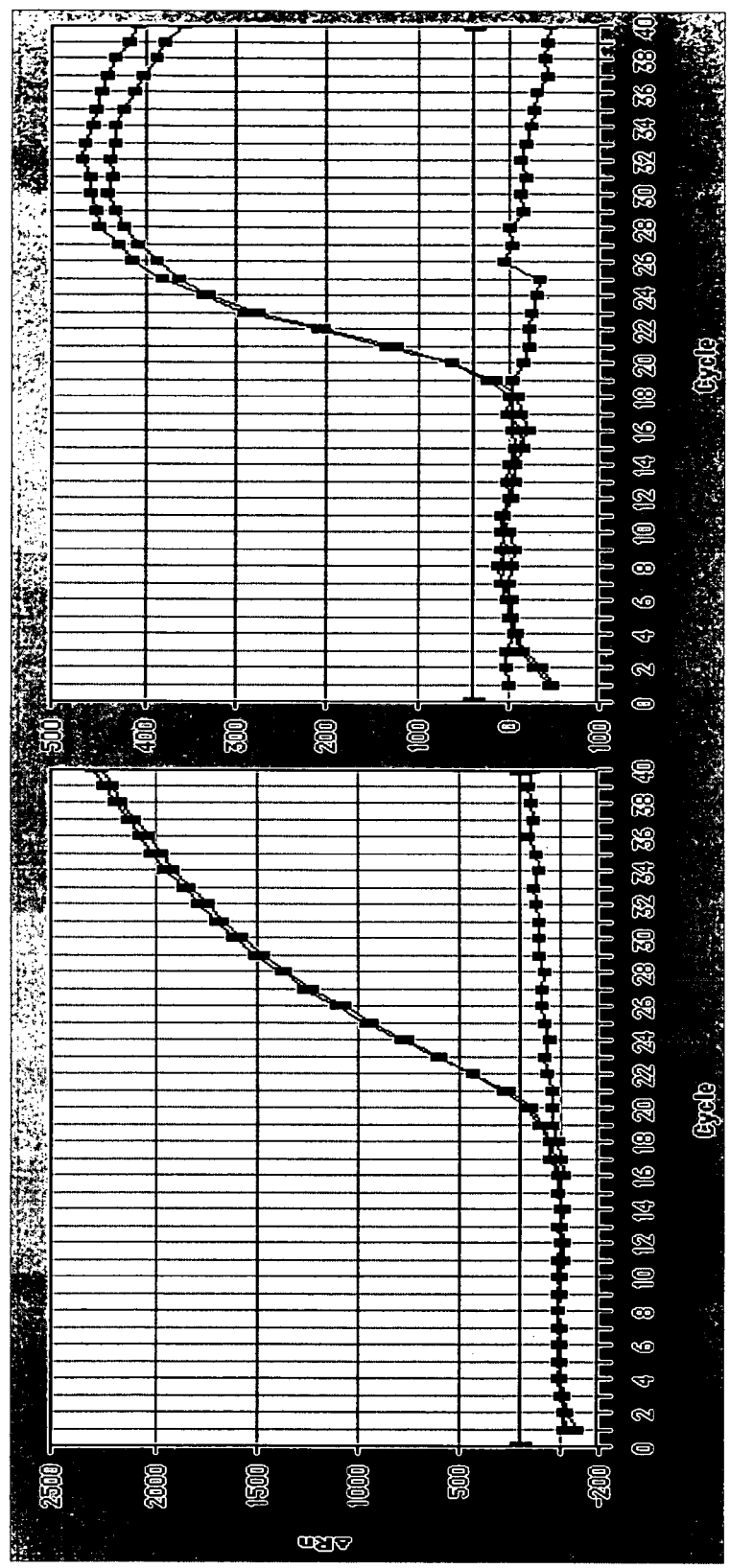
Figure 13B:
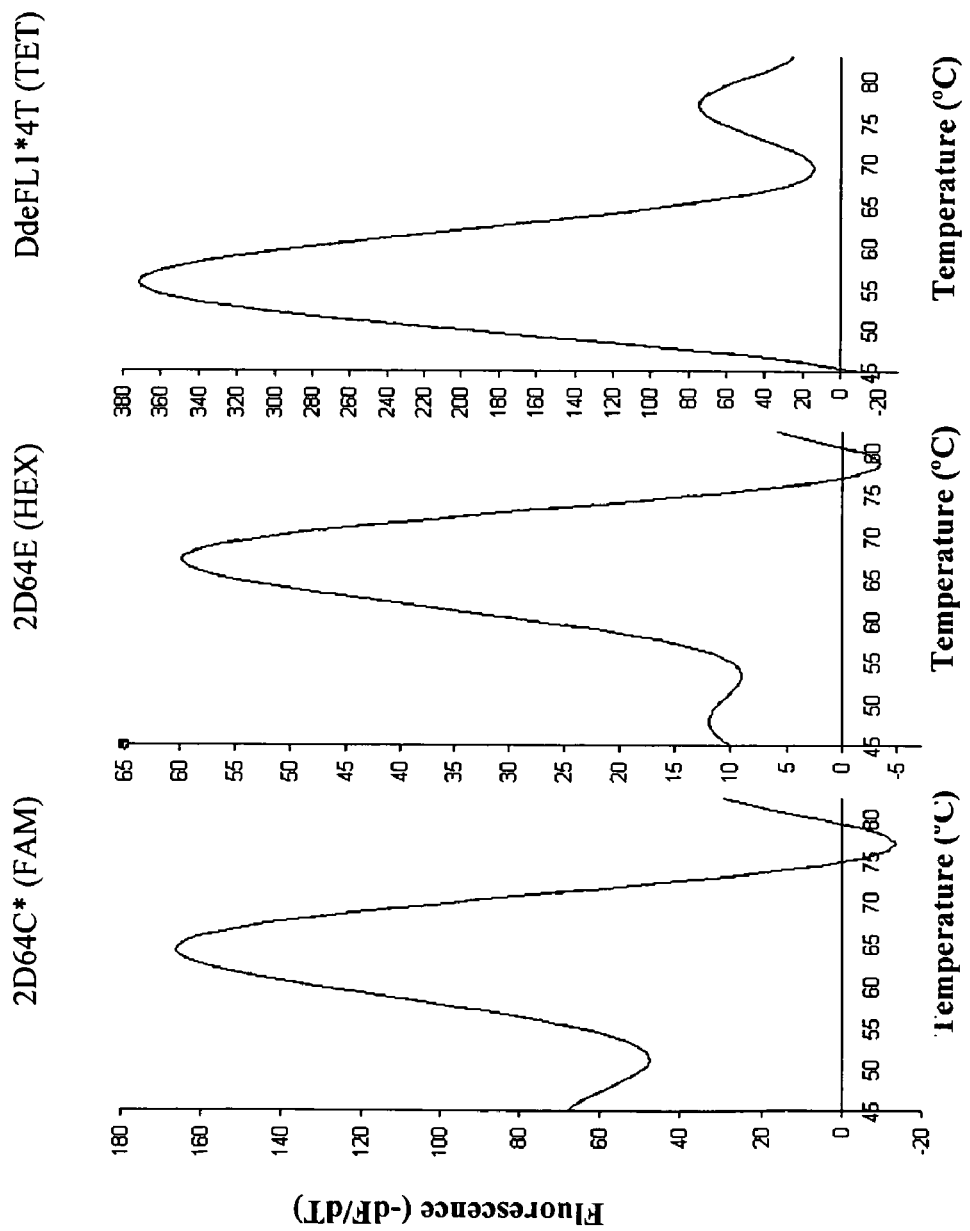

Functionality of HyBeacon probes has been demonstrated to date using FAM, HEX and TET fluorescent dyes, where each hybridised probe emits significantly greater amounts of fluorescence than single-stranded HyBeacons. Multiple polymorphic sequences may be simultaneously amplified, detected and discriminated with these spectrally distinct HyBeacons using real-time PCR and melting peak analyses. FIG. 13a demonstrates simultaneous amplification and specific detection of NAT2*4 and CYP2D6*1 alleles, in a single ABI PRISM 7700 microtitre plate well, using FAM and HEX labelled HyBeacon probes respectively. The identity of polymorphic sequences may also be determined using FAM, HEX and TET probes by melting temperature determination. An Excel macro was created to convert the melt curve data obtained from the ABI PRISM 7700 to melt peaks. FIG. 13b displays the peaks obtained from 2D64C*, 2D64E and DdeFL1*4T probes labelled with FAM, HEX and TET dyes respectively. Melt peaks have been obtained from HyBeacon hybridisation to complementary oligonucleotides and PCR amplified targets.

(x) Optimisation of HyBeacon assays.

Various HyBeacon assay parameters may be modified to potentially improve the efficiency of target detection and SNP discrimination. Examples of reaction conditions that have been analysed for assay optimisation are presented here:

a) Buffer optimisation: Following a small amount of buffer optimisation, heterogeneous melting analysis experiments were performed in 1.25 mM Tris.Cl pH8.0, 250 nM $MgCl_2$, 25 nM DTT. This hybridisation buffer was demonstrated to generate high quality melting curves with the majority of HyBeacons synthesised to date. However, the F17836 probe did not generate melting curves in this buffer even when hybridised to oligonucleotide targets. Subsequently, a study of $MgCl_2$ concentration versus HyBeacon melting temperature was performed. It was demonstrated that whilst no melt peaks were obtained with F17836 in the above buffer, very good quality melting curves were obtained in 50 mM Tris, 3 mM $MgCl_2$. Furthermore, it was demonstrated that there is a very strong correlation between $MgCl_2$ concentration and melt peak Tm. This relationship was studied for the F17831, TB0993, F17834, F17835 and B9414 HyBeacons, where $R^2$ values of 98.9%, 97.9%, 99.4%, 99.3% and 98.8% were generated respectively in regression analyses performed between 0.1 mM and 10 mM concentrations (see FIG. 14). More than a 10° C. shift in HyBeacon Tm may be achieved by altering $MgCl_2$ concentration. It may be possible to design differential beacon hybridisation assays where specific HyBeacon Tms are selected on the basis of buffer composition.

Amongst the commercially available PCR buffers tested in homogeneous amplification assays, TaKaRa buffer was found to be superior. Pharmacia, Taq Gold and TaKaRa PCR buffers and the corresponding Taq, Taq Gold and Z-Taq polymerases were compared for their effectiveness in HyBeacon assays. Assays performed with Taq Gold buffer and polymerase did not function at all, such that no real-time amplification curves or melt peaks were generated. Pharmacia and TaKaRa buffers both generate amplification curves and melt peaks with Taq and Z-Taq polymerases. However, TaKaRa buffer typically produces superior results even when additional MgCl$_2$ is included in the Pharmacia buffer. When amplification and detection efficiencies using Pharmacia PCR buffer were analysed in a series of MgCl$_2$ concentrations, the optimal concentration was found to be between 3.0 mM and 3.5 mM. TaKaRa buffer is known to contain 3.0 mM MgCl$_2$, but the other constituents are unknown.

Figure 17B:
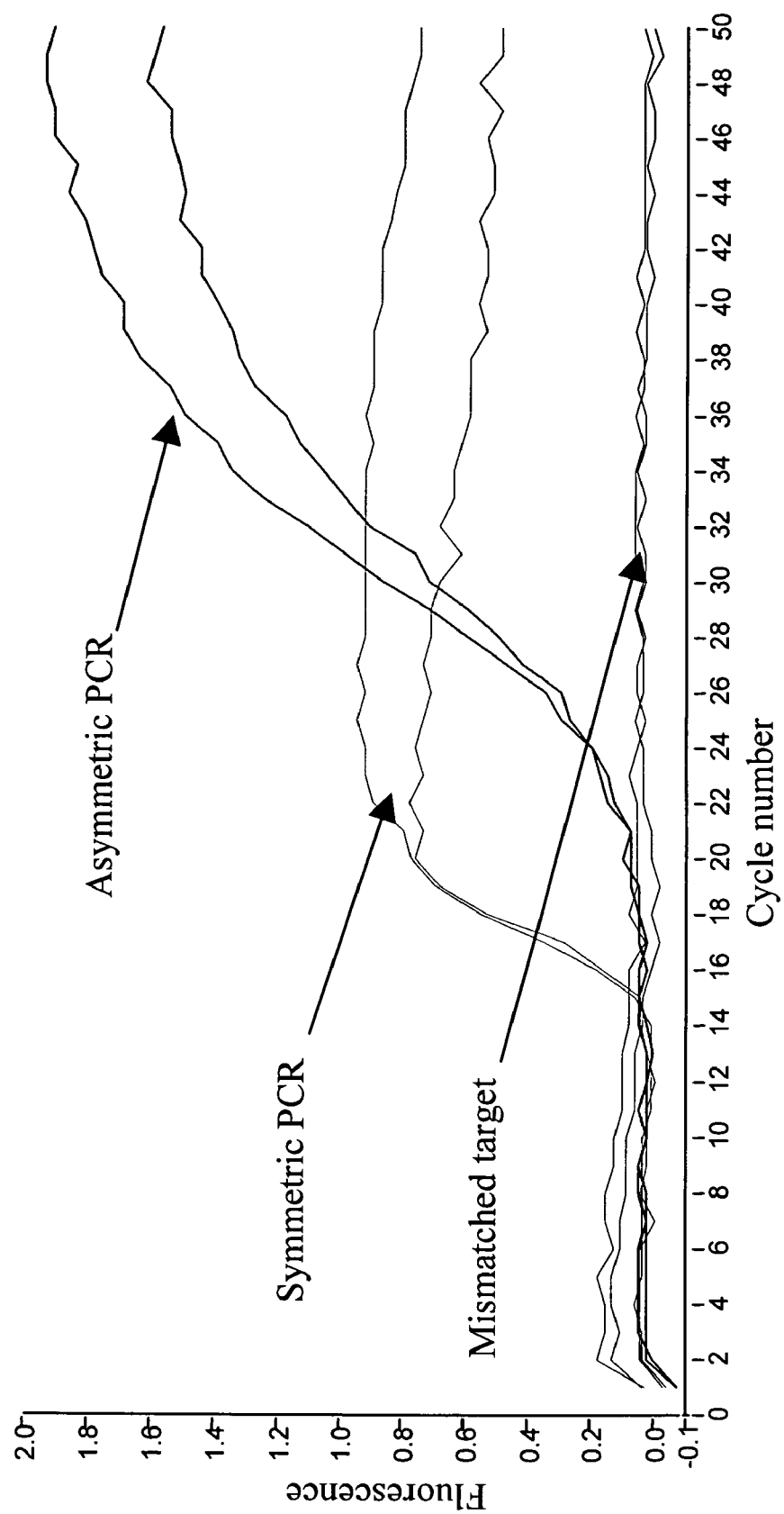

Stratagene's Optiprime kit was employed to obtain an indication of which components and conditions are required for the optimisation of HyBeacon PCR assays. The Optiprime kit consists of 12 individual buffers of various pHs (8.3, 8.8 and 9.2), containing different concentrations of MgCl$_2$ (1.5 mM and 3.5 mM) and KCl (25 mM and 75 mM). The efficiency of target amplification and detection was not noticeably affected by pH, but was significantly affected by MgCl$_2$ and KCl concentration, where 3.5 mM and 25 mM were optimal respectively (in 1× buffer). Using the information obtained from the Optiprime kit, a 10× HyBeacon PCR buffer (100 mM Tris.HCl pH8.8, 250 mM KCl, 35 mM MgCl$_2$) was constructed. This buffer was found to function relatively well in HyBeacon assays, generating high quality melting peaks in post-amplification analysis. However, the magnitude of the fluorescence increases resulting from real-time analysis was reduced compared with analyses performed in TaKaRa PCR buffer. Therefore, a series of PCR adjuncts were added to the HyBeacon PCR buffer in an attempt to improve the real-time target detection efficiency. Of the putative enhancers of PCR that were examined in the HyBeacon PCR buffer, only BSA was found to have a profound positive affect on the efficiency of real-time amplification. Working concentrations of BSA were studied between 0 μg/μl and 1 μg/μl. Increasing the concentration of BSA from 0 μg/μl to 10 ng/μl significantly enhanced the efficiency of real-time target detection. However, as a result of the increased BSA concentrations, the quality of post-amplification melting peaks was reduced. Therefore, an optimal BSA concentration was sought that permitted enhanced real-time amplification but did not decrease melt peak quality significantly. This optimal working concentration was found to be between 2.5 ng/μl and 5 ng/μl (see FIG. 15) and, therefore, 50 ng/μl of BSA was included in the 10× HyBeacon PCR buffer. This buffer has been demonstrated to function with a comparable efficiency to TaKaRa PCR buffer.

b) Choice of amplicon: With the exception of two probes F18140 and F18141, all of the HyBeacons tested generate very high quality melting curves with oligonucleotide homologues. However, not all of these probes produce high quality melts with large PCR targets. Alterations in amplicon size and primer position relative to the polymorphic site allow more efficient probe hybridisation and the generation of superior melting curves. Significant variations in 'real-time' amplification detection and melt peak discrimination efficiency have been observed for one of the NAT2*6 probes when using two amplicons differing by only 22 bp (FIG. 16).

c) Probe melting temperature: The Tm of a hybridisation beacon may affect the quality of post-amplification melting curves. Many of the early HyBeacons that were synthesised and tested were found to produce a background fluorescence effect at approximately 60-65° C. Numerous HyBeacons possessing matched Tms greater than approximately 58° C. were found to have their matched melt peak obscured by this background fluorescence effect, whilst the mismatched peaks with lower Tms were clearly visible in the melting trace. Probes possessing matched Tms of less than 58° C. may perform more efficiently in post-amplification melting analysis experiments. F-Q and F HyBeacon probes were designed for the CYP2D6*3 and *4 polymorphisms. The original CYP2D6 F HyBeacons possessed a number of advantages over the F-Q probes and generated high quality real-time PCR amplification data that permitted reliable discrimination of *3 and *4 SNPs. However, these F HyBeacon probes (2D63B and 2D64B) did not generate high quality melting peaks due to a significant overlap with a background fluorescence effect. Therefore, SNPs and homozygous and heterozygous samples could not be identified by melt analysis with these high Tm probes. The *3 and *4 HyBeacons were redesigned to be 2 (2D63C) and 3 (2D64C) nucleotides shorter respectively, such that the Tms were significantly reduced. Both of these reduced Tm probes generate high quality real-time amplification curves and post-amplification melt peaks, allowing extremely reliable SNP discrimination and heterozygote analysis. In contrast to the 2D63B and 2D64B probes, 2D63C and 2D64C generate both matched and mismatched melt peaks during post-amplification analysis, displaying little or no overlap with the background fluorescence effect.

d) HyBeacon concentration: The amount of HyBeacon included in an assay has been found to affect the quality of results generated, through variations in signal:background fluorescence ratios. If excess probe is included in an assay, the background fluorescence masks the hybridisation-mediated alterations in fluorescence. Superior quality melting curves have been observed in many instances when using reduced concentrations of HyBeacon. The optimal concentration of F HyBeacon probe, which permits the generation of high quality real-time amplification data and post-amplification melt peaks, is typically between 100 and 300 nM. Reduced HyBeacon concentrations appear to eliminate the background fluorescence affect described above.

e) Asymmetric PCR: All HyBeacon assays described hitherto have employed symmetric PCR protocols to amplify double-stranded DNA targets. Probes hybridising to double-stranded DNAs must compete with the target's homologous strand, such that this competitive binding may reduce HyBeacon hybridisation efficiency. Asymmetric PCR is a technique that is employed to generate single-stranded PCR products. HyBeacons may hybridise to single-stranded targets with higher efficiency than to double-stranded molecules due to the absence of the competing DNA strand. Asymmetric PCR was applied to eight HyBeacon SNP assays, to examine whether the technique is superior to symmetric amplification. Four of the eight HyBeacon assays possessed equivalent detection efficiencies in symmetric and asymmetric amplifications, with similar increases in fluorescence emission. One HyBeacon assay demonstrated a reduced efficiency in asymmetric assays compared with symmetric amplifications (FIG. 17*a*), whilst three other assays demonstrated greater increases in fluorescence emission with asymmetric amplification than with symmetric PCR (FIG. 17*b*). Furthermore, many of these HyBeacon assays produced superior post-amplification melting curves with asymmetrically amplified target compared with symmetric reactions (data not shown). Therefore, in some cases it may be beneficial to adopt asymmetric target amplification for potentially higher sensitivity SNP discrimination assays. However, the mechanism that generates asymmetric single-stranded DNAs is linear instead of logarithmic, therefore detection of amplification and discrimination of SNPs is achieved at a significantly higher cycle number (FIG. 17*b*) than in symmetric amplifications. This increase in threshold cycle could extend assay duration and may affect reactions containing low concentrations of genomic DNA.

(xi) Discrimination of SNPs on a Solid Phase.

NAT2*4 and *5A polymorphic targets were amplified from genomic DNA using a biotinylated primer of the same sequence as 195993' or 195991. Biotinylated PCR products were immobilised on 96 well streptavidin coated microtitre plates. DNA targets were denatured with NaOH and the non-biotinylated PCR strand was removed, leaving a single-stranded DNA target bound to the surface of the well. HyBeacon probes, typically F17832 and 0203002, were hybridised to the immobilised single-stranded targets. After hybridisation, excess probe was removed and melting analysis was performed using a DASH (Dynamic Allele Specific Hybridisation—Hybaid) instrument. HyBeacon melting curves were obtained from matched and mismatched immobilised targets, allowing reliable discrimination of SNPs (FIG. 18). The F17832 HyBeacon produced melting curves of poor quality in heterogeneous LightCycler assays. However, good quality melt analysis and reliable SNP discrimination was achieved with this probe in the DASH instrument. LightCycler and DASH melting analyses utilise double-stranded and single-stranded targets respectively. Significantly superior quality melting curves are obtained from single-stranded targets because of the lack of PCR homologue competing with the HyBeacon for target hybridisation. The successful use of the HyBeacons in both homogeneous and solid phase formats provides a versatile system in which large numbers of assays can be performed, potentially in some form of array system.

(xii) The 5'-3'-exonuclease Activity of Taq Polymerase.

To ensure that HyBeacon assays are distinct from the TaqMan system, two DNA polymerases, Deep Vent (New England Biolabs) and Stoffel fragment (Pharmacia), that lack 5'-3'-exonuclease activity were tested in 'real-time' amplification assays. 5'-3'-exonuclease activity is essential in TaqMan assays, where Taq polymerase is required to specifically digest TaqMan probes between fluorophore and quencher moieties, causing increases in fluorescence emission in the presence of perfectly matched targets. Deep Vent and Stoffel fragment polymerases were employed in homogeneous amplification assays to test the ability of a NAT2*4 F HyBeacon probe to detect target amplification in the absence of 5'-3'-exonuclease activity (FIG. 19). Reactions containing both types of polymerase did exhibit increases in fluorescence emission with matched templates throughout the course of amplification, whereas reactions containing mismatched template did not generate fluorescence increases. SNP discrimination may be achieved in 'real-time' and post-amplification formats with Deep Vent and Stoffel fragment polymerases. Therefore, these results indicate that the mechanism by which F HyBeacons detect DNA sequences by real-time PCR is distinct from that of the of 5'-3'-exonuclease assay, relying on increases in fluorescence emission caused directly by probe hybridisation rather than enzymatic separation of fluorophore and quencher moieties.

(xiii) Quantitative PCR Utilising HyBeacon Probes.

The ability to monitor the 'real-time' progress of PCR amplification completely revolutionises the approaches by which PCR-based quantitation of DNA and RNA may be performed. In 'real-time' quantitative PCR experiments, reactions are characterised by the point in time during cycling when amplification of a PCR product is first detected ($C_T$— threshold cycle) rather than the amount of PCR product accumulated after a fixed number of cycles. The higher the starting copy number of the nucleic acid target, the sooner a significant increase in fluorescence is observed. The potential of HyBeacon probes to quantify target DNA in 'real-time' amplifications was examined using the 2D64B, 2D64C* and DdeFL1 F HyBeacons. Quantitative HyBeacon PCR analyses were performed with LightCycler and ABI 7700 instruments. Ranges of DNA standards (known concentrations of PCR product or genomic DNA) were employed as templates for homogeneous PCR amplification. The threshold cycle for each DNA standard was measured and the log DNA concentrations were plotted against $C_T$ to generate 'straight line' standard curves. Threshold cycles obtained from samples containing 'unknown' concentrations of genomic DNA were plotted on the standard curve to calculate the concentration of DNA present in these reactions. The standard curves derived from HyBeacon quantitative PCRs were of very high quality with both LightCycler and ABI 7700 instruments, possessing correlation coefficients between 0.93 and 0.99 (FIG. 20). Calculation of DNA concentration from these standard curves was moderately accurate for the 'unknown' reactions tested, where calculated concentrations were in the correct order of magnitude. For example, $5.4 \times 10^4$ ng/µl, 700 ng/µl and 90 ng/µl 'unknown' samples had concentrations of $6.9 \times 10^4$ ng/µl, 1406 ng/µl and 115 ng/µl calculated from LightCycler standard curves respectively. Whereas, 285 ng/µl, 163 ng/µl and 53 ng/µl genomic samples were calculated as being 256 ng/µl, 137 ng/µl and 44 ng/µl with standard curves derived from the ABI 7700.

(xiv) Detection and Discrimination of Target Sequences without Prior DNA Extraction.

Obtaining a genotype from a patient sample, such as blood or buccal swab, typically requires that genomic DNA be extracted prior to PCR amplification and downstream analysis. DNA extraction protocols may be time-consuming, laborious and expensive. Therefore, to reduce the duration and cost of HyBeacon analyses, direct PCR amplification from saliva DNA was performed, removing the requirement for genomic DNA extraction. Combined with the rapid thermal cycling conditions of the LightCycler, direct target amplification from saliva permits polymorphic sequences to be genotyped within 35-40 minutes.

Polymorphic NAT2*4 and *5C sequences were amplified from 10 saliva samples and analysed with DdeFL1 and DdeFL1*4 HyBeacons, which are fully complementary to *5C and *4 alleles respectively. FIGS. 21 and 22 illustrate the real-time PCR data and melt peaks derived from DdeFL1 and DdeFL1*4 hybridisation to DNA sequences amplified from *5C/*5C (sample 1), *4/*4 (sample 2) and *4/*5C (sample 3) genotypes. Table 6 displays HyBeacon melting temperatures derived from DdeFL1 and DdeFL1*4 hybridisation to polymorphic NAT2 sequences. The real-time PCR and Tm data permits an individual's genotype, with respect to the *5C polymorphism, to be determined. Of the 10 saliva samples analysed, 3 were classified as being homozygous for the *5C allele, 1 was characterised as being homozygous for the *4 allele and 6 were found to be heterozygous. These genotypes, at the NAT2*5C gene locus, correlate with slow, fast and intermediate acetylation phenotypes respectively. To confirm the genotypes and phenotypes obtained from HyBeacon analysis of saliva samples, RFLP analysis was performed for saliva samples 1-3 (FIG. 23). A 179 bp PCR product amplified from *4/*4 DNA contains a single DdeI restriction site, which upon digestion results in 121 bp and 58 bp fragments. The *5C polymorphism generates an additional DdeI restriction site, such that digestion of 179 bp product amplified from *5C/*5C DNA results in 98 bp, 58 bp and 23 bp fragments. Digestion of product amplified from heterozygous saliva samples results in 121 bp, 98 bp, 58 bp and 23 bp fragments. Saliva samples 1-3 are typed as being homozygous *5C, homozygous *4 and heterozygous respectively by both RFLP and HyBeacon methodologies. Therefore, the data presented here demonstrates that reliable amplification, detection and discrimination of polymorphic sequences may be performed without the need for purification of high quality DNA.

TABLE 6

Tm values derived from melting curve analysis of amplified NAT2 *4 and *5C sequences. The DdeFL1 and DdeFL1*4 HyBeacons are perfectly matched to *5C and *4 alleles respectively. The means and standard errors of matched and mismatched melt peaks are detailed for each saliva sample and for all samples collectively. NP indicates the absence of a particular peak in a given melting trace and '—' shows that the DdeFL1*4 assay was not performed for a particular saliva sample.

| Saliva sample | DdeFL1 (mean °C. ± SE) | | DdeFL1*4 (mean °C. ± SE) | | Genotype | Associated acetylation phenotype |
|---|---|---|---|---|---|---|
| | Tm1 | Tm2 | Tm1 | Tm2 | | |
| 1 | NP | 53.8 ± 0.1 | 42.0 ± 0.3 | NP | S1d/S1d | Slow |
| 2 | 47.5 ± 0.1 | NP | NP | 52.1 ± 0.1 | F1/F1 | Fast |
| 3 | 47.4 ± 0.1 | 54.1 ± 0.1 | 42.6 ± 0.1 | 52.4 ± 0.5 | S1d/F1 | Intermediate |
| 4 | 47.9 ± 0.1 | 54.2 ± 0.1 | — | — | S1d/F1 | Intermediate |
| 5 | 47.7 ± 0.1 | 54.1 ± 0.2 | — | — | S1d/F1 | Intermediate |
| 6 | NP | 53.8 ± 0.2 | 42.3 ± 0.3 | — | S1d/S1d | Slow |
| 7 | 47.9 ± 0.3 | 54.1 ± 0.2 | — | — | S1d/F1 | Intermediate |
| 8 | 47.9 ± 0.2 | 54.2 ± 0.1 | — | — | S1d/F1 | Intermediate |
| 9 | 47.7 ± 0.0 | 54.1 ± 0.1 | — | — | S1d/F1 | Intermediate |
| 10 | NP | 54.2 ± 0.1 | — | — | S1d/S1d | Slow |
| Total | 47.6 ± 0.1 | 54.1 ± 0.1 | 42.4 ± 0.1 | 52.3 ± 0.2 | — | — |

(xv) Detection of RNA Sequences

The potential for the detection of RNA targets was assessed. Initially, a HyBeacon probe was designed to detect a NASBA (Nucleic Acid Sequence Based Amplification) RNA product. This product was not detected by the generation of HyBeacon melt peaks in melting curve analyses, possibly due to degradation of the RNA product. Therefore, oligonucleotide homologues consisting of DNA or RNA were synthesised to analyse the hybridisation of the HyBeacon probe. Initially, melting peaks were derived from the DNA target but not from the RNA oligonucleotide. It was not until the concentration of the RNA target was increased to 2 µM that melt peaks, characteristic of probe hybridisation, were derived (data not shown). It was demonstrated that the melting temperature of HyBeacon/RNA duplexes are significantly reduced compared with HyBeacon/DNA duplexes, suggesting that hybridisation to RNA is considerably less stable than hybridisation to DNA. Therefore, unless high concentrations of RNA targets can be generated during analyses, HyBeacon probes may be unable to reliably detect them.

(xvi) Mechanism of Sequence Detection

Hybridisation of HyBeacon probes to complementary target DNA sequences results in significant alterations in the amount of fluorescence emission despite the absence of probe quencher moieties. Nucleotide residues, especially guanine, have been demonstrated to effect fluorescence emission through static and dynamic quenching mechanisms. Therefore, quenching of HyBeacon fluorescence could potentially arise from the oligonucleotide component of the probe through base-dye stacking and electron transfer events. HyBeacon hybridisation to target sequences may alter the orientation of the fluorophore moiety relative to the oligonucleotide component, affecting the amount of electron transfer between dye and base. Alternatively, changes in base-dye stacking resulting from duplex formation, e.g. intercalation of the fluorophore into the base stack, may alter the amount of fluorescence quenching. When HyBeacon probes hybridise to target DNA sequences, a conformation shift may relieve a small but detectable amount of the fluorescence quenching imposed by the HyBeacon oligonucleotide. Reduced quenching results in an increase in the amount of fluorescence emission, permitting sequence detection and allele discrimination. To investigate the molecular mechanism by which HyBeacon probes function, fluorescence and u.v. spectroscopic techniques may be employed to analyse possible alterations of quantum yield, fluorescence lifetime and emission wavelength occurring between single-stranded and duplex states.

(xvii) Validation of Hybridisation Probe Assays Using the Factor V Leiden Polymorphism.

Activated Protein C (APC) is a serine protease and anticoagulant that is responsible for the inactivation of factor V. Normally, factor V is inactivated by cleavage of the protein at Arg506 and subsequent cleavage at Arg306. In individuals that contain a point mutation in the factor V gene (R506Q), factor V is inactivated only by cleavage at R306. Without prior cleavage at R506, inactivation of factor V occurs at an approximately ten times slower rate. Therefore, the factor V Leiden polymorphism affects the anticoagulation potential of APC, such that individuals that possess the mutation have an increased risk for deep vein thrombosis and pulmonary embolism (5-10 fold and 50-100 fold increased risk in heterozygous and homozygous individuals respectively). The factor V Leiden mutation is present in approximately 6% of the general population and has recently been linked to the fatal thromboses ("economy class syndrome") that occur in individuals during, or shortly after, long flights. The hybridisation probe technology has the potential to offer a rapid, simple and accurate method for the detection of the factor V Leiden mutation, possibly in a 'point-of-care' scenario.

A hybridisation beacon assay was developed to screen samples for the factor V Leiden mutation and to validate the probe system in terms of specificity, reproducibility, sensitivity and robustness. The F hybridisation beacon FVG1, 5'(CT-GTAFTCCTCGCCTGTCC3P)3' (Sequence ID No. 61), was employed to analyse DNA sequences containing the factor V Leiden (R506Q) polymorphism, being fully complementary to the 'wild-type' allele.

134 bp PCR products, flanking the R506Q polymorphism, were amplified using FVF1 5' (GACTACTTCTMTCTGTMGAGCAG)3' (Sequence ID No. 62) and FVR3 5' (CCATTATTTAGCCAGGAGAC)3' (Sequence ID No. 63) primers. Following a denaturation reaction step (95° C. 5-10 min), polymorphic factor V sequences were amplified in LightCycler capillaries using 40 cycles, comprising denaturation (95° C. 0 s), primer annealing (55° C. 10 s) and extension of products (72° C. 10 s). Fluorescence acquisition was performed once per cycle at the end of each primer-annealing step. Following amplification, reactions were immediately denatured (95° C. 0 s) and cooled (35° C. 2 min) prior to melt analysis (35° C. to 75° C., with a 0.1° C./s transition rate), where fluorescence was acquired continuously. Melt peaks were constructed using the Light-Cycler software (version 3) by plotting the negative derivative of fluorescence with respect to temperature (−dF/dT on the y-axis) against temperature (x-axis).

Factor V sequences were also amplified and analysed using an ABI PRISM® 7700 instrument. Following a denaturation step (95° C. 5 min), sequences were amplified using 40 cycles comprising denaturation (95° C. 15 s), primer annealing (55° C. 30 s) and extension of products (72° C. 30 s). Fluorescence was acquired continuously throughout amplification. Following amplification, samples were denatured (95° C. 15 s) and cooled (35° C. 20 s) prior to melt analysis (35° C. to 95° C. over 19 min 59 s), where fluorescence was acquired only during the melting phase. Hybridisation beacon melt peaks were obtained from exported multi-component data using the Dissociation Curves 1.0 software (Applied Biosystems).

The hybridisation beacon FVG1 permits samples to be reliably genotyped with respect to the factor V Leiden polymorphism. The probe generates single melt peaks possessing Tms of approximately 59° C. and 48.5° C. when hybridised to homozygous wild-type and mutant sequences respectively. Traces possessing both melt peaks permit reliable identification of heterozygous samples (FIG. 24). Ten clinical genomic DNA samples (5 homozygous wild-type and 5 heterozygous) that had been previously typed for the factor V polymorphism by RFLP analysis were correctly genotyped with the FVG1 probe using LightCycler and ABI PRISM 7700 instruments (FIG. 24). Nine saliva samples were also typed for the factor V Leiden polymorphism. All saliva samples were found to be homozygous for the wild-type allele, where FVG1 generated melt peaks possessing Tms of 59.0±0.03° C. in the LightCycler instrument.

Independent analyses have been found to generate melt peaks possessing slightly different Tms. Small variations of probe melting temperature may arise from intra-run, intra-run, inter-instrument and inter-individual sources and also from variable polymerase quantities, annealing temperatures etc. Whilst these variations of probe melting temperature do not affect the efficiency and accuracy of HyBeacon assays (FIG. 25), it is essential to account for them and establish Tm ranges/zones to identify wild-type and mutant alleles. Using data derived from clinical genomic DNA samples and control templates, 99.9% confidence intervals were calculated for matched and mismatched probe Tms. Based on this data, Tm zones of 56° C. to 60° C. and 46° C. to 50° C. were established for wild-type and mutant factor V alleles respectively. Use of these Tm zones in allele discrimination assays will ensure that melt peaks and samples are identified correctly with at least 99.9% confidence. The Tm zones have been applied to the data derived from a large number of samples. All of the melt peak Tms were located within either the wild-type or mutant zones, with no Tm values observed between the two discrete ranges. This data suggests that the hybridisation beacon technology may be employed to genotype samples with an extremely high degree of confidence.

(xviii) Two Fluorophore Hybridisation Probes

The hybridisation probe FVG11, 5' (CTGTAFTCCTCGCC FGTCC3P)3' (Sequence ID No. 64), which is fully complementary to the 'wild-type' allele of the factor V Leiden (R506Q) allele, was employed to investigate the efficiency of probes possessing two fluorophores, where both fluorophores were the dU C6 FAM monomer. The double-labelled probe efficiently detected and discriminated polymorphic factor V sequences using the real-time PCR method described above (FIG. 26).

The melting temperature of the dual-labelled probe was found to be considerably reduced when compared with the FVG1 probe, that possesses a single fluorophore attachment, since dU C6 FAM monomers decrease probe stability compared with unlabelled duplexes. Tms derived from melt peak analyses suggest that the melting temperatures of probes are reduced by approximately 4° C. per fluorescent monomer.

Despite the increased background fluorescent signal emitted by the dual-labelled probe, the efficiency of target detection and discrimination may be significantly increased compared with the single fluorophore equivalent. Dual-labelled probes generated melt peaks that were of approximately 4 times the height of the single-labelled probe.

CONCLUSIONS

Hybridisation beacons (HyBeacons) have been demonstrated to detect specific DNA sequences through the increases in fluorescence emission that are generated as a direct result of probe hybridisation to complementary target sequences. The amount of fluorescence emission and the Tm of probe/target duplexes allow discrimination of SNPs in oligonucleotide and amplified PCR sequences. Results reported here demonstrate that HyBeacon assays permit the identification of homozygous and heterozygous samples using a single probe and that the use of multiple HyBeacon probes in a single tube/well assay has the potential for multiplex analysis. Furthermore, HyBeacons have been demonstrated to quantify DNA targets in 'real-time' PCR assays.

HyBeacon probes are an alternative to the commercial systems currently available (molecular beacons, Scorpions, FRET probes and TaqMan™ probes) for sequence detection, SNP discrimination and DNA quantification. Detection assays using HyBeacons are attractive due to their simple mode of action, lacking secondary structure and a requirement for an enzyme and their ability to identify heterozygous DNA using a single probe.

Molecular diagnostic assays may be performed by a homogeneous HyBeacon method (as described above), where target amplification and detection are performed in a single tube. Alternatively, robotic isolation of amplified target or solid phase immobilisation, followed by buffer replacement and addition of HyBeacon, may form a high throughput detection system. Differential hybridisation assays could be performed in microarray or macroarray formats, where either the probes or more preferably the targets are immobilised prior to HyBeacon melting analysis.

Two variants of the HyBeacon probe have been evaluated. Probes may contain both fluorophore and quencher moieties linked to internal nucleotide residues (F-Q HyBeacon) or may contain only the fluorophore component (F HyBeacon). Both variants have been demonstrated to reliably discriminate SNPs in homogeneous and heterogeneous formats. However, F HyBeacons have obvious advantages over the F-Q design:

At present, fluorophore and quencher moieties may only be positioned on T residues. Therefore, F HyBeacons are significantly more straightforward to design with reduced constraints, such that the number of residues separating fluorophore and quencher moieties and possible angular disposition effects do not need to be considered.

Due to the absence of a quencher, F HyBeacons are less expensive to synthesise and assays require approximately five times less probe per reaction (less than 200 nM) compared with F-Q probes.

F HyBeacons have been demonstrated to have the potential to generate superior quality post-amplification melting curves in 'real-time' homogeneous assays.

In contrast to the two F-Q probes required for heterozygote analysis, F HyBeacons have been demonstrated to identify heterozygous samples using a single probe.

The invention is not limited to the embodiments hereinbefore described which may be varied in construction and detail without departing from the spirit of the invention.

The invention claimed is:

1. A hybridisation beacon which is an oligonucleotide where (a) the oligonucleotide has substantially no secondary structure, (b) the oligonucleotide is formed of nucleotide residues of which more than one is labelled with a fluorescein based reporter wherein the beacon does not include an associated quencher, (c) the reporter-labelled nucleotide residues are positioned internally within the oligonucleotide sequence, (d) the oligonucleotide is fully complementary to and hybridizes to one allele of a known target polynucleotide which, optionally, has a known polymorphism/mutation, the oligonucleotide capable of exhibiting a higher level of signal when in the form of the hybrid than when in single-stranded form, and (e) the oligonucleotide probe is modified at its 3'end so as to prevent chain extension during PCR amplification.

2. The hybridisation beacon of claim 1, wherein the known polymorphism is a point mutation or a single base insertion or deletion.

3. The hybridisation beacon of claim 1, wherein the known polymorphism of the polynucleotide target is complementary to a nucleotide residue towards the centre of the hybridisation beacon molecule.

4. The hybridisation beacon of claim 1, which is immobilised on a support.

5. An array of oligonucleotide probes immobilised at spaced locations on or within a support, wherein the oligonucleotide probes are different and each oligonucleotide probe is a hybridisation beacon according to claim 1.

6. A method of investigating a polynucleotide target having a known or suspected polymorphism, which method comprises providing a hybridisation beacon of claim 1, incubating the polynucleotide target with the hybridisation beacon to form a hybrid, the hybridisation beacon exhibiting a higher level of signal when in the form of the hybrid than when in single-stranded form, and observing the level of signal of the hybridisation beacon at a predetermined temperature, or over a range of temperatures, near the melting temperature of the hybrid.

7. The method of claim 6, wherein the reporter is a fluorophore, and the signal whose level is observed is fluorescence.

8. The method of claim 6, wherein the method is used to detect, identify or quantitate the presence or the amount of target sequence present in a sample.

9. The method of claim 6, wherein the hybridisation beacon has a sequence complementary to one allele of the target polynucleotide.

10. The method of claim 9, wherein each of two or more different hybridisation beacons has a sequence complementary to a different allele of the target polynucleotide.

11. The method of claim 6, wherein the predetermined temperature, at which the level of signal of the hybridisation beacon is observed, is intermediate between the melting temperatures of the hybrids formed with different alleles of the polynucleotide target.

12. The method of claim 6, wherein the range of temperatures encompass the melting temperature of the hybrid.

13. The method of claim 6, wherein observation is made of the rate of change of the level of signal with change of temperature.

14. The method of claim 6, wherein amplification of the polynucleotide target is performed in the presence of the hybridisation beacon.

15. The method of claim 6, wherein the polynucleotide target is a PCR amplimer.

16. The method of claim 14, wherein the polynucleotide amplification is performed by Polymerase Chain Reaction (PCR), Ligase Chain Reaction (LCR), Strand Displacement Amplification (SDA), Transcription Mediated Amplification (TMA), Rolling Circle Amplification (RCA) or Nucleic Acid Sequence Bases Amplification (NASBA).

17. The method of claim 14, wherein observation of the signal of the hybridisation beacon is made during the amplification of the polynucleotide target.

18. The method of claim 6, wherein hybridisation beacons are employed to detect and discriminate targets amplified from samples, without prior DNA extraction.

19. The method of claim 16, wherein the PCR reaction is an asymmetric amplification.

20. The method of claim 6, wherein the hybridisation beacon, the target sequence or both are immobilised on a support.

21. A method for differentiation between homozygous and heterozygous polynucleotide targets, which comprises using a hybridisation beacon according to claim 1.

22. A method for determining the presence of a target nucleic acid sequence in a biological sample comprising:
- combining the biological sample with a pair of primers configured for amplifying a selected segment of the target nucleic acid sequence and a fluorescent detecting entity consisting essentially of an oligonucleotide probe formed of nucleotide residues of which more than one is labelled with a reporter wherein the probe does not include an associated quencher, and
- wherein the probe comprises an oligonucleotide having a sequence complementary to a locus of the selected segment of the target nucleic acid sequence, and having a fluorescent label exhibiting a sequence-specific hybridization-dependent emission attached thereto, wherein hybridization of the probe to the locus results in an increase in fluorescent emission of the fluorescent label,
- adding a polymerase and amplifying the selected segment of the nucleic acid sequence through a plurality of amplification cycles,
- illuminating the biological sample, and
- monitoring the hybridization-dependent fluorescent emission.

23. The method of claim 18, wherein the sample is saliva.

24. A method of making a hybridisation beacon which is an oligonucleotide, the method comprising
(i) selecting a target polynucleotide which, optionally, has a known polymorphism/mutation;
(ii) synthesizing an oligonucleotide which is fully complementary to and hybridizes to one allele of the target polynucleotide, and where (a) the oligonucleotide has substantially no secondary structure, (b) the oligonucleotide is formed of nucleotide residues of which more than one is labelled with a fluorescein based reporter wherein the beacon does not include an associated quencher, (c) the reporter-labelled nucleotide residues are positioned internally within the oligonucleotide sequence, and (d) the oligonucleotide probe is modified at its 3' end so as to prevent chain extension during PCR amplification.

25. A hybridisation beacon which is an oligonucleotide where (a) the oligonucleotide has substantially no secondary structure, (b) the oligonucleotide is formed of nucleotide residues of which the base of more than one is labelled with a fluorophore reporter wherein the beacon does not include an associated quencher, (c) the reporter-labelled nucleotide residues are positioned internally within the oligonucleotide sequence, (d) the oligonucleotide is fully complementary to and hybridizes to one allele of a known target polynucleotide which, optionally, has a known polymorphism/mutation, and (e) the oligonucleotide probe is modified at its 3'end so as to prevent chain extension during PCR amplification.

26. The hybridisation beacon of claim 25, wherein each of the reporter-labelled nucleotide residues is a uracil.

27. A method of investigating a polynucleotide target having a known or suspected polymorphism, which method comprises providing a hybridisation beacon of claim 25, incubating the polynucleotide target with the hybridisation beacon to form a hybrid, the hybridisation beacon exhibiting a higher level of signal when in the form of the hybrid than when in single-stranded form, and observing the level of signal of the hybridisation beacon at a predetermined temperature, or over a range of temperatures, near the melting temperature of the hybrid.

28. A method for differentiation between homozygous and heterozygous polynucleotide targets, which comprises using a hybridisation beacon according to claim 25.

29. A method of making a hybridisation beacon which is an oligonucleotide, the method comprising
(i) selecting a target polynucleotide which, optionally, has a known polymorphism/mutation;
(ii) synthesizing an oligonucleotide which is fully complementary to and hybridizes to one allele of the target polynucleotide, and where (a) the oligonucleotide has substantially no secondary structure, (b) the oligonucleotide is formed of nucleotide residues of which the base of more than one is labelled with a fluorophore reporter wherein the beacon does not include an associated quencher, (c) the reporter-labelled nucleotide residues are positioned internally within the oligonucleotide sequence, and (d) the oligonucleotide probe is modified at its 3' end so as to prevent chain extension during PCR amplification.

* * * * *

SEQUENCE LISTING

```
<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: DNA/RNA
<220> FEATURE:
<223> OTHER INFORMATION: Synthetic Oligonucleotide

<400> SEQUENCE: 1
gaatctggta ucuggaccaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 2
gaatctggua tcuggaccaa                                                   20

<210> SEQ ID NO 3
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 3
gaatcuggta tcuggaccaa                                                   20

<210> SEQ ID NO 4
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 4
gaatcuggta ccuggaccaa                                                   20

<210> SEQ ID NO 5
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 5
gaatcugcta ccuggaccaa                                                   20
```

```
<210> SEQ ID NO 6
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 6
gatttggtcc agguaccaga utc                                              23

<210> SEQ ID NO 7
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 7
gatttggtcc agguaccaga utc                                              23

<210> SEQ ID NO 8
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 8
gatutggtcc agguaccaga ttc                                              23

<210> SEQ ID NO 9
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 9
gatutggtcc agguaccaga ttc                                              23

<210> SEQ ID NO 10
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 10
gagaggaatc uggtaccugg acc                                              23

<210> SEQ ID NO 11
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide
```

```
<400> SEQUENCE: 11
gaatcuggta ctuggaccaa                                              20

<210> SEQ ID NO 12
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 12
cutgaaccuc gaacaattga ag                                           22

<210> SEQ ID NO 13
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 13
cttgaaccuc gaacaautga ag                                           22

<210> SEQ ID NO 14
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 14
cttgaaccuc gaacaatuga ag                                           22

<210> SEQ ID NO 15
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 15
cttcaattgu tcgaggutca ag                                           22

<210> SEQ ID NO 16
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 16
cttcaautgt tcgaggutca ag                                           22

<210> SEQ ID NO 17
<211> LENGTH: 22
<212> TYPE: DNA
<213> ORGANISM: Artificial Sequence
```

```
<220> FEATURE:
<223> OTHER INFORMATION: Combined DNA/RNA
<220> FEATURE:
<223> OTHER INFORMATION: Synthetic Oligonucleotide

<400> SEQUENCE: 17
cttcaautgt ttgaggutca ag                                              22

<210> SEQ ID NO 18
<211> LENGTH: 24
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 18
gaagtgcuga gaaauatatt taag                                            24

<210> SEQ ID NO 19
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 19
gatttggtcc agguaccaga utc                                             23

<210> SEQ ID NO 20
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 20
gatutggtcc agguaccaga ttc                                             23

<210> SEQ ID NO 21
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 21
gaatcuggta ccuggaccaa                                                 20

<210> SEQ ID NO 22
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 22
gaatcuggta ctuggaccaa                                                 20
```

```
<210> SEQ ID NO 23
<211> LENGTH: 21
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 23
cccaggucat cctgugctca g                                             21

<210> SEQ ID NO 24
<211> LENGTH: 18
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 24
ggggcgtccu gggggugg                                                 18

<210> SEQ ID NO 25
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 25
gagaggaatc uggtacctgg acc                                           23

<210> SEQ ID NO 26
<211> LENGTH: 23
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 26
gagaggaatc uggtacttgg acc                                           23

<210> SEQ ID NO 27
<211> LENGTH: 24
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 27
gaagtgcuga aaaatatatt taag                                          24

<210> SEQ ID NO 28
<211> LENGTH: 24
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide
```

```
<400> SEQUENCE: 28
gaagtgcuga gaaatatatt taag                                          24

<210> SEQ ID NO 29
<211> LENGTH: 24
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 29
gaagtgcuga aaaatatatt taag                                          24

<210> SEQ ID NO 30
<211> LENGTH: 22
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 30
cttcaautgt tcgaggttca ag                                            22

<210> SEQ ID NO 31
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 31
cctggtgaug gatcccttac                                               20

<210> SEQ ID NO 32
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 32
cctggtgaug aatcccttac                                               20

<210> SEQ ID NO 33
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 33
cccaggucat cctgtgctc                                                19

<210> SEQ ID NO 34
<211> LENGTH: 21
<212> TYPE: DNA
<213> ORGANISM: Artificial Sequence
```

```
<220> FEATURE:
<223> OTHER INFORMATION: Combined DNA/RNA
<220> FEATURE:
<223> OTHER INFORMATION: Synthetic Oligonucleotide

<400> SEQUENCE: 34
cccaggucat cctgtgctca g                                             21

<210> SEQ ID NO 35
<211> LENGTH: 18
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 35
cccaggucat ccgtgctc                                                 18

<210> SEQ ID NO 36
<211> LENGTH: 16
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 36
gggcgucctg ggggtg                                                   16

<210> SEQ ID NO 37
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 37
ggggcgucct gggggtggg                                                19

<210> SEQ ID NO 38
<211> LENGTH: 16
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 38
gggcgtctug ggggtg                                                   16

<210> SEQ ID NO 39
<211> LENGTH: 16
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 39
gggcgucctg ggggtg                                                   16
```

```
<210> SEQ ID NO 40
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 40
cattgaggac cgugttcaag                                                      20

<210> SEQ ID NO 41
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 41
cattgaggac tgugttcaag                                                      20

<210> SEQ ID NO 42
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 42
gaaggucaat gtatctctgg                                                      20

<210> SEQ ID NO 43
<211> LENGTH: 20
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 43
gaaggucaag gtatctctgg                                                      20

<210> SEQ ID NO 44
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 44
gattattucc cgggaaccc                                                       19

<210> SEQ ID NO 45
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide
```

```
<400> SEQUENCE: 45
gattattucc caggaaccc                                                    19

<210> SEQ ID NO 46
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 46
taccuggatc caggggggtg                                                   19

<210> SEQ ID NO 47
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 47
taccuggatt caggggggtg                                                   19

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 48
ctgctctctc ctgatttggt cc                                                22

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 49
cctctagaat taatttctgg g                                                 21

<210> SEQ ID NO 50
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 50
cctatagaaa attcaattat aaag                                              24

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
cacgagattt ctccccaagg                                                   20
```

```
<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
cctgccaaag aagaaacacc                                               20

<210> SEQ ID NO 53
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 53
gtattcatag actcaaaatc ttc                                           23

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
gaagaggttg aagaagtgct g                                             21

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 55
caagggttta ttttgttcct tattc                                         25

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
ccaccgtggc agccactctc                                               20

<210> SEQ ID NO 57
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 57
ccagctggat gagctgctaa c                                             21

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 58
cgaagcggcg cccgcagg                                                 18

<210> SEQ ID NO 59
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 59
gggacgggga aggcgacc                                                 18

<210> SEQ ID NO 60
<211> LENGTH: 930
<212> TYPE: DNA
<213> ORGANISM: Homo Sapiens

<400> SEQUENCE: 60
atggacattg aagcatattt tgaaagaatt ggctataaga actctaggaa caaattggac    60
ttggaaacat taactgacat tcttgagcac cagatccggg ctgttccctt tgagaacctt   120
aacatgcatt gtgggcaagc catggagttg gcttagagg ctattttga tcacattgta    180 agaagaaacc ggggtgggtg gtgtctccag gtcaatcaac ttctgtactg ggctctgacc   240
acaatcggtt tcagaccac aatgttagga gggtattttt acatccctcc agttaacaaa    300
tacagcactg gcatggttca ccttctcctg caggtgacca ttgacggcag gaattacatt   360
gtcgatgctg gtctggaag ctcctcccag atgtggcagc tctagaatt aatttctggg    420 aaggatcagc ctcaggtgcc ttgcattttc tgcttgacag aagagagagg aatctggtac   480
ctggaccaaa tcaggagaga gcagtatatt acaaacaaag aatttcttaa ttctcatctc   540
ctgccaaaga gaaacacca aaaaatatac ttatttacgc ttgaacctcg aacaattgaa    600
gattttgagt ctatgaatac atacctgcag acgtctccaa catcttcatt tataaccaca   660
tcattttgtt ccttgcagac cccagaaggg gtttactgtt tggtgggctt catcctcacc   720
tatagaaaat tcaattataa agacaataca gatctggtcg agtttaaaac tctcactgag   780
gaagaggttg aagaagtgct gaaaaatata tttaagattt ccttggggag aaatctcgtg   840
cccaaacctg gtgatggatc ccttactatt tagaataagg aacaaaataa acccttgtgt   900
atgtatcacc caactcacta attatcaact                                    930

<210> SEQ ID NO 61
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 61
ctgtautcct cgcctgtcc                                                19

<210> SEQ ID NO 62
<211> LENGTH: 25
<212> TYPE: DNA
<213> ORGANISM: Artificial Sequence
<220> FEATURE:
<223> OTHER INFORMATION: Synthetic Oligonucleotide
```

```
<400> SEQUENCE: 62
gactacttct aatctgtaag agcag                                          25

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
ccattattta gccaggagac                                                20

<210> SEQ ID NO 64
<211> LENGTH: 19
<212> TYPE: DNA
<213> ORGANISM: Artificial Sequence
<220> FEATURE:
<223> OTHER INFORMATION: Combined DNA/RNA
<220> FEATURE:
<223> OTHER INFORMATION: Synthetic Oligonucleotide

<400> SEQUENCE: 64
ctgtautcct cgccugtcc                                                 19
```